US006642383B2

(12) United States Patent
Lazzari et al.

(10) Patent No.: US 6,642,383 B2
(45) Date of Patent: Nov. 4, 2003

(54) OXOPIPERAZINYL DERIVATIVES AND LIGHT STABILIZED COMPOSITIONS

(75) Inventors: Dario Lazzari, Casalecchio di Reno (IT); Graziano Zagnoni, Vergato (IT); Mirko Rossi, San Lazzaro di Savena (IT); Alessandro Zedda, Casalecchio di Reno (IT); Valerio Borzatta, Bologna (IT); Stephen Mark Andrews, New Fairfield, CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/855,905

(22) Filed: May 15, 2001

(65) Prior Publication Data

US 2002/0115859 A1 Aug. 22, 2002

Related U.S. Application Data

(63) Continuation of application No. 09/241,483, filed on Feb. 1, 1999, now abandoned.

(30) Foreign Application Priority Data

Feb. 2, 1998 (EP) .......................................... 98810074

(51) Int. Cl.[7] .................... C07D 241/06; C07D 401/12; C08K 5/5317

(52) U.S. Cl. ......................... 544/383; 544/384; 544/49; 524/100; 524/102; 524/103; 524/131

(58) Field of Search ................................ 544/383, 384, 544/49

(56) References Cited

U.S. PATENT DOCUMENTS

| | | | | |
|---|---|---|---|---|
| 4,167,512 A | | 9/1979 | Lai | 260/239.3 |
| 4,190,571 A | | 2/1980 | Lai et al. | 260/45.8 |
| 4,240,961 A | | 12/1980 | Lai | 260/239.3 |
| 4,246,412 A | | 1/1981 | Lai | 544/384 |
| 4,292,240 A | | 9/1981 | Lai et al. | 260/239.3 |
| 4,297,497 A | | 10/1981 | Lai | 544/384 |
| 4,455,401 A | | 6/1984 | Son et al. | 524/91 |
| 4,466,916 A | * | 8/1984 | Lai et al. | 544/231 |
| 4,477,665 A | | 10/1984 | Lai et al. | 544/384 |
| 4,480,092 A | | 10/1984 | Lai et al. | 544/113 |
| 4,547,538 A | | 10/1985 | Lai et al. | 524/100 |
| 4,629,752 A | | 12/1986 | Layer et al. | 524/100 |
| 4,639,479 A | | 1/1987 | Lai et al. | 524/100 |
| 4,675,353 A | | 6/1987 | Son et al. | 524/96 |
| 4,692,487 A | | 9/1987 | Son et al. | 524/100 |
| 4,722,806 A | | 2/1988 | Lai et al. | 252/403 |
| 4,780,495 A | | 10/1988 | Lai et al. | 524/100 |
| 5,047,460 A | | 9/1991 | Kletecka et al. | 524/100 |
| 5,049,600 A | | 9/1991 | Kletecka | 524/88 |
| 5,053,505 A | | 10/1991 | Son et al. | 540/575 |

(List continued on next page.)

FOREIGN PATENT DOCUMENTS

| | | |
|---|---|---|
| EP | 0029088 | 5/1981 |
| EP | 0299426 | 1/1989 |

(List continued on next page.)

OTHER PUBLICATIONS

Lai, Synthesis, (1984), p. 124–126.
Lai, Synthesis, (1981), p. 40–42.
Lai, J. Org. Chem. vol. 45, pp. 754–755, 1980.

*Primary Examiner*—John M. Ford
*Assistant Examiner*—Venkataraman Balasubramanian
(74) *Attorney, Agent, or Firm*—David R. Crichton

(57) ABSTRACT

Compounds of the formula (I)

(I)

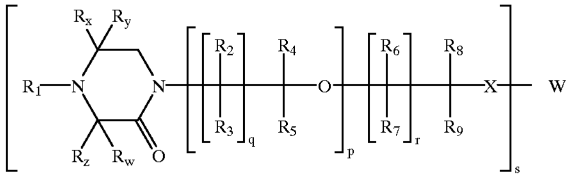

wherein p is zero or 1; q and r, independently of each other, are an integer from 1 to 6; and s is a number ranging from 1 to 8;

X is —O— or, when p is 1, X is also a group

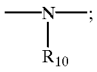

$R_w$, $R_x$, $R_y$ and $R_z$ are, independently of each other, $C_1$–$C_{18}$alkyl, $C_5$–$C_{12}$cycloalkyl or $C_1$–$C_5$hydroxyalkyl, especially methyl;

$R_1$ is hydrogen; $C_1$–$C_{18}$alkyl; oxyl; OH; $CH_2CN$; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–$C_{15}$phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1$–$C_{18}$alkanoyloxy; glycidyl; or a group —$CH_2CH(OH)$—G, in which G is hydrogen, methyl or phenyl;

$R_2$ is hydrogen, $C_1$–$C_8$alkyl, $C_5$–$C_{12}$cycloalkyl or $C_1$–$C_4$hydroxyalkyl;

$R_3$, $R_4$, $R_5$ independently of each other are hydrogen, $C_1$–$C_8$alkyl or $C_5$–$C_{12}$cycloalkyl; and W and other residues are as described in claim 1, are effective stabilizers for organic materials, for example thermoplastic organic polymers, coating compositions or photographic materials.

6 Claims, No Drawings

U.S. PATENT DOCUMENTS

| | | | | |
|---|---|---|---|---|
| 5,106,971 | A | 4/1992 | Kletecka et al. | 544/198 |
| 5,122,593 | A | 6/1992 | Jennings et al. | 524/100 |
| 5,189,084 | A | 2/1993 | Birbaum et al. | 524/100 |
| 5,278,209 | A | 1/1994 | Kletecka et al. | 524/100 |
| 5,310,771 | A | 5/1994 | Walters | 524/100 |
| 5,521,282 | A | 5/1996 | Steinmann | 528/419 |
| 5,538,840 | A | 7/1996 | Van Toan et al. | 430/5.2 |
| 5,892,037 | A | 4/1999 | Steinmann | 544/357 |

FOREIGN PATENT DOCUMENTS

| | | |
|---|---|---|
| EP | 0443328 | 8/1991 |
| EP | 0505202 | 9/1992 |
| EP | 0577292 | 1/1994 |
| JP | 03121449 | 5/1991 |
| WO | 88/08863 | 11/1988 |
| WO | 99/14206 | 3/1999 |

* cited by examiner

OXOPIPERAZINYL DERIVATIVES AND LIGHT STABILIZED COMPOSITIONS

This is a continuation of application Ser. No. 09/241,483, filed on Feb. 1, 1999, now abandoned.

The invention relates to new compounds of the class 3,3,5,5-tetramethyl-2-oxo-1,4-piperazine, polymers thereof, the use of the novel compounds or polymers as stabilizers for organic material against harmful effects of light, oxygen and/or heat, and organic material stabilized correspondingly.

Structure and numbering of 3,3,5,5-tetramethyl-2-oxo-1,4-piperazine is as shown in the formula:

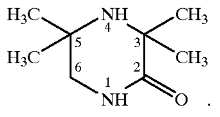

It has now been found, that certain compounds containing one or more moieties of the type 3,3,5,5-tetramethyl-2-oxo-1,4-piperazine-1-yl bonded via an oxygen atom are especially well suitable as stabilizers for organic materials.

The invention therefore relates to a compound of the formula (I)

(I)

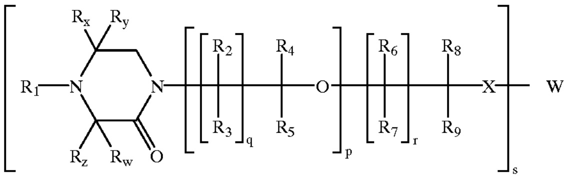

wherein p is zero or 1;

q and r, independently of each other, are an integer from 1 to 6; and s is a number ranging from 1 to 8;

X is —O— or, when p is 1, X is also a group

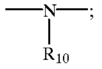

$R_w$, $R_x$, $R_y$ and $R_z$ are, independently of each other, $C_1$–$C_{18}$alkyl, $C_5$–$C_{12}$cycloalkyl or $C_1$–$C_5$hydroxyalkyl, especially methyl;

$R_1$ is hydrogen; $C_1$–$C_{18}$alkyl; oxyl; OH; $CH_2CN$; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–C15phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1C_{18}$alkanoyloxy; glycidyl; or a group —$CH_2CH(OH)$—G, in which G is hydrogen, methyl or phenyl;

$R_2$ and $R_6$, independently of each other, are hydrogen, $C_1$–$C_8$alkyl, $C_5$–$C_{12}$cycloalkyl or $C_1$–$C_4$hydroxyalkyl;

$R_3$, $R_4$, $R_5$, $R_7$, $R_8$, $R_9$, independently of each other, are hydrogen, $C_1$–$C_8$alkyl or $C_5$–$C_{12}$cycloalkyl;

when s is 1,

W is $C_1$–$C_{18}$alkyl; $C_2$–$C_{18}$alkyl which is substituted by $NH_2$, $NHR_{10}$, $N(R_{10})_2$, nitro, hydroxy and/or $OR'_{13}$; or W is $C_5$–$C_{12}$cycloalkyl; $C_5$–$C_{12}$cycloalkyl which is substituted by OH, $C_1$–$C_4$alkyl or $C_1$–$C_4$alkoxy; $C_3$–$C_6$alkenyl; $C_3$–$C_{12}$epoxyalkyl; $C_7$–$C_{15}$phenylalkyl which is unsubstituted or substituted on the phenyl ring by a radical selected from $C_1$–$C_4$alkyl and $C_1$–$C_4$alkoxy; or W is one of the groups of the formulae (IIa)–(IIe)

(IIa)

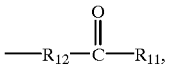

(IIb)

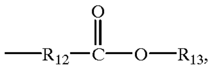

(IIc)

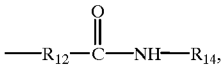

(IId)

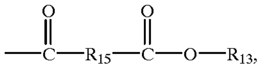

(IIe)

—$R_{12}$—CN, or, when $R_1$ is a group —$CH_2CH(OH)$—G, W may also be hydrogen;

$R_{10}$ is hydrogen, $C_1$–$C_8$alkyl, $C_5$–$C_{12}$cycloalkyl, $C_7$–$C_{15}$phenylalkyl which is unsubstituted or substituted on the phenyl ring by a radical selected from $C_1$–$C_4$alkyl and $C_1$–$C_4$alkoxy;

$R_{11}$ is hydrogen; $C_1$–$C_{17}$alkyl; $C_1$–$C_{12}$alkyl substituted by OH, $C_1$–$C_{12}$alkoxy and/or a residue benzophenonyl or benzophenonyloxy, wherein one or both phenyl rings of the benzophenone moiety are unsubstituted or substituted by OH, halogen, $C_1$–$C_4$alkyl and/or $C_1$–$C_{18}$alkoxy; or $R_{11}$ is $C_5$–$C_{12}$cycloalkyl which is unsubstituted or substituted by $C_1$–$C_4$alkyl; $C_2$–$C_{17}$alkenyl; phenyl; phenyl substituted by $NH_2$, $NHR_{10}$, $N(R_{10})_2$, or $C_1$–$C_4$alkyl or $C_1$–$C_4$alkoxy; $C_7$–$C_{15}$phenylalkyl; $C_8$–$C_{15}$phenylalkenyl; or $C_7$–$C_{15}$phenylalkyl which is substituted on the phenyl ring by $C_1$–$C_4$alkyl and/or $C_1$–$C_4$alkoxy;

$R_{12}$ is a direct bond or $C_1$–$C_{12}$alkylene; phenylene; cyclohexylene;

$R_{13}$ is $C_1$–$C_{18}$alkyl; $C_2$–$C_{18}$alkyl which is substituted by $NH_2$, $NHR_{10}$, $N(R_{10})_2$, nitro, hydroxy and/or $OR_{13}$; $C_3$–$C_{18}$alkenyl; $C_5$–$C_{12}$cycloalkyl; $C_5$–$C_{12}$cycloalkyl which is substituted by $C_1$–$C_4$alkyl and/or interrupted by —O—; and when W is a group (IId) and when W is a group (IIb) while $R_{12}$ is not a direct bond, $R_{13}$ can be also hydrogen, or one equivalent of a cation of groups Ia or IIa of the periodic system, especially sodium or potassium;

$R'_{13}$ is $C_1$–$C_{18}$alkyl; $C_2$–$C_{18}$alkyl which is substituted by $NH_2$, $NHR_{10}$, $N(R_{10})_2$, nitro, hydroxy and/or $OR_{13}$; $C_3$–$C_{18}$alkenyl; $C_5$–$C_{12}$cycloalkyl; $C_5$–$C_{12}$cycloalkyl which is substituted by $C_1$–$C_4$alkyl and/or interrupted by —O—;

$R_{14}$ is $C_1$–$C_{18}$alkyl; $C_2$–$C_{18}$alkyl which is substituted by $NH_2$, $NHR_{10}$, $N(R_{10})_2$, hydroxy and/or $OR_{13}$;

$C_5$–$C_{12}$cycloalkyl which is unsubstituted or substituted by $C_1$–$C_4$alkyl and/or interrupted by —O—; or $C_7$–$C_{15}$phenylalkyl which is unsubstituted or substituted on the phenyl ring by a radical selected from $C_1$–$C_4$alkyl and $C_1$–$C_4$alkoxy;

$R_{15}$ is a direct bond; $C_1$–$C_{20}$alkylene; $C_2$–$C_{10}$alkenylene; $C_2$–$C_8$alkenylene substituted by $C_6$–$C_{12}$aryl or $C_6$–$C_{12}$aryl which is substituted by $C_1$–$C_8$alkyl, $C_1$–$C_8$alkoxy, di($C_1$–$C_4$-alkyl)amino, nitro, thienyl, phenoxyphenyl, phenylthiophenyl, benzo[b]thiophen-2-yl, benzofuran-2-yl, 9H-fluorenyl, biphenylyl, 10H-phenothiazinyl; $C_2$–$C_4$oxaalkylene; $C_5$–$C_7$cycloalkylene; $C_5$–$C_7$cycloalkenylene or phenylene;

when s is 2

W is $C_2$–$C_{12}$alkylene; $C_4$–$C_{12}$alkylene substituted by OH and/or interrupted by oxygen or sulfur or —$NR_{10}$—; $C_4$–$C_{12}$alkenylene; $C_6$–$C_{12}$alkenylene substituted by OH and/or interrupted by O; $C_5$–$C_7$cycloalkylene; $C_5$–$C_7$cycloalkylene-di($C_1$–$C_4$alkylene); $C_1$–$C_4$alkylene-di($C_5$–$C_7$cycloalkylene); phenylene di($C_1$–$C_4$alkylene); or one of the groups of the formulae (IIIa)–(IIIh)

—CO—$R_{18}$—CO (IIIa);

—COO—$R_{19}$—OOC— (IIIb);

—CONH—$R_{20}$—NHCO— (IIIc);

(IIId)

——$(CH_2)_t$CO——;

(IIIe)

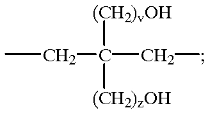

(IIIf)

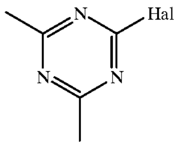

;

(IIIg)

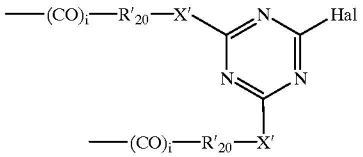

(IIIh)

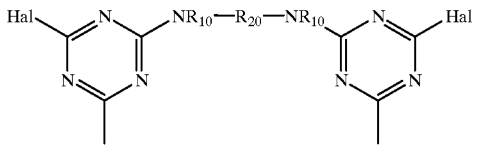

in which Hal stands for halogen or $C_1$–$C_4$alkoxy;

$R_{18}$ is a direct bond; $C_1$–$C_{12}$alkylene; $C_2$–$C_{12}$alkylene interrupted by oxygen, sulfur and/or —$NR_{10}$—; $C_5$–$C_7$cycloalkylene; $C_5$–$C_7$cycloalkenylene; or phenylene; $C_2$–$C_8$alkenylene; $C_2$–$C_8$alkenylene substituted by $C_4$–$C_{12}$aryl or $C_4$–$C_{12}$aryl which is substituted by $C_1$–$C_8$alkyl, $C_1$–$C_8$alkoxy, di($C_1$–$C_4$-alkyl)amino, nitro; or $C_2$–$C_8$alkenylene substituted by thienyl, phenoxyphenyl, phenylthiophenyl, benzo[b]thiophen-2-yl, benzofuran-2-yl, 9H-fluorenyl, biphenylyl, 10H-phenothiazinyl, thiofuranyl;

$R_{19}$ is $C_2$–$C_{12}$alkylene; $C_4$–$C_{12}$alkylene interrupted by 1, 2 or 3 oxygen atoms; $C_5$–$C_7$cycloalkylene; $C_5$–$C_7$cycloalkylene di($C_1$–$C_4$alkylene); or $C_1$–$C_4$alkylidene di($C_5$–$C_7$cycloalkylene);

$R_{20}$ is $C_2$–$C_{12}$alkylene; $C_5$–$C_7$cycloalkylene; phenylene;

$R'_{20}$ is $C_2$–$C_{12}$alkylene; $C_5$–$C_7$cycloalkylene; phenylene; and if i is 1, $R'_{20}$ additionally embraces methylene;

i is zero or 1;

t is zero or an integer from 1 to 7;

v and z, independently of each other, are an integer from 1 to 4;

when s is 3

W is aliphatic $C_4$–$C_{18}$triacyl; cycloaliphatic $C_6$–$C_{18}$triacyl or aromatic $C_9$–$C_{18}$triacyl; 1,3,5triazine-2,4,6-triyl; or a group of the formulae (IVa–IVb)

(IVa)

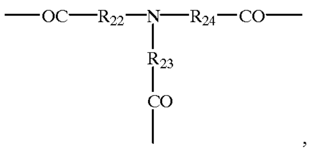

, (IVb)

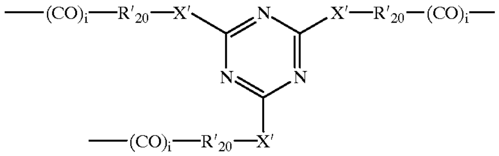

where $R_{22}$, $R_{23}$, $R_{24}$, independently of each other, are $C_1$–$C_7$alkylene;

when s is 4

W is aliphatic $C_5$–$C_{18}$tetraacyl; cycloaliphatic $C_8$–$C_{18}$tetraacyl or aromatic $C_{10}$–$C_{18}$tetraacyl or a tetravalent residue of the formula Va $Z_1$—$NR_{10}$—$R_{20}$—$NR_{10}$—$Z_2$, (Va)

wherein $Z_1$ and $Z_2$ are each, independently of one another, a group of the formula Vb, Vc or Vd (Vb)

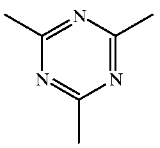

(Vc)

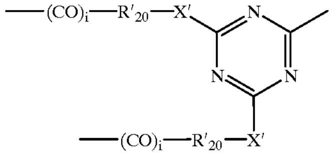

-continued (Vd)

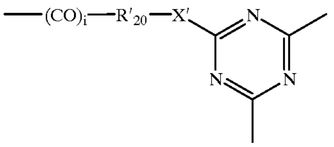

and the group of formula Vb–d is attached via a bond from the triazine ring to the nitrogen atom in formula Va;

when s is 5, W is aliphatic $C_7$–$C_{18}$pentaacyl; cycloaliphatic $C_{10}$–$C_{18}$pentaacyl or aromatic $C_{11}$–$C_{18}$pentaacyl;

when s is 6, W is aliphatic $C_8$–$C_{18}$hexaacyl; cycloaliphatic or aromatic $C_{12}$–$C_{18}$hexaacyl or a hexavalent residue of the formula VIa $$Z_1—NR_{10}—R_{20}—N(Z_2)—R_{20}—NR_{10}—Z_3 \quad (VIa)$$

wherein $Z_1$, $Z_2$ and $Z_3$, independently of one another, are a group of the formula Vb, Vc or Vd, which is attached via a bond from the triazine ring to the nitrogen atom in formula VIa;

when s is 7, W is aliphatic, cycloaliphatic or aromatic $C_{12}$–$C_{18}$heptaacyl;

when s is 8, W is aliphatic, cycloaliphatic or aromatic $C_{12}$–$C_{18}$octaacyl or a residue of the formula VIIa $$Z_1—NR_{10}—R_{20}—N(Z_2)—R_{20}—N(Z_3)—R_{20}—NR_{10}—Z_4 \quad (VIIa)$$

wherein $Z_1$, $Z_2$, $Z_3$ and $Z_4$, independently of one another, are a group of the formula Vb, Vc or Vd, which is attached via a bond from the triazine ring to the nitrogen atom in formula VIIa; and X' is —O— or —$N(R_{10})$—.

Where one compound carries more than one group denoted with the same symbol, these groups may be the same or different within their defined meanings.

W as an aliphatic, cycloaliphatic or aromatic acyl group of valency s stands for a residue R—(CO—)$_s$, where R embraces, for example, within the definition given as an aliphatic residue alkyl or alkenyl, or alkyl or alkenyl substituted by OH or $COOR_{13}$ or interrupted by O; as a cycloaliphatic residue $C_5$–$C_{12}$cycloalkyl, especially cyclohexyl, or a corresponding 5 or 6 membered oxa-cycloalkyl moiety, or said $C_5$–$C_{12}$cycloalkyl or oxa-cycloalkyl moiety substituted by $C_1$–$C_4$alkyl, OH, $C_1$–$C_4$hydroxyalkyl or $COOR_{13}$; as an aromatic residue phenyl, naphthyl or biphenyl, or phenylalkyl, phenylalkenyl, naphthylalkyl, naphthylalkenyl, biphenylalkyl, biphenylalkenyl; or said aromatic residues substituted by $COOR_{13}$.

Of special importance among these acyl residues R—(CO—)$_s$ are when s is 1, W as a group of the above formula (IIb) or (IId) or a group of the formula (II'a) or (II'c):

(II'a)

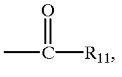

(II'c)

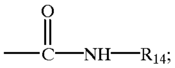

when s is 2, an acyl residue of formula IIIa with R as $R_{18}$, especially $C_1$–$C_{12}$alkylene; $C_4$–$C_{12}$alkylene;

$C_4$–$C_{12}$alkylene interrupted by oxygen, sulfur and/or —$NR_{10}$—; $C_5$–$C_7$cycloalkylene; phenylene; $C_2$–$C_8$alkenylene; $C_2$–$C_8$alkenylene substituted by phenyl or a residue thiophene, e.g.

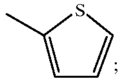
;

when s is 4, R as phenyl, $C_4$–$C_6$alkyl or $C_4$–$C_6$alkenyl or a group of the formulae (Vc–Vd)

(Vc)

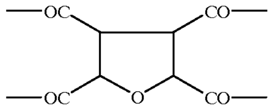

(Vd)

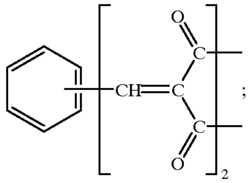
;

when s is 6, R as a 1,2,3,4,5,6-cyclohexane hexacarboxy, or a residue of the formula

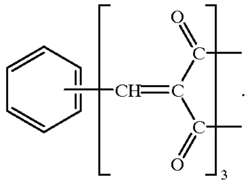
.

Preferably, s is 1, 2, 3, 4, 6 or 8; more preferably 1–4 or 6; most preferably 2–4 or 6.

Alkylene, cycloalkylene or alkenylene residues may be bonded on different carbon atoms or on the same carbon atom thus embracing alkylidene, cycloalkylidene and alkenylidene, respectively.

$R_{15}$ as $C_2$–$C_{10}$alkenylene is preferably a group

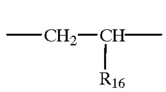

or a group

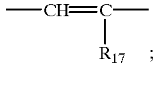
;

where $R_{16}$ is $C_3$–$C_8$alkenyl; and $R_{17}$ is hydrogen or $C_1$–$C_8$alkyl.

Halogen atoms are preferably chloro or bromo, especially chloro.

$R_1$ is preferably hydrogen; $C_1$–$C_8$alkyl, especially methyl; oxyl; OH; $C_1$–$C_{18}$alkoxy, especially $C_3$–$C_{12}$alkoxy; $C_5$–$C_{12}$cycloalkoxy, especially cyclohexyloxy; $C_3$–$C_8$alkenyl; $C_3$–$C_8$alkynyl, e.g. propargyl; $C_7$–$C_{12}$phenylalkyl, e.g. benzyl; $C_7$–$C_{15}$phenylalkoxy;

$C_1$–$C_8$alkanoyl, especially acetyl; $C_3$–$C_5$alkenoyl, especially (meth)acryloyl; glycidyl; or a group —$CH_2CH$(OH)—G, in which G is hydrogen, methyl or phenyl.

Aryl stands for an organic residue obeying the Hueckel rule, i.e. containing 4n+2 π-electrons per molecular unit, where n is an integer. Thus, $C_4$–$C_{12}$aryl usually is heteroaryl, where heteroatoms are mostly N, O or S, or hydrocarbon $C_6$–$C_{12}$aryl. $C_4$aryl groups are, for example, furanyl, thiophenyl, pyrrolyl; $C_6$–$C_{12}$aryl is, for example, phenyl or naphthyl. Especially preferred is thiophenyl or phenyl.

Groups which may be unsubstituted or substituted by selected radicals such as $C_6$–$C_{12}$aryl or $C_5$–$C_{12}$cycloalkyl, like a phenyl or a cyclohexyl ring, are preferably unsubstituted or mono-, di- or tri-substituted, especially preferred are these groups unsubstituted or mono- or disubstituted.

A preferred residue $C_3$–$C_{12}$epoxyalkyl is glycidyl.

Open bonds in alkylene or cycloalkylene residues may be attached on different carbon atoms or on the same carbon atom, thus embracing alkylidene or cycloalkylidene. Alkylidene and cycloalkylidene are saturated divalent hydrocarbons having both open bonds localized on the same carbon atom; for instance, $C_1$–$C_4$alkylidene embraces $C_1$alkylidene which is methylene.

Alkyl is a monovalent residue of the formula $C_nH_{(2n+1)}$ wherein n denotes the number of carbon atoms. Alkylene, alkanetriyl, alkanetetrayl, alkanepentayl, alkanehexayl, alkaneheptayl, alkaneoctayl are corresponding di, tri, tetra, penta, hexa, hepta or octovalent alkanes wherein each bond reduces the number of hydrogen atoms in the general formula $C_nH_{(2n+2)}$ by 1.

Alkanoyl is a branched or unbranched radical, typically, within the definitions given, formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Alkanoyl of 2 to 18, in particular of 2 to 12, e.g. of 2 to 6, carbon atoms is preferred. Acetyl is particularly preferred.

Alkanoyloxy is oxygen-capped alkanoyl; preferences are mainly as can be derived from alkanoyl above.

Alkenoyl is a branched or unbranched radical, typically embracing, within the definitions given, propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Alkenoyl of 3 to 18, preferably of 3 to 12, e.g. of 3 to 6, most preferably of 3 to 4, carbon atoms is preferred.

Alkenoyloxy is oxygen-capped alkenoyl; preferences are mainly as can be derived from alkenoyl above.

Alkyl is a branched or unbranched radical, embracing, within the definitions given, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

Alkenyl is a branched or unbranched radical, embracing, within the definitions given, vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl.

Alkyl which is interrupted by oxygen, sulfur or

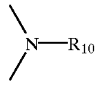

typically embraces, within the definitions given, $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—$)_2$—O—$CH_2$—, $CH_3$—(O—$CH_2CH_2$—$)_3$O—$CH_2$— or $CH_3$—(O—$CH_2CH_2$—$)_4$O—$CH_2$—.

$C_7$–$C_9$Phenylalkyl is typically benzyl, α-methylbenzyl, α,α-dimethylbenzyl or 2-phenylethyl. Benzyl and α,α-dimethylbenzyl are preferred.

$C_1$–$C_4$Alkyl-substituted phenyl preferably contains 1 to 3, in particular 1 or 2, alkyl groups is typically o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Alkoxy is a branched or unbranched radical, embracing, within the definitions given, methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Alkoxy of 1 to 12, in particular of 1 to 8, e.g. of 1 to 6, carbon atoms is preferred.

Alkylene is a branched or unbranched radical, embracing, within the definitions given, methylene, ethylene, propylene, trimethylene, tetramethylene, pentamethylene, hexamethylene, heptamethylene, octamethylene, decamethylene, dodecamethylene or octadecamethylene. $C_1$–$C_{12}$Alkylene and, in particular, $C_2$–$C_8$alkylene are preferred.

Alkylene which is interrupted by oxygen, sulfur or

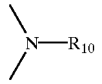

is within the definitions given, for example, —$CH_2$—O—$CH_2$—, —$CH_2$—S—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—$)_2$O—$CH_2$—, —$CH_2$—(O—$CH_2CH_2$—$)_3$O—$CH_2$—, —$CH_2$—(O—$CH_2CH_2$—$)_4$O—$CH_2$— or —$CH_2CH_2$—S—$CH_2CH_2$—.

Alkenylene, within the definitions given, is typically vinylene, vinylidene, methylvinylene, octenylethylene or dodecenylethylene.

$R_{11}$ as $C_1$–$C_{12}$alkyl substituted by a residue benzophenonyl or benzophenonyloxy, wherein one or both phenyl rings of the benzophenone moiety are unsubstituted or substituted by OH, halogen, $C_1$–$C_4$alkyl and/or $C_1$–$C_{18}$alkoxy, is preferably $C_1$–$C_{12}$alkyl substituted by a group of the formula XI, XII or XIII (XI)

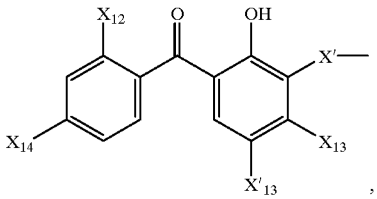

, (XII)

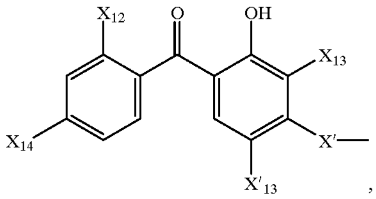

, (XIII)

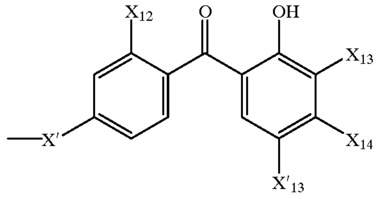

, wherein the linkage X' is a direct bond or —O—;

$X_{12}$ is H or OH;

$X_{13}$ is H, Cl, OH or $C_1$–$C_{18}$alkoxy;

$X'_{13}$ is H, Cl or $C_1$–$C_4$alkyl;

$X_{14}$ is H, Cl, OH or $C_1$–$C_{18}$alkoxy.

All residues may be straight chain or branched unless otherwise indicated. Hetero atoms are non-carbon atoms, for instance N, O, S or P atoms. Alkyl or alkylene interrupted by hetero groups such as oxygen or cycloalkylene may be interrupted by one or more of these groups as long as no linkages of the type O—O, O—N etc. occur.

The compounds of the invention can be pure or mixtures of compounds.

A preferred subject of the invention is, for example, a compound of the formula I, wherein $R_w$, $R_x$, $R_y$ and $R_z$ are, independently of each other, $C_1$–$C_8$alkyl, cyclohexyl or $C_1$–$C_5$hydroxyalkyl;

$R_1$ is hydrogen; $C_1$–$C_8$alkyl; oxyl; OH; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkoxy; $C_1$–$C_8$alkanoyl; $C_3$–$C_5$alkenoyl; glycidyl; or a group —$CH_2CH(OH)$—G, in which G is hydrogen, methyl or phenyl;

$R_2$ and $R_6$, independently of each other, are hydrogen, $C_1$–$C_8$alkyl, cyclohexyl or $C_1$–$C_4$hydroxyalkyl;

$R_3$, $R_4$, $R_5$, $R_7$, $R_8$, $R_9$, independently of each other, are hydrogen, $C_1$–$C_8$alkyl or cyclohexyl;

when s is 1,

W is $C_4$–$C_{18}$alkyl; $C_2$–$C_{18}$alkyl which is substituted by $NH_2$, $NHR_{10}$, $N(R_{10})_2$, hydroxy and/or $OR'_{13}$; or W is $C_5$–$C_{12}$cycloalkyl; cyclohexyl which is substituted by OH, $C_1$–$C_4$alkyl or $C_1$–$C_4$alkoxy; $C_3$–$C_6$alkenyl; $C_3$–$C_{12}$epoxyalkyl; $C_7$–$C_{15}$phenylalkyl which is unsubstituted or substituted on the phenyl ring by a radical selected from $C_1$–$C_4$alkyl and $C_1$–$C_4$alkoxy; or W is one of the groups of the formulae (IIa)–(IIe)

(IIa)

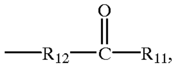

(IIb)

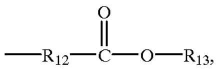

(IIc)

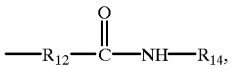

(IId)

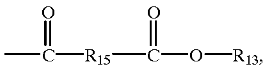

(IIe)

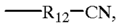

or, when $R_1$ is a group —$CH_2CH(OH)$—G, W may also be hydrogen;

$R_{10}$ is hydrogen, $C_1$–$C_8$alkyl, $C_5$–$C_{12}$cycloalkyl, $C_7$–$C_{15}$phenylalkyl;

$R_{11}$ is hydrogen; $C_1$–$C_{17}$alkyl; $C_1$–$C_{12}$alkyl substituted by OH, $C_1$–$C_{12}$alkoxy and/or a residue benzophenonyl or benzophenonyloxy, wherein one or both phenyl rings of the benzophenone moiety are unsubstituted or substituted by OH, halogen, $C_1$–$C_4$alkyl and/or $C_1$–$C_{18}$alkoxy; or $R_{11}$ is $C_5$–$C_{12}$cycloalkyl which is unsubstituted or substituted by $C_1$–$C_4$alkyl; $C_2$–$C_{17}$alkenyl; phenyl; phenyl substituted by $NH_2$, $NHR_{10}$, $N(R_{10})_2$, or $C_1$–$C_4$alkyl or $C_1$–$C_4$alkoxy; $C_7$–$C_{15}$phenylalkyl; or $C_7$–$C_{15}$phenylalkyl which is substituted on the phenyl ring by $C_1$–$C_4$alkyl and/or $C_1$–$C_4$alkoxy;

$R_{12}$ is a direct bond or $C_1$–$C_{12}$alkylene; phenylene; cyclohexylene;

$R_{13}$ is $C_1$–$C_{18}$alkyl; $C_2$–$C_{18}$alkyl which is substituted by $NH_2$, $NHR_{10}$, $N(R_{10})_2$, hydroxy and/or $OR_{13}$; $C_3$–$C_{18}$alkenyl; $C_5$–$C_{12}$cycloalkyl; cyclohexyl or oxacyclohexyl which may be substituted by $C_1$–$C_4$alkyl; and when W is a group (IId) and when W is a group (IIb) while $R_{12}$ is not a direct bond, $R_{13}$ can be also hydrogen, or one equivalent of a sodium or potassium cation;

$R'_{13}$ is $C_1$–$C_{18}$alkyl; $C_2$–$C_{18}$alkyl which is substituted by $NH_2$, $NHR_{10}$, $N(R_{10})_2$, hydroxy and/or $OR_{13}$; $C_3$–$C_{18}$alkenyl; $C_5$–$C_{12}$cycloalkyl; oxacyclohexyl; cyclohexyl which is substituted by $C_1$–$C_4$alkyl;

$R_{14}$ is $C_1$–$C_{18}$alkyl; $C_2$–$C_{18}$alkyl which is substituted by $NH_2$, $NHR_{10}$, $N(R_{10})_2$, hydroxy and/or $OR_{13}$; $C_5$–$C_{12}$cycloalkyl or oxacyclohexyl each of which is unsubstituted or substituted by $C_1$–$C_4$alkyl; or $C_7$–$C_{15}$phenylalkyl which is unsubsbtuted or substituted on the phenyl ring by a radical selected from $C_1$–$C_4$alkyl and $C_1$–$C_4$alkoxy;

$R_{15}$ is a direct bond; $C_1$–$C_{20}$alkylene; $C_2$–$C_{10}$alkenylene; $C_2$–$C_8$alkenylene substituted by $C_6$–$C_{12}$aryl or $C_6$–$C_{12}$aryl which is substituted by $C_1$–$C_8$alkyl, $C_1$–$C_8$alkoxy, di($C_1$–$C_4$-alkyl)amino, nitro, thienyl, phenoxyphenyl, phenylthiophenyl, benzo[b]thiophen-2-yl, benzofuran-2-yl, 9H-fluorenyl, biphenylyl, 10H-phenothiazinyl; $C_2$–$C_4$oxaalkylene; $C_5$–$C_7$cycloalkylene; $C_5$–$C_7$cycloalkenylene or phenylene;

when s is 2

W is $C_2$–$C_{12}$alkylene; $C_4$–$C_{12}$alkylene substituted by OH and/or interrupted by oxygen or sulfur; $C_4$–$C_{12}$alkenylene; $C_6$–$C_{12}$alkenylene substituted by OH and/or interrupted by O; $C_5$–$C_7$cycloalkylene; $C_5$-$C_7$cycloalkylene-di($C_1$-$C_4$alkylene); $C_1$–$C_4$alkylene-di($C_5$–$C_7$cycloalkylene); phenylene di($C_1$–$C_4$alkylene); or one of the groups of the formulae (IIIa)–(IIIe)

$$—CO—R_{18}—CO \quad \text{(IIIa)};$$

$$—COO—R_{19}—OOC— \quad \text{(IIIb)};$$

$$—CONH—R_{20}—NHCO— \quad \text{(IIIc)};$$

$$—(CH_2)_tCO— \quad \text{(IIId)};$$

(IIIe)

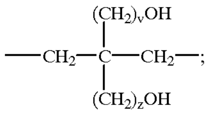

$R_{18}$ is a direct bond; $C_1$—$C_{12}$alkylene; $C_2$–$C_{12}$alkylene interrupted by oxygen, sulfur and/or —$NR_{10}$—; $C_5$–$C_7$cycloalkylene; $C_5$–$C_7$cycloalkenylene; or phenylene; $C_2$–$C_8$alkenylene; $C_2$–$C_8$alkenylene substituted by $C_4$–$C_{12}$aryl or $C_4$–$C_{12}$aryl which is substituted by $C_1$–$C_8$alkyl, $C_1$–$C_8$alkoxy, di($C_1$–$C_4$-alkyl)amino; or $C_2$–$C_8$alkenylene substituted by thienyl, phenoxyphenyl, phenylthiophenyl, benzo[b]thiophen-2-yl, benzofuran-2-yl, 9H-fluorenyl, biphenylyl, 10H-phenothiazinyl, thiofuranyl;

$R_{19}$ is $C_2$–$C_{12}$alkylene; $C_4$–$C_{12}$alkylene interrupted by 1, 2 or 3 oxygen atoms; $C_5$–$C_7$cycloalkylene; $C_5$–$C_7$cycloalkylene di($C_1$–$C_4$alkylene); or $C_1$–$C_4$alkylidene di($C_5$–$C_7$cycloalkylene);

$R_{20}$ is $C_2$–$C_{12}$alkylene; cyclohexylene; phenylene;

$R'_{20}$ is $C_2$–$C_{12}$alkylene; cyclohexylene; phenylene; and if i is 1, $R'_{20}$ additionally embraces methylene;

i is zero or 1;

t is zero or an integer from 1 to 7;

v and z, independently of each other, are an integer from 1 to 4;

when s is 3

W is aliphatic $C_4$–$C_{18}$triacyl; cycloaliphatic $C_6$–$C_{18}$triacyl or aromatic $C_9$–$C_{18}$triacyl; 1,3,5-triazine-2,4,6-triyl; or a group of the formulae (IVa–IVb)

(IVa)

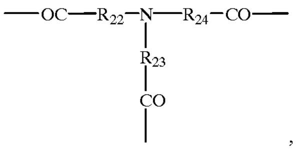

,

-continued (IVb)

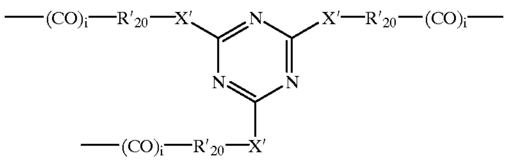

where $R_{22}$, $R_{23}$, $R_{24}$, independently of each other, are $C_1$–$C_7$alkylene;

when s is 4

W is aliphatic $C_5$–$C_{18}$tetraacyl; cycloaliphatic $C_8$–$C_{18}$tetraacyl or aromatic $C_{10}$–$C_{18}$tetraacyl or a tetravalent residue of the formula Va $$Z_1—NR_{10}—R_{20}—NR_{10}—Z_2, \quad \text{(Va)}$$

wherein $Z_1$ and $Z_2$ are each, independently of one another, a group of the formula Vb, Vc or Vd (Vb)

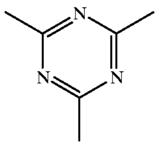

(Vc)

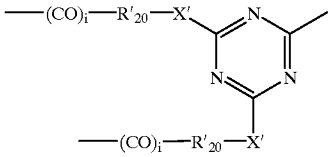

(Vd)

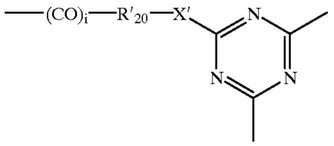

and the group of formula Vb–d is attached via a bond from the triazine ring to the nitrogen atom in formula Va;

when s is 5, W is aliphatic $C_7$–$C_{18}$pentaacyl; cycloaliphatic $C_{10}$–$C_{18}$pentaacyl or aromatic $C_{11}$–$C_{18}$pentaacyl;

when s is 6, W is aliphatic $C_8$–$C_{18}$hexaacyl; cycloaliphatic or aromatic $C_{12}$–$C_{18}$hexaacyl or a hexavalent residue of the formula VIa $$Z_1—NR_{10}—R_{20}—N(Z_2)—R_{20}—NR_{10}—Z_3 \quad \text{(VIa)}$$

wherein $Z_1$, $Z_2$ and $Z_3$, independently of one another, are a group of the formula Vb, Vc or Vd, which is attached via a bond from the triazine ring to the nitrogen atom in formula VIa;

when s is 7, W is aliphatic, cycloaliphatic or aromatic $C_{12}$–$C_{18}$heptaacyl;

when s is 8, W is aliphatic, cycloaliphatic or aromatic $C_{12}$–$C_{18}$octaacyl or a residue of the formula VIIa $$Z_1—NR_{10}—R_{20}—N(Z_2)—R_{20}—N(Z_3)—R_{20}NR_{10}—Z_4 \quad \text{(VIIa)}$$

wherein $Z_1$, $Z_2$, $Z_3$ and $Z_4$ independently of one another, are a group of the formula Vb, Vc or Vd, which is attached via a bond from the triazine ring to the nitrogen atom in formula VIIa; and X' is —O— or —N($R_{10}$)—.

Also preferred are compounds of the formula (I) wherein p is zero and X is O, thus corresponding to the formula (I')

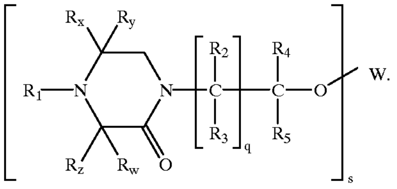

Of special importance are the compounds of formula I where p is zero or 1;

q and r, independently of each other, are an integer from 1 to 6;

s is 1,2,3,4 or 6 or 8;

$R_w$, $R_x$, $R_y$ and $R_z$ each are methyl or ethyl;

$R_1$ is hydrogen; $C_1$–$C_8$alkyl; oxyl; OH; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkoxy; $C_1$–$C_8$alkanoyl; $C_3$–$C_5$alkenoyl; glycidyl; or a group —$CH_2CH(OH)$—G, in which G is hydrogen, methyl or phenyl;

$R_2$ and $R_6$, independently of each other, are hydrogen, $C_1$–$C_8$alkyl, cyclohexyl or $C_1$–$C_4$hydroxyalkyl;

$R_3$, $R_4$, $R_5$, $R_7$, $R_8$, $R_9$, independently of each other, are hydrogen or methyl;

X is —O— or, when p is 1, X is also a group

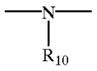

where $R_{10}$ is hydrogen, $C_1$–$C_8$alkyl, $C_5$–$C_{12}$cycloalkyl, $C_7$–$C_{15}$phenylalkyl which is unsubstituted or mono-, di- or tri-substituted or the phenyl by $C_1$–$C_4$alkyl;

when s is 1

W is $C_1$–$C_{18}$alkyl; $C_2$–$C_8$alkyl which is substituted by $NH_2$, $NHR_{10}$, $N(R_{10})_2$; $C_5$–$C_{12}$cycloalkyl; $C_3$–$C_6$alkenyl; glycidyl; $C_7$–$C_{15}$phenylalkyl which is unsubstituted or mono-, di- or tri-substituted on the phenyl ring by radicals selected from $C_1$–$C_4$alkyl and $C_1$–$C_4$alkoxy; or W is also a group of the above formula (IIb) or (IId) or a group of the formula (II'a) or (II'c):

(II'a)

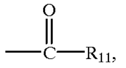

(II'c)

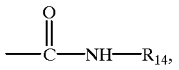

or, when $R_1$ is a group —$CH_2CH(OH)$—G, W may also be hydrogen;

$R_{11}$ is hydrogen; $C_1$–$C_{17}$alkyl; $C_5$–$C_{12}$cycloalkyl which is unsubstituted or mono-, di- or tri-substituted by $C_1$–$C_4$alkyl; $C_2$–$C_{17}$alkenyl; phenyl which is unsubstituted or substituted by $NH_2$, $NHR_{10}$, $N(R_{10})_2$ or $C_1$–$C_4$alkyl; $C_7$–$C_{15}$phenylalkyl which is unsubstituted or mono-, di- or tri-substituted on the phenyl ring by radicals selected from $C_1$–$C_4$alkyl, $C_1$–$C_4$alkoxy;

$R_{12}$ is a direct bond; $C_1$–$C_{12}$alkylene;

$R_{13}$ is $C_1$–$C_{18}$alkyl; $C_3$–$C_{18}$alkenyl; $C_5$–$C_{12}$cycloalkyl which is unsubstituted or mono-, di- or tri-substituted by $C_1$–$C_4$alkyl; and when W is a group (IId), $R_{13}$ can be also hydrogen, sodium or potassium;

$R_{14}$ is $C_1$–$C_{18}$alkyl; $C_5$–$C_{12}$cycloalkyl which is unsubstituted or mono-, di- or tri-substituted by $C_1$–$C_4$alkyl; or $C_7$–$C_{15}$phenylalkyl which is unsubstituted or mono-, di- or tri-substituted on the phenyl ring by radicals selected from $C_1$–$C_4$alkyl and $C_1$–$C_4$alkoxy;

$R_{15}$ is a direct bond; $C_1$–$C_{20}$alkylene; a group

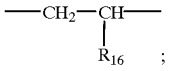

a group

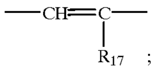

$C_2$–$C_4$oxaalkylene; $C_5$–$C_7$cycloalkylene; $C_5$–$C_7$cycloalkenylene or phenylene;

$R_{16}$ is $C_3$–$C_8$alkenyl; and $R_{17}$ is hydrogen or $C_1$–$C_8$alkyl;

when s is 2

W is $C_2$–$C_{12}$alkylene; $C_4$–$C_{12}$alkylene interrupted by 1, 2 or 3 oxygen atoms; $C_4$–$C_{12}$alkenylene; $C_5$–$C_7$cycloalkylene; $C_5$–$C_7$cycloalkylene di($C_1$–$C_4$alkylene); $C_1$–$C_4$alkylene di($C_5$–$C_7$cycloalkylene); $C_2$–$C_4$alkylidene di($C_5$–$C_7$cycloalkylene); phenylene di($C_1$–$C_4$alkylene); or one of the groups of the formulae (IIIa)–(IIIe)

—CO—$R_{18}$—CO (IIIa);

—COO—$R_{19}$—OOC— (IIIb);

—CONH—$R_{20}$—NHCO— (IIIc);

—$(CH_2)_t$CO— (IIId)

(IIIe)

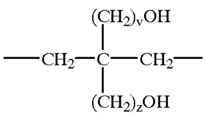

in which $R_{18}$ is a direct bond; $C_1$–$C_{12}$alkylene; $C_2$–$C_{12}$alkylene interrupted by O or S; $C_2$–$C_8$alkenylene; $C_5$–$C_7$cycloalkylene; $C_5$–$C_7$cycloalkenylene; or phenylene; or $C_2$–$C_8$alkenylene substituted by phenyl, naphthyl, thiofuranyl, or phenyl or naphthyl each of which is substituted by $C_1$–$C_4$alkyl or $C_1$–$C_4$alkoxy;

$R_{19}$ is $C_2$–$C_{12}$alkylene; $C_4$–$C_{12}$alkylene interrupted by 1, 2 or 3 oxygen atoms; $C_5$–$C_7$cycloalkylene; $C_5$–$C_7$cycloalkylene di($C_1$–$C_4$alkylene); or $C_1$–$C_4$alkylidene di($C_5$–$C_7$cycloalkylene);

$R_{20}$ and $R'_{20}$, independently, are $C_2$–$C_{12}$alkylene; $C_5$–$C_7$cycloalkylene; phenylene;

t is zero or an integer from 1 to 7;

v and z, independently of each other, are an integer from 1 to 4;

when s is 3

W is aliphatic $C_4$–$C_{18}$triacyl; aromatic $C_9$–$C_{18}$triacyl or a group of the formula (IVa) or (IVb);

when s is 4

W is aliphatic $C_6$–$C_{18}$tetraacyl; aromatic $C_{10}$–$C_{18}$tetraacyl or a group of the formula (V)

(V)

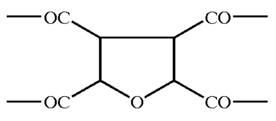

or a group of the formula (Va);

when s is 6, W is a 1,2,3,4,5,6-cyclohexane hexacarboxy residue or a group of the formula VIa (VIa)

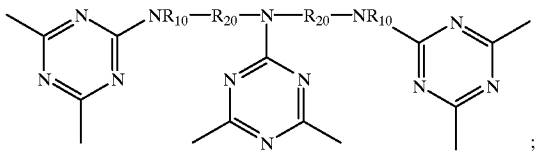

;

when s is 8, W is a residue of the formula VIIa (VIIa)

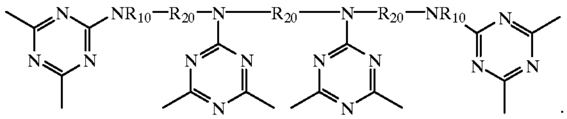

.

Other compounds of the formula I of special interest are those of the formula I"

(I")

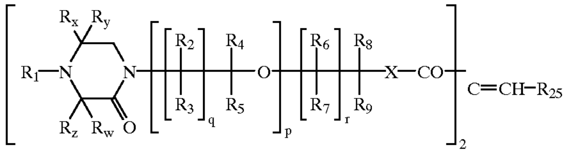

wherein $R_w$, $R_x$, $R_y$ and $R_z$ are, independently of each other, $C_1$–$C_{18}$alkyl, $C_5$–$C_{12}$cycloalkyl or $C_1$–$C_5$hydroxyalkyl, especially methyl;

$R_1$ is hydrogen; $C_1$–$C_{18}$alkyl; oxyl; OH; $CH_2CN$; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–$C_{15}$phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1$–$C_{18}$alkanoyloxy; glycidyl; or a group —$CH_2CH(OH)$—G, in which G is hydrogen, methyl or phenyl;

$R_2$, $R_3$, $R_4$, $R_5$, $R_6$, $R_7$, $R_8$, $R_9$, independently of each other, are hydrogen, $C_1$–$C_8$alkyl or $C_5$–$C_{12}$cycloalkyl;

p is zero or 1;

q and r, independently of each other, are integers from 1 to 6;

X is as defined for formula I and $R_{25}$ is phenyl which is unsubstituted or mono-, di- or tri-substituted by $C_1$–$C_8$alkyl, $C_1$–$C_8$alkoxy, di($C_1$–$C_4$-alkyl)amino, nitro; or is phenyl which is mono- or di-substituted by a group of the formula (II")

(II")

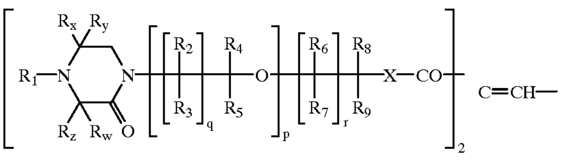

in which $R_w$, $R_x$, $R_y$, $R_z$, $R_1$, $R_2$, $R_3$, $R_4$, $R_5$, $R_6$, $R_7$, $R_8$, $R_9$, X, p, q, r are as defined above; or $R_{25}$ is naphtyl which is unsubstituted or mono-substituted by $C_1$–$C_4$alkyl, $C_1$–$C_4$alkoxy, di($C_1$–$C_4$-alkyl)amino or nitro; or $R_{25}$ is thienyl, phenoxyphenyl, phenylthiophenyl, benzothiophenyl, benzofuranyl, 9H-fluorenyl, biphenylyl, 10H-phenothiazinyl.

More preferred compounds are of the formula I'

(I')

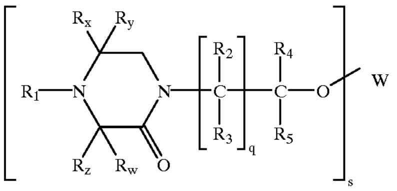

wherein q is 1 or 2; and s is a number 1, 2, 3, 4, 6 or 8;

$R_w$, $R_x$, $R_y$ and $R_z$ are, independently of each other, methyl or ethyl;

$R_1$ is hydrogen; $C_1$–$C_4$alkyl; $C_3$–$C_{12}$alkoxy; cyclohexyloxy; acetyl; $C_3$–$C_5$alkenoyl; or $R_1$ is glycidyl or a group —$CH_2CH(OH)$—G, in which G is hydrogen or methyl;

$R_2$, $R_3$, $R_4$, $R_5$ independently of each other are hydrogen or methyl;

when s is 1,

W is $C_6$–$C_{18}$alkyl; cyclohexyl; $C_2$–$C_8$alkyl which is substituted by $NH_2$, $NHR_{10}$, $N(R_{10})_2$; or W is glycidyl; or W is a group of the formula (IIa)

(IIa)

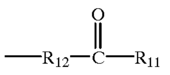

or, when $R_1$ is a group —$CH_2CH(OH)$—G, W may also be hydrogen;

$R_{10}$ is hydrogen, $C_1$–$C_8$alkyl, cyclohexyl;

$R_{11}$ is $C_1$–$C_{17}$alkyl; cyclohexyl; phenyl; phenyl substituted by $NH_2$, $NHR_{10}$, $N(R_{10})_2$;

$R_{12}$ is a direct bond;

when s is 2,

W is $C_2$–$C_{12}$alkylene; $C_4$–$C_{12}$alkylene interrupted by sulfur; or a group of the formula (IIIa):

$$CO—R_{18}—CO \quad (IIIa);$$

$R_{18}$ is $C_1$–$C_{12}$alkylene; $C_4$–$C_{12}$alkylene interrupted by O or S or $NR_{10}$; phenylene; cyclohexylene; $C_2$–$C_8$alkenylene; $C_2$–$C_8$alkenylene substituted by a group

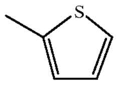

or by phenyl or naphthyl, or by phenyl or naphthyl, each of which is substituted by methyl or methoxy;

when s is 3,

W is 1,3,5-triazine-2,4,6-triyl; or a group of the formula IVb (IVb)

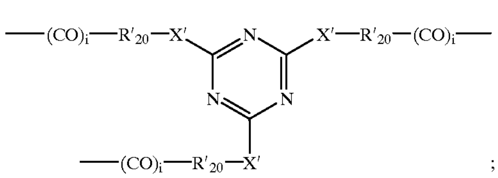

;

$R'_{20}$ is $C_2$–$C_8$alkylene or phenylene;

i is zero or 1;

when s is 4,

W is a residue of the formula Ve or Vf when s is 8,

W is a residue of the formula VIIa (VIIa)

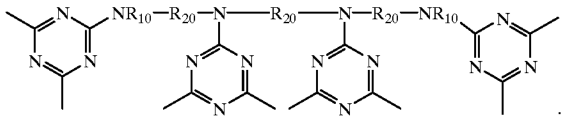

.

Some of the above compounds of the formula I are especially well suitable for the preparation of polymeric light stabilizers or for grafting them onto organic polymers having suitable functional groups. These are mainly compounds of the formula I carrying a hydroxy or epoxy group or a polymerizable ethylenic double bond.

The invention therefore also pertains to a process for grafting a compound of the formula I carrying a hydroxy or epoxy group or a polymerizable ethylenic double bond onto an onto organic polymer carrying suitable functional groups.

Compounds of the formula I suitable for grafting and carrying a hydroxy group are preferably compounds of the formula I, wherein s is 1 and W is hydroxyalkyl or hydrogen or wherein s is 1 and $R_2$ is hydroxyalkyl, or a precursor compound for compounds of the formula I such as a compound of formula IX or of examples 1–5 below. Polymers having suitable functional groups for the reaction with these hydroxy compounds are mainly organic polymers containing carboxy, anhydride or epoxy groups.

Compounds of the formula I suitable for grafting and carrying an epoxy group are preferably compounds of the formula I, wherein s is 1 and W is $C_3$–$C_{12}$epoxyalkyl, especially glycidyl. Polymers having suitable functional groups for the reaction with these epoxy compounds are (Ve)

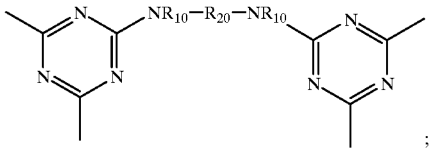

;

(Vf)

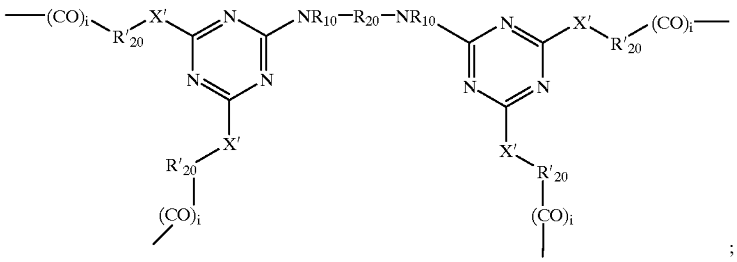

;

$R_{20}$ is $C_2$–$C_8$alkylene;

when s is 6,

W is cyclohexane hexaacyl or a residue of the formula VIa (VIa)

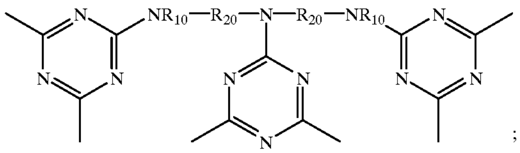

;

mainly organic polymers containing carboxy and/or hydroxy groups.

Compounds of the formula I suitable for grafting and carrying an ethylenic double bond are preferably compounds of the formula I, wherein $R_1$ is acryloyl or methacryloyl; or wherein s is 1, W is a group of the formula (IIa) with $R_{12}$ being a direct bond and $R_{11}$ being 1-alkenyl or W is a group of the formula (IId) with $R_{15}$ being alkenylene or substituted alkenylene with the ethylenic double bond vicinal to C═O; or wherein s is 2 and W is a group of the formula (IIIa) with $R_{18}$ being alkenylene or substituted alkenylene with the ethylenic double bond vicinal to C═O.

Grafting reactions can be carried out in close analogy to methods known in the art, e.g. to methods described in EP-A-526399, pages 6–16, or to methods described in U.S. Pat. No. 5,189,084, see especially column 6, line 59, until column 7, line 53, and example 1; these passages of U.S. Pat. No. 5,189,084 are hereby incorporated by reference. Polymers thus modified and containing a high amount of units of formula I or IX, e.g. 5 to 90, especially 10 to 80% by weight of the modified polymer, can be used as stabilizers for organic material in the same manner as described for compounds of the formula I.

The invention further pertains to a process for the polymerization or copolymerization of a compound of the formula I carrying an epoxy group or a polymerizable ethylenic double bond or 2 hydroxy groups within the same molecule.

(Co)polymerization reactions can be carried out in close analogy to methods known in the art, e.g. to methods described in U.S. Pat. No. 5,189,084, column 5, lines 10–52, and references cited therein, as well as example 2 of U.S. Pat. Nos. 5,189,084; 5,521,282 or 5,710,240. The cited passages of U.S. Pat. No. 5,189,084 are hereby incorporated by reference.

Compounds of the formula I suitable for polymerization and carrying an ethylenic double bond are preferably compounds of the formula 1, wherein s is 1, W is a group of the formula (IIa) with $R_{12}$ being a direct bond and $R_{11}$ being 1-alkenyl or W is a group of the formula (IId) with $R_{15}$ being alkenylene or substituted alkenylene with the ethylenic double bond vicinal to C═O; or wherein s is 2 and W is a group of the formula (IIIa) with R $_{18}$ being alkenylene or substituted alkenylene with the ethylenic double bond vicinal to C═O; or wherein s is 1 and $R_1$ is acryloyl or methacryloyl. These compounds may be reacted in close analogy to methods known in the art to obtain homopolymers or, by reacting with a further ethylenically unsaturated monomer, to obtain copolymers.

Compounds of the formula I suitable for polymerization and carrying an epoxy group are preferably compounds of the formula I, wherein s is 1 and $R_1$ is glycidyl or W is $C_3$–$C_{12}$epoxyalkyl, especially glycidyl. Preferably, these compounds are reacted to polyethers following the method described in U.S. Pat. No. 5,521,282, column 4, line 16, until column 5, line 19; this passage of U.S. Pat. No. 5,521,282 is hereby incorporated by reference.

Compounds of the formula I suitable for polymerization and 2 hydroxy groups are preferably compounds of the formula I, wherein s is 1 and two of the residues W, $R_2$ and $R_1$ contain a hydroxy group or, as it is preferred, $R_1$ is a group of formula —$CH_2CH(OH)$—G and $R_2$ is either hydroxyalkyl while W is alkyl or $R_2$ is hydrogen or alkyl and W is hydrogen.

Preferably, these compounds are reacted with a suitable derivative of a dicarboxylic acid to obtain a polyester according to methods known in the art; the reaction can, for example, follow one of the methods described in U.S. Pat. No. 5,710,240.

Preferred is a polymer containing tetramethylpiperazinone side chains and comprising from 1–100 mol % of recurring units of the formula L (L)

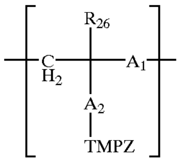

and 0–99 mol % of recurring units of the formula LI $$—(—CH_2—C(R_{27})(R_{28})—A_1—)— \quad \text{(LI)}$$

wherein

TMPZ is a tetramethylpiperazinone side chain of the formula (LII)

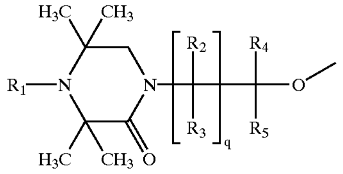

or (LIII)

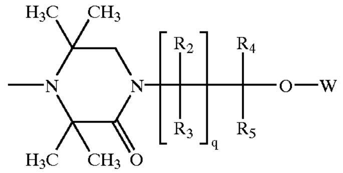

with $R_1$ being H; $C_1$–$C_4$alkyl; $C_3$–$C_{12}$alkoxy; cyclohexyloxy; acetyl; $R_2$, $R_3$, $R_4$ and $R_5$ independently being H or methyl; W being $C_1$–$C_{18}$alkyl; cyclohexyl; or a group —CO—$R_{11}$, where $R_{11}$ is $C_1$–$C_{17}$alkyl; cyclohexyl; phenyl; and q is as defined above;

$A_1$ is oxygen or a direct bond;

when $A_1$ is oxygen, $A_2$ is $CH_2$, $R_{26}$ and $R_{27}$ each are H, and $R_{28}$ is $C_1$–$C_{18}$alkyl, $C_1$–$C_{18}$alkoxy, $C_1$–$C_{12}$alkoxymethyl; $C_5$–$C_9$cycloalkyl, cyclohexyloxy, phenyl, $C_7$–$C_9$phenylalkyl, or hydrogen;

when $A_1$ is a direct bond, $A_2$ is CO, $R_{26}$ and $R_{27}$ independently are H or methyl, and $R_{28}$ is COOH, $CONH_2$, or $COOR_{29}$, where $R_{29}$ is $C_1$–$C_{12}$alkyl or $C_1$–$C_8$hydroxyalkyl.

Preferred are homopolymers consisting of recurring units of formula L.

Also preferred is a polymer comprising recurring units of the formula LIV (LIV)

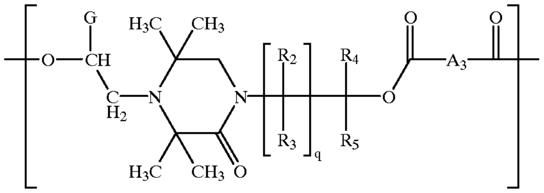

wherein $R_2$, $R_3$, $R_4$ and $R_5$ independently are H or methyl;

G is H, methyl or phenyl;

q is a number ranging from 1 to 6, preferably 1 or 2;

$A_3$ is a direct bond; $C_1$–$C_{12}$alkylene; $C_2$–$C_{12}$alkylene interrupted by S, $NR_{10}$ or O, where $R_{10}$ as defined above for formula I; cyclohexylene or phenylene; especially $C_1$–$C_{12}$alkylene or phenylene.

Polymers of formula LIV and polymers containing structural units of formula L usually have a molecular weight $M_n$ measured by gel permeation chromatography from 600 to 600000 g/mol; preferably $M_n$ is 1000–30000 g/mol, especially 1000–10000 g/mol. The polymeric compounds of the invention can be employed as stabilizers for organic material against effects of light, oxygen and/or heat in the same manner as described for the compounds of formula I.

End groups of the polymers of the invention are determined by the preparation process described; usually end groups are H, OH or $C_1$–$C_6$alkyl; in case of formula LIV, end groups may be also

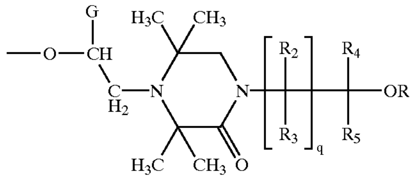

or

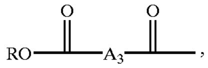

where R, independently, is H or $C_1$–$C_6$alkyl.

The preparation of compounds of the formula I can start from free alcohol precursors corresponding to formula IX (IX)

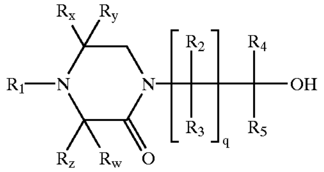

wherein $R_1$ is hydrogen or $C_1$–$C_4$alkyl and the other symbols are as defined for formula I. Some specific compounds of this class are known; prior art describes their synthesis using phase transfer catalysis and/or cyanide or cyanhydrine. In particular, suitable 1,2-diamine derivatives are reacted with a saturated ketone and a haloform reactant (represented for 2-oxo-3,3,5,5-tetramethyl piperazine compounds by acetone and chloroform respectively) in an organic solvent for the reactants (represented in the prior art mostly by methylenechloride), in the presence of aqueous alkali and ammonium salts, such as tetraalkyl ammonium halide, following the usual phase transfer catalysis (PTC) conditions (see U.S. Pat. Nos. 4,167,512, 4,190,571, 4,246,412, 4,297,492, 4,466,915, 4,698,446 and J. Lai, Synthesis 1981, 40–41).

The following useful precursor compounds embraced by the formula (IX) are new and are also subject of present invention:

1-(2-hydroxyethyl)-3,3,5,5-tetramethyl-piperazin-2-one, 1-(2-hydroxyethyl)-3,3,4,5,5-pentamethyl-piperazin-2-one, 1-(2-hydroxypropyl)-3,3,5,5-tetramethyl-piperazin-2-one, 1-(2-hydroxypropyl)-3,3,4,5,5-pentamethyl-piperazin-2-one.

The precursor compounds of the formula (IX) also can be employed as stabilizers for organic materials. Of special value is their use as stabilizers for photographic material.

Compounds of the formula (IX) may be reacted to compounds of the formula (I), e.g. wherein $R_1$ is other than hydrogen or lower alkyl and/or s is other than 1, using methods known in the art; examples for such methods are alkylation, (trans)esterification or etherification, substitution etc.

In an improved process, a 1,1-dimethyl-1,2-ethylenediamine is reacted with chloroform and acetone as described in prior art for the ketoform reaction, but acetone is used as a solvent as well as a reactant, the amount of chloroform is in slight molar excess over the amount of diamine, for example between 1 and 2 moles $CHCl_3$ per mole of diamine, and alkaline hydroxide, preferably sodiumhydroxide, is used in large excess over the diamine, e.g. 3–10 moles per mol diamine. In particular, the molar ratio $CHCl_3$:diamine:alkali hydroxide in the improved process is preferably from 1.1:1:4.4 to 1.5:1:6, thus providing an excellent regioselectivity control. The resulting regioisomer ratio of products of the type (A):(B) is typically 95:1 or higher, (A) being the desired product. Products are obtained in good yields. Alkaline hydroxide, especially sodium hydroxide, is preferably used in concentrated aqueous solution, e.g. containing 50% by weight NaOH.

By using the above mentioned conditions, an excellent regioselectivity control is obtained so that no separation is needed. As a further advantage, the reaction proceeds in one phase thus avoiding phase transfer catalysis. The reaction is carried out at temperature −20° C. to 60° C.; a temperature 0° C. to 25° C. is preferred.

Compounds thus obtained may be further derivatized by applying suitable synthetic methods known in the art, e.g. in analogy to methods described in EP-A-375612, U.S. Pat. Nos. 5,204,473, 5,004,770, and Kurumada et al., J. Polym. Sci., Poly. Chem. Ed. 23, 1477 (1985), as well as U.S. Pat. No. 5,449,776, example 8, and publications cited therein, for the modification of piperidine derivatives.

The diamine intermediates can be prepared by using a Mannich reaction among formaldehyde or paraformaldehyde, the suitable alkanolamine as a starting material and 2-nitropropane, followed by hydrogenation to reduce the nitro group to amine group in the presence of a suitable catalyst such as Raney-Ni. This reaction can be carried out according to known methods, for instance as described in U.S. Pat. No. 4,698,446 (column 10 lines 10–13) or in analogy to those methods.

All in the various steps indicated for all the reactions may be carried out in a single reactor or in the same reaction medium without isolating the intermediate compounds or may be carried out after separation and, where appropriate, purification.

Compounds of the formula (I") can be prepared by reaction of the appropriate molar amounts of a compound of the formula (III")

(III")

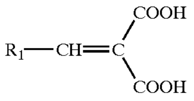

or on its derivatives such as $C_{1-C4}$alkyl diester or its acid halide, e.g. dichloride, with the appropriate molar amounts of a compound of the formula (IV")

(IV")

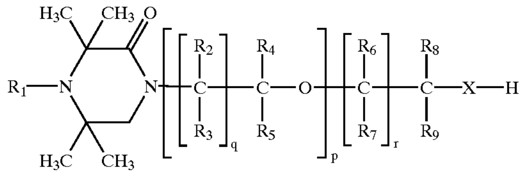

where $R_1$, $R_2$, $R_3$, $R_4$, $R_5$, $R_6$, $R_7$, $R_8$, $R_9$, X, p, q, r are as defined above, at temperature 80° C. to 200° C., preferably 120° C.–180° C. in neat or in an inert solvent such as toluene, xylene, trimethylbenzene, dimethylformamide, dimethylacetamide. Xylene is preferred.

When $C_1$–$C_4$alkyl ester derivative of the compound of the formula (III") is used, the reaction can be carried out in neat or in an inert solvent such as toluene, xylene, trimethylbenzene; xylene is preferred; preferably the reaction is carried out in the presence of a transesterification catalyst, such as alkali metals, their hydrides, amides or alcoholates, titanium (IV) alkoxide or dialkyl tin (IV) oxide; sodium alcoholate or dibutyl tin (IV) oxide being preferred.

When an acyl halide of the compound of the formula (III) is used, the reaction may be carried out in an inert solvent such as toluene, xylene, trimethylbenzene, dichloroethane; xylene being preferred; in the presence of an inorganic or organic base such as tri($C_2$–$C_4$alkyl)amines, sodium hydroxide, sodium carbonate, potassium hydroxyide, potassium carbonate, an inorganic base such as, for example, sodium hydroxide or sodium carbonate being preferred.

Compounds of the formula III" are known or may be made from known compounds by known methods or in close analogy to those methods.

Compounds of the formula IV" can be prepared according to the reaction scheme hereunder reported:

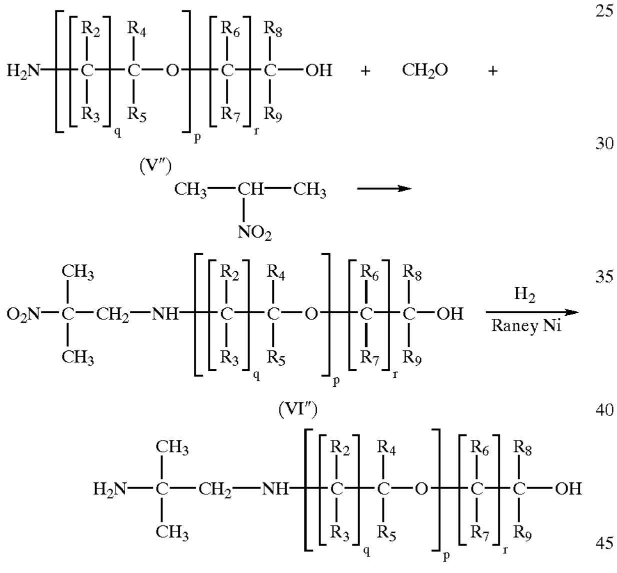

(V")

(VI")

(VI")

where $R_2$, $R_3$, $R_4$, $R_5$, $R_6$, $R_7$, $R_8$, $R_9$, p, q and r are as defined above.

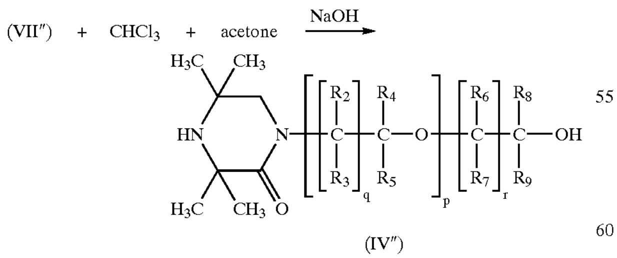

(IV")

Reaction conditions thereby are kept closely to the descriptions given in prior art or follow the improved process described above. Compounds of the formula (I") wherein X is a group —N($R_{10}$)—, where $R_{10}$ is as defined above, can be obtained in analogy to the above procedure or by processing the above product in a known manner or by applying analogous methods.

The novel compounds of present invention can be employed with advantage for stabilizing organic material against the damaging effect of light, oxygen and/or heat. They are notable for high substrate compatibility and good persistence in the substrate.

Examples of materials to be stabilized in accordance with the invention are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbonene, polyethyl ene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or τ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene-neisobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloridevinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PANPP, PA/PPO, PBT/PC/ABS or PBT/PET/PC.

The invention therefore also provides compositions comprising

A) an organic material which is sensitive to oxidative, thermal and/or actinic degradation, and B) at least one compound of the formula I, and provides for the use of compounds of the formula I for stabilizing organic material against oxidative, thermal or actinic degradation.

Effects of degradation inter alia may be discoloration, molecular breakdown or buildup.

Thus, the invention likewise embraces a method of stabilizing organic material against thermal, oxidative and/or actinic breakdown/buildup, which comprises applying or adding at least one compound of the formula I to this material.

Of particular interest is the use of compounds of the formula I as stabilizers in synthetic organic polymers, especially thermoplastic polymers, and corresponding compositions, in film forming binders for coatings and in reprographic material.

The organic materials to be protected are preferably natural, semisynthetic or, preferably, synthetic organic materials. Particular preference is given to synthetic organic polymers or mixtures of such polymers, especially thermoplastic polymers such as polyolefins, especially polyethylene and polypropylene (PP), and coating compositions. Of special importance are also polycarbonates and blends thereof, such as a blend of polycarbonate and a second polymer selected from the group consisting of the polyesters, styrenic copolymers, rubbers and vinyl chloride polymers or copolymers; further examples are the polymers listed above under items 19 and 28. The second polymer in the polycarbonate blend is preferably selected from the group consisting acrylonitrile-butadiene-stryene (ABS resin), acrylonitrile-styrene-acrylate (ASA resin), acrylonitrile-EPDM-styrene (AES resin), styrene-acrylonitrile (SAN resin), poly(ethylene terephthalate), poly (butylene terephthalate), methyl methacrylate-butadiene-styrene (MBS resin), acrylic rubber, nitrile rubber, polybutadiene, polyisoprene, poly(vinyl chloride) and ABS resin; and poly(vinyl chloride) and ASA resin; preferably ABS resin.

In general the compounds of the formula I are added to the material to be stabilized in amounts of from 0.1 to 10%, preferably from 0.01 to 5%, in particular from 0.01 to 2% (based on the material to be stabilized). Particular preference is given to the use of the novel compounds in amounts of from 0.05 to 1.5%, especially from 0.1 to 0.5%.

Incorporation into the materials can be effected, for example, by mixing in or applying the compounds of the formula I and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula I into polymers is to add them before, during or directly after the polymerization of the corresponding monomers or prior to crosslinking. In this context the compound of the formula can be added as it is or else in encapsulated form (for example in waxes, oils or polymers). In the case of addition prior to or during the polymerization, the compounds of the formula I can also act as a regulator of the chain length of the polymers (chain terminator).

The compounds of the formula I can also be added in the form of a masterbatch containing said compound in a concentration, for example, of from 2.5 to 25% by weight to the polymers that are to be stabilized.

The compounds of the formula I can judiciously be incorporated by the following methods:

as emulsion or dispersion (e.g. to latices or emulsion polymers), as a dry mixture during the mixing in of additional components or polymer mixtures, by direct introduction into the processing apparatus (e.g. extruders, internal mixers, etc), as solution or melt.

Novel polymer compositions can be employed in various forms and/or processed to give various products, for example as (to give) films, fibres, tapes, moulding compositions, profiles, or as binders for coating materials, adhesives or putties.

Other materials to be stabilized with the novel compositions are recording materials. By such materials are meant, for example, those described in Research Disclosure 1990, 31429 (pages 474–480), or in GB-A-2319523 or DE-A-19750906, page 22, line 15, until page 105, line 32, for photographic reproduction and other reprographic techniques.

Of special importance is the stabilization of non-silver reprographic materials, for example, those for pressure-sensitive copying systems, microcapsule photocopier systems, heat-sensitive copier systems and ink-jet printing.

The novel recording materials feature an unexpectedly high quality, especially in terms of their light stability.

The novel recording materials have a structure which is known per se and which corresponds to the utility. They consist of a base, for example paper or plastic film, on which one or more coatings are applied. Depending on the type of material, these coats contain the suitable components required, in the case of photographic material for example silver halide emulsions, colour couplers, dyes and the like. The material intended especially for ink-jet printing has a customary base on which there is an absorption layer suitable for ink. Uncoated paper can likewise be employed for ink-jet printing; in this case, the paper functions simultaneously as a base and has the absorbent for the ink. Suitable material for ink-jet printing is described, inter alia, in U.S. Pat. No. 5,073,448, the disclosure content of which is regarded as part of the present description.

The recording material can also be transparent, for example in the case of projection films.

The compound or compounds of the formula I can be incorprated into the material even in the course of manufacture; in papermaking, for example, by addition to the pulp. Another method of use is the spraying of the material with an aqueous solution of compound(s) of the formula I, or the addition thereof to the coating.

Coatings for transparent recording materials for projection must not contain any light-scattering particles such as pigments or fillers.

The colour-binding coatings can contain further additives, for example antioxidants, light stabilizers (including UV absorbers or hindered amine light stabilizers which are not included among the novel compounds of formula I), viscosity improvers, brighteners, biocides and/or antistats.

The coating is usually prepared as follows:

The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula I is their ease of incorporation into the coating.

As mentioned, the novel recording materials cover a broad field of use. Compounds of the formula I can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. Nos. 4,416,966; 4,483,912; 4,352,200; 4,535,050; 45,365,463; 4,551,407; 4,562,137 and 4,608,330; and also in EP-A-139479; EP-A-162664; EP-A-164931; EP-A-237024; EP-A-237025 and EP-A-260129. In all these systems the compounds of the formula I can be added to the colour-accepting layer. Alternatively, the compounds of the formula I can be added to the donor layer for protecting the colour formers against light.

The compounds of the formula I can also be employed in recording materials which are based on the principle of photopolymerization, photosoftening or the rupture of microcapsules, or when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer, the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula I. If the said protective layer is present, the compound of the formula I can also be incorporated into the protective layer.

Heat-sensitive recording materials are described, for example, in JP-A8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing, as are described, for example, in EP-A-507,734.

Compounds of the formula I can also be employed in inks, preferably for ink-jet printing, for example those as described in U.S. Pat. No. 5,098,477, the disclosure content of which is regarded as part of the present description. The invention therefore also provides an ink comprising at least one compound of the formula I as stabilizer. The ink, especially for ink-jet printing, contains preferably water. Inks contain the stabilizer of the formula I usually in a concentration of from 0.01 to 20% by weight, in particular from 0.5 to 10% by weight.

The novel photographic material can be a black and white or a colour photographic material; colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process.

In general, the compounds of the formula I are contained in the photographic material in an amount from 10 to 1000 $mg/m^2$, especially from 30 to 500 $mg/m^2$.

The compounds of the invention can be incorporated in any layer of a silver halide photographic material, however, they are preferentially incorporated in a chromogenic layer, more preferentially in a layer containing a yellow coupler. They are preferentially used in a 1% to 200% weight ratio with the coupler, more preferentially 1% to 100%. Compounds of present invention show a high efficacy as stabilizers for the dye, especially the yellow dye, in the photographic material.

Yellow couplers which can be used in the novel material are preferably compounds of the formula A (A)

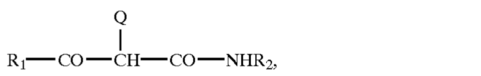

in which $R_1$ is alkyl, cycloalkyl, arylamino, anilino, a heterocyclic group or aryl, $R_2$ is aryl and Q is hydrogen or a group which can be eliminated by reaction with the oxidized developer.

The compounds of the present invention can be used in combination with other stabilisers that can be incorporated in the same layer or in a different layer. Possible stabiliser include phenolic stabilisers, conventional HALS or UV absorbers of the hydroxyphenyl benztriazole type or of the hydroxyphenyl triazine class such as described inter alia in GB-A-2319523, DE-A-19750906; see also items 1.1, 2.1, 2.6, 2.8 of the list following below. Special preference is given to a combination with a UV absorber corresponding to the formula

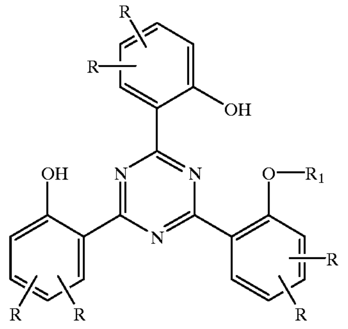

wherein $R_1$ is an organic residue, e.g. an alkyl group, and the residues R are independently of each other H or organic substituents; compounds of this class are disclosed in GB-A-2319523 and DE-A-19750906.

Details of the photographic material to be stabilized according to the invention and components which can be employed in the novel material are given, inter alia, in GB-A-2319523, DE-A-19750906, page 23, line 20, until page 105, line 32, and in U.S. Pat. No. 5,538,840, column 25, line 60, to column 106, line 31; these parts of U.S. Pat. No. 5,538,840 are incorporated herein by way of reference. Further important components, especially couplers, are described in U.S. Pat. No. 5,578,437.

In addition to the compounds of the formula I, the novel compositions may as additional component C comprise one or more conventional additives such as, for example, those indicated below.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-2-methylphenol), 4,4'-thiobis-(3,6-di-sec-amylphenol), 4,4'-bis(2,6-dimethyl-4-hydroxyphenyl)sulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl] oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis (phenylamino)propane, (o-tolyl)biguanide, bis[4-(1',3'-dimethylbutyl)phenyl]amine, tertoctylated N-phenyl-1-naphthylamine, a mixture of mono- and dialkylated tert-butyl/tertoctyldiphenylamines, a mixture of mono- and dialkylated nonydiphenylamines, a mixture of mono- and dialkylated dodecyldiphenylamines, a mixture of mono- and dialkylated isopropyl/isohexyldiphenylamines, a mixture of mono- und dialkylated tert-butydiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N'-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; $[R—CH_2CH_2—COO—CH_2CH_2\frac{}{}]_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tertbutylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9tetramethyl-2-cycloundecyl-1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl)phosphite (Irgafos®168, Ciba-Geigy), tris(nonylphenyl)phosphite, (A)

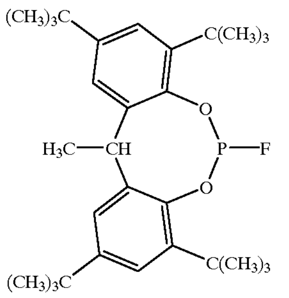

(B)

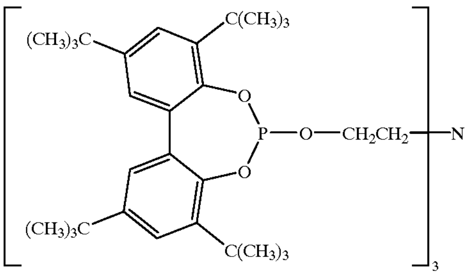

(C)

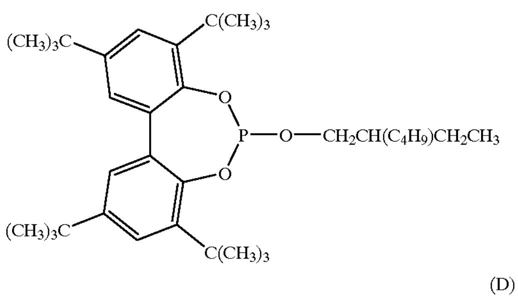

(D)

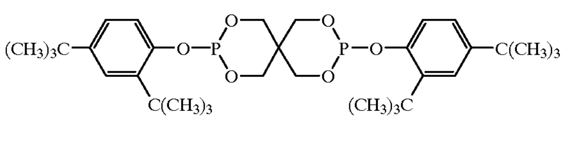

-continued (E)

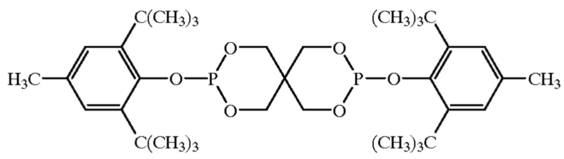

(F)

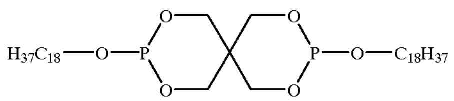

(G)

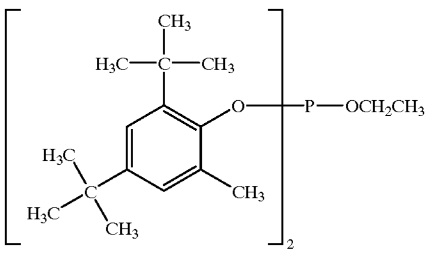

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.
6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.
7. Thiosynergists, for example, dilauryl thiodipropionate or distearyl thiodipropionate.
8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.
9. Polyamide stabilisers, for example, copper salts in combination with iodides and/or phosphorus compounds and salts of divalent manganese.
10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.
11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.
13. Other additives, for example, plasticisers, lubricants, emulsifiers, pigments, rheology additives, catalysts, flow-control agents, optical brighteners, flameproofing agents, antistatic agents and blowing agents.
14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butylbenzofuran-2-one, 3-(3,4-dimethylphenyl)-5,7-di-tert-butyl-benzofuran-2-one, 3(2,3-dimethylphenyl)-5,7-di-tert-butyl-benzofuran-2-one.

The conventional additives are judiciously employed in amounts of 0.1–10% by weight, for example 0.2–5% by weight, based on the material to be stabilized.

Costabilizers optionally to be added to the stabilizer mixture of the invention are preferably further light stabilizers, for instance those of the 2-hydroxyphenyl-benztriazole, 2-hydroxyphenyl-triazine, benzophenone or oxalanilide classes, e.g. as described in EP-A-453396, EP-A-434608, U.S. Pat. No. 5,298,067, WO 94/18278, GB-A-2297091 and WO 96/28431, and/or further hindered amines derived from 2,2,6,6-tetraalkylpiperidine containing at least one group of the formula

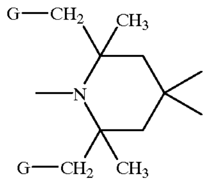

in which G is hydrogen or methyl, especially hydrogen; examples of tetraalkylpiperidine derivatives which can be used as costabilizers with mixtures of the invention are given in EP-A-356 677, pages 3–17, sections a) to f). These sections of this EP-A are regarded as part of the present description.

Especially preferred as costabilizers are 2-hydroxyphenyl-benztriazoles and/or 2-hydroxyphenyl-triazines.

The examples below illustrate the invention further. All parts or percentages, in the examples as in the remainder of the description and in the claims, are by weight, unless stated otherwise. Room temperature denotes a temperature in the range 20–30° C., unless stated otherwise. In the examples, the following abbreviations are used:

| | |
|---|---|
| % w/w | percent by weight; |
| % w/v | percent weight by volume; x % (w/v) stands for x g solid dissolved in 100 ml liquid; |
| m.p. | melting point or range; |
| GPC | gel permeation chromatography; |
| NMR | nuclear magnetic resonance (of $^1H$, if not otherwise indicated). |

Examples 1 to 5 describe the preparation of educts useful for preparing compounds of the formula I.

EXAMPLE 1

Preparation of 1-(2-hydroxyethyl)-3,3,5,5-tetramethyl-piperazin-2-one

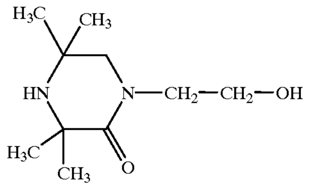

A) Preparation of 2-(2-nitro-2-methyl-propylamino)-ethanol

To a solution of 450 g (7.40 moles) of ethanolamine in 1000 ml of isopropanol, 607.8 g (6.55 moles) of 2-nitropropane and 100 ml of water are added. The solution is stirred at room temperature and 225.4 g (7.5 moles) of paraformaldehyde and 7 ml of 20% aqueous solution of sodium hydroxide (% w/v) are added, under stirring and maintaining the temperature at room temperature for 16 hours. The mixture is then heated to 50° C. being nitrogen bubbled into the mixture to eliminate the formaldehyde in excess. The mixture is then used for the reaction, without any isolation of the product.

B) Preparation of 2-(2-amino-2-methyl-propylamino)-ethanol

The mixture so obtained is transferred into an autoclave and 100 g of Ni Raney arae added. The autoclave is closed and purged with nitrogen. Hydrogen is then added until to a pressure of 50 bars. The mixture is then maintained under a pressure of 50 bars of hydrogen, at room temperature and under stirring, for 8 hours and then heated to 50° C. at the same pressure. The catalyst is then separated off by filtration and the mixture is distilled under vacuum.

A white oil is obtained (b.p. 100–105° C./13.3 mbar). N.M.R. analysis ($^1H$) conforms with the expected structure.

C) To 180 g (1.36 moles) of 2-(2-amino-2-methyl-propylamino)-ethanol in 1204 ml of acetone, 244.2 g (2.05 moles) of choroform are added.

The mixture is cooled to 5° C. under stirring and a solution of 327 g (8.18 moles) of sodium hydroxide in 327 ml of water is added slowly being the temperature of the mixture maintained at 0–5° C. during the addition.

The mixture is then stirred at 0–5° C. for further 2 hours and at room temperature for 15 hours. The pH of the aqueous solution is then corrected at 11 and the mixture is then stirred for further 4 hours.

The mixture is then filtered and the residue is washed with acetone.

The filtrate and acetone of washing are collected and evaporated under vacuum (70° C./24 mbar).

The residue is then distilled giving a white oil product (b.p. 115° C./2.66 mbar) that after some time gives a solid product (m.p. 91–93° C.).

N.M.R. analysis (300 Mhz, $CDCl_3$, δ ppm): 3.78 (t, 2H); 3.55 (t, 2H); 3.25 (s, 2H); 1.35 (s, 6H); 1.18 (s, 6H).

| Elemental analysis: | | | |
|---|---|---|---|
| Calculated: | C = 59.96%; | H = 10.07%; | N = 13.99% |
| Found: | C = 59.93%; | H = 10.05%; | N = 13.96% |

EXAMPLE 2

Preparation of 1-(2-hydroxyethyl)-3,3,4,5,5-pentamethyl-piperazin-2-one

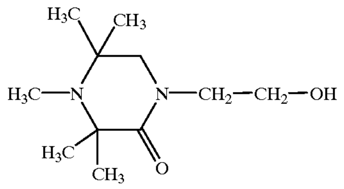

To a solution of 120 g (0.6 moles) of 1-(2-hydroxyethyl)-3,3,5,5-tetramethyl-piperazin-2-one in 300 ml of tert-amyl alcohol, 24.3 g (0.78 moles) of paraformaldehyde are added. The mixture is then heated to 80° C. and 35.8 g (0.78 moles) of formic acid dissolved in 30 ml of tert-amyl alcohol are then added slowly. The mixture is then maintained at 80° C. for further 1 hour and cooled to 50° C.

250 ml of toluene and 100 ml of water are added. The mixture is then stirred and 33 g (0.825 moles) of sodium hydroxide dissolved in 60 ml of water are added slowly.

The organic phase is then separated, washed with water, dried over anhydrous sodium sulfate, filtered and evaporated under vacuum (60° C./10 mbar).

A white solid is obtained m.p. 77–800C.

NMR analysis (300 Mhz, $CDCl_3$, δ ppm): 3.69 (t, 2H); 3.45 (t, 2H); 3.09 (s, 2H); 2.17 (s, 3H); 1.25 (s, 6H), 1.02 (s, 6H).

| Elemental analysis: | | | |
|---|---|---|---|
| Calculated | C: 61.65%; | H: 10.35%; | N: 13.07% |
| Found | C: 61.62%; | H: 10.33%; | N: 13.04% |

EXAMPLE 3

Preparation of 1-(2-hydroxypropyl)-3,3,5,5-tetramethyl-piperazin-2-one

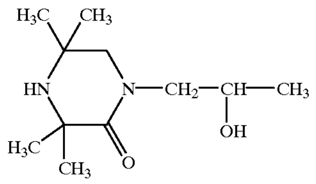

A) Preparation of 1-(2-Nitro-2-methyl-propylamino)-propan-2-ol.

Following the procedure described in Example 1A. 526.3 g (6.66 moles) of 1-amino-2-propanol 95% are reacted with 561.6 g (6.05 moles) of 2-nitropropane 96% and 181.7 g (6.05 moles) of paraformaldehyde in 100 ml of isopropanol, to give the product that has been used in the mixture without any isolation for the next reaction.

B) Preparation of 1-(2-amino-2-methylpropylamino)-propan-2-ol.

Following the procedure described in Example 1B, the previous mixture is hydrogenated by using.

100 g of Ni Raney as a catalyst.

A white oil is obtained (bp 116–120° C./13.3 mbar).

N.M.R. analysis ($^1H$) conforms with the expected structure.

C) Following the procedure described in Example 1C, 250 g (1.71 moles) of 1-(2-amino-2-methylpropylamino) propan2-ol are reacted with 306.2 g (2.57 moles) of chloroform and 1509 ml of acetone in the presence of 410.4 g (10.26 moles) of sodium hydroxide in 410 ml of water.

A yellowish oil is obtained b.p. 137–140° C./1.1 mbar.

N.M.R. analysis (300 Mhz, $CDCl_3$, δ ppm): 3.89 (m, 1H); 3.33÷3.16 (m, 4H); 1.23 (s, 6H); 1.06 (s, 6H).

| Elemental analysis: | | | |
|---|---|---|---|
| Calculated: | C = 61.65%; | H = 10.35%; | N = 13.07% |
| Found: | C = 61.58%; | H = 10.36%; | N = 13.02% |

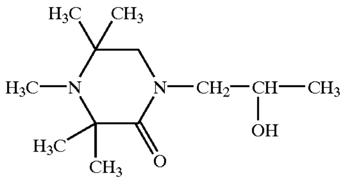

EXAMPLE 4

Preparation of 1-(2-hydroxypropyl)-3,3,4,5,5-pentamethyl-piperazin-2-one

Following the procedure described in Example 2, 149.8 g (0.7 moles) of 1-(2-hdroxypropyl)-3,3,5,5-tetramethyl-piperazin-2-one are reacted with 31.5 g (1.05 moles) of paraformaldehyde and 48.4 g (1.05 moles) of formic acid in 150 ml of t-amyl alcohol.

A white oil is obtained b.p. 117–119° C./0.27 mbar.

NMR analysis (300 Mhz, $CDCl_3$, δ ppm): 3.93 (m, 1 H), 3.47÷3.03 (m, 4H); 2.18 (s, 3H); 1.26 (s, 6H); 1.25 (s, 3H), 1.20 (t, 3H); 1.03 (s, 3H); 1.02 (s, 3H).

| Elemental analysis: | | | |
|---|---|---|---|
| Calculated: | C = 63.12%; | H = 10.60%; | N = 12.27% |
| Found: | C = 63.06%; | H = 10.59%; | N = 12.23% |

EXAMPLE 5

Preparation of 1-(2-hydroxy-1,1-dimethyl-ethyl)-3,3,5,5-tetramethyl-piperazin-2-one

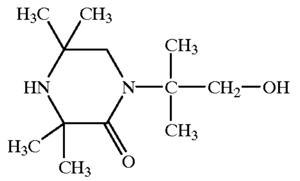

Following the procedure described in Example 1C, 80 g (0.5 moles) of 2-(2-amino-2-methyl-propylamino)-2-methyl-propan-1-ol are reacted with 90 g (0.75 moles) of chloroform and 444 ml of acetone in the presence of 114 g (2.85 moles) of sodium hydroxide in 114 ml of water.

A white oil is obtained b.p. 144–146° C./2.7 mbar.

NMR analyis (300 Mhz, $CDCl_3$, δ ppm): 3.58 (s, 2H); 3.08 (s, 2H); 1.20 (s, 6H); 1.16 (s, 6H); 1.02 (s, 6H).

| Elemental analysis: | | | |
|---|---|---|---|
| Calculated: | C = 63.12%; | H = 10.60%; | N = 12.27% |
| Found: | C = 63.04%; | H = 10.54%; | N = 12.23% |

EXAMPLE 6

Prepration of 3-[2-(3,3,5,5-tetramethyl-2-oxo-piperazin-1-yl)-ethoxy]-propylamine

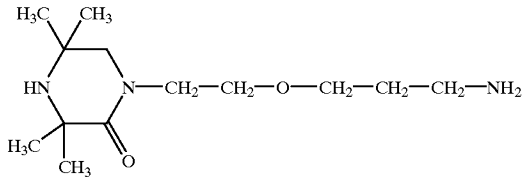

A) Preparation of 3-[2-(3,3,5,5-tetramethyl-2-oxo-piperazin-1-yl)-ethoxy]-propionitrile.

200 g (0.1 mole) of 1-(2-hydroxyethyl)-3,3,5,5-tetramethyl-piperazin-2-one are suspended in 200 g (3.78 moles) of acrylonitrile.

The mixture is cooled to 5° C. and 5 ml of 33% aqueous solution of sodium hydroxide (% w/w) are added, being the temperature maintained at 5° C. during the addition.

The mixture is then stirred at 20° C. for 4 hours.

600 ml of dichoromethane are then added and pH value corrected by using 4 ml of glacial acetic acid.

The mixture is then filtered and the organic phase is evaporated under vacuum (40° C./24 mbar). The residue is distilled giving a white oil b.p. 170–172/2.7 mbar.

B) 215.9 g (0.85 moles) of 3-[2-(3,3,5,5-tetramethyl-2-oxo-piperazin-1-yl)-ethoxy]-propionitrile are dissolved in 900 m of methanol and hydrogenated at 120° C. and at 50 bars in the presence of 100 g of Ni Raney as catalyst. The mixture is then filtered and the organic phase is evaporated under vacuum (40° C./1 0 mbar). The residue is distilled giving a white oil b.p. 130–136OC./0.8 mbar.

N.M.R. (300 Mhz, $CDCl_3$, δ ppm): 3.43 (m, 6H); 3.21 (s, 2H); 2.67 (m, 2H); 1.51 (m, 2H); 1.29 (broad, 6H); 1.10 (broad, 6H).

EXAMPLE 7

Preparation of 3,3,5,5-tetramethyl-1-[2-(oxiran-2-yl-methoxy)-ethyl]-piperazin-2-one

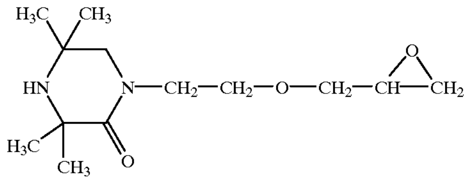

100.1 g (0.5 moles) of 1-(2-hydroxyethyl)-3,3,5,5-tetramethyl-piperazin-2-one are added to 236 g (2.55 moles) of epichlorhydrin. The mixture is then stirred at room temperature and 20 g (59 mmoles) of tetrabutylammonium hydrogen sulfate are added.

After stirring at room temperature for 1 hour, a solution of 40 g (0.1 mole) of sodium hydroxide in 80 ml of water is added slowly, being the temperature maintained at room temperature. The mixture is then stirred for 12 hours at 50° C. After cooling to room temperature, the mixture is added with 300 ml of dichlormethane and 200 ml of water. The aqueous phase is separated off and the organic phase is washed once with 100 ml of an aqueous solution 10% of NaOH (% w/w) and twice with 100 ml of water.

The organic phase is then dried over anhydrous sodium sulfate, filtered and evaporated in vacuum (30° C./24 mbar).

The oil residue is then distilled at 150° C./4 mbar. An oil product is obtained.

N.M.R: analysis (300 Mhz, $CDCl_3$, δ ppm): 3.57 (m, 6H); 3.21 (s, 2H); 2.93 (m, 1H); 2.68 (m, 1H); 2.47 (m, 1H); 1.24 (s, 6H); 1.07 (s, 6H).

EXAMPLE 8

Preparation of 3,3,4,5,5-pentamethyl-1-[2-(oxirane-2-yl-methoxy)-ethyl]-piperazin-2-one

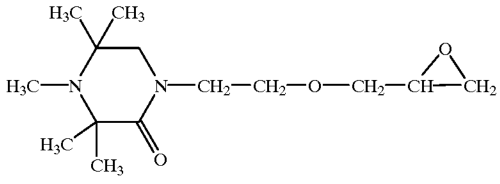

Following the procedure described in Example 7, 80 g (0.37 moles) of 1-(2-hydroxyethyl)-3,3,4,5,5-pentamethyl-piperazin-2-one are reacted with 118 g (1.28 moles) of epichlorohydrin in the presence of 13 g (38 mmoles of tetrabutylammonium hydrogen sulfate and 16.4 g (0.41 moles) of sodiumhydroxide dissolved in 41 ml of water.

An oil product is obtained.

N.M.R. analysis (300 Mhz, $CDCl_3$, δ ppm): 3.50 (m, 4H); 3.14 (s, 2H); 3.02 (m, 1H); 2.81 (m, 1H); 2.57 (m, 1H); 2.18 (s, 3H); 1.25 (s, 6H); 1.02 (s, 6H).

EXAMPLE 9

Preparation of 1,4bis-(2-hydroxyethyl)-3,3,5,5-tetramethyl-piperazin-2-one

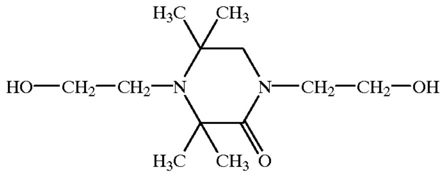

45.3 g (0.22 moles) of 1-(2-hydroxyethy)-3,3,5,5-tetramethyl-piperazin-2-one are dissolved in 450 ml of methanol in the presence of 2 ml of HCl 37% (% wiw). The solution is poured into an autoclave and 19.4 g (0.44 moles) of ethylene oxide are added. The solution is heated to 130° C. and maintained at 130° C. for 60 hours under stirring.

The solution is then cooled to room temperature and the solvent is evaporated off under vacuum (50° C./1.3 mbar).

A solid product is obtained with m.p. <200C.

N.M.R. analysis (300 Mhz, $CDCl_3$, δ ppm): 3.76 (m, 4H); 3.65 (m, 2H); 3.56 (s, 2H); 2.81 (t, 2H); 1.35 (s, 6H); 1.42 (s, 6H).

| Elemental analysis: | | | |
|---|---|---|---|
| Calculated: | C = 58.99%; | H = 9.90%; | N = 11.46% |
| Found: | C = 58.94%; | H = 9.88%; | N = 11.43% |

EXAMPLE 10

Preparation of the Compound of the Formula

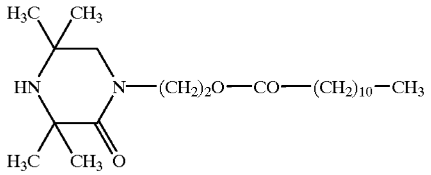

A solution of 37.6 g (188 mmoles) of 1-(2-hydroxyethyl)-3,3,5,5-tetramethyl-piperazin-2-one, 33.6 g (157 mmoles) of methyllaurate in 300 ml of xylene is heated.

| Elemental analysis: | | | |
|---|---|---|---|
| Calculated: | C = 69.06%; | H = 11.06%; | N = 7.32% |
| Found: | C = 66.82%; | H = 10.78%; | N = 7.22% |

N.M.R. analysis (300 Mhz, $CDCl_3$, δ ppm): 4.16 (t, 2H); 3.54 (t, 2H); 3.20 (s, 2H); 2.20 (t, 2H); 1.50 (m, 4H); 1.27 (s, 6H); 1.16 (m, 15H); 1.11 (s, 6H); 0.79 (t, 3H).

EXAMPLE 11

Preparation of the Compound of the Formula

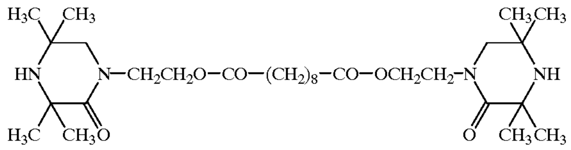

Following the procedure described in Example 10, 77.6 g (389 mmoles) of 1-(2-hydroxyethyl)-3,3,5,5-tetramethyl-piperazin-2-one are reacted with 40.6 g (176 mmoles) of dimethyl sebacate in 250 ml of xylene and in the presence of 0.2 g of dibutyl tin (IV) oxide.

An oil product is obtained.

N.M.R. analysis (300 Mhz, $CDCl_3$, δ ppm): 4.12 (t, 2H); 3.57 (t, 2H); 3.25 (s, 2H); 2.23 (t, 2H); 1.55 (m, 2H); 1.32 (s, 6H); 1.25 (bs, 4H); 1.15 (s, 6H).

| Elemental analysis: | | | |
|---|---|---|---|
| Calculated: | C = 63.57%; | H = 9.60%; | N = 9.88% |
| Found: | C = 62.98%; | H = 9.48%; | N = 9.79% |

EXAMPLE 12

Preparation of the Compound of the Formula

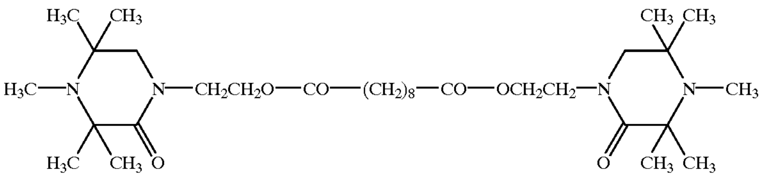

Following the procedure described in Example 10. 83.2 g (389 mmoles) of 1-(2-hydroxyethyl)-3,3,4,5,5-pentamethyl-piperazin-2-one are reacted with 40.6 g (176 mmoles) of dimethylsebacate in 250 ml of xylene and in the presence of 0.2 g of dibutyl tin (IV) oxide.

An oil product is obtained to reflux for 3 hours, being the possible residual water distilled off by azeotropation.

The solution is then cooled to room temperature and added with 0.1 g of dibutyl tin (IV) oxide.

The mixture is then heated to reflux for 24 hours, being the alcohol formed during the reaction eliminated off.

The mixture is then cooled to room temperature and the solvent is evaporated under vacuum (50° C./1.3 mbar). The residue is dissolved in 250 ml of dichloromethane and the solution is washed three times with 100 ml of water. The organic solution is then dried on anhydrous sodium sulfate, filtered and evaporated under vacuum (40° C./1.3 mbar).

An oil product is obtained.

N.M.R. Analysis (300 Mhz, $CDCl_3$, δ ppm): 4.12 (t, 2H); 3.51 (t, 2H); 3.05 (s, 2H); 2.17 (t, 2H); 2.14 (s, 3H); 1.50 (m, 2H); 1.20 (s, 6H); 1.18 (m, 4H); 0.98 (s, 6H).

| Elemental analysis: | | | |
|---|---|---|---|
| Calculated: | C = 64.61%; | H = 9.83%; | N = 9.42% |
| Found: | C = 64.14%; | H = 9.74%; | N = 9.34% |

EXAMPLE 13

Preparation of the Compound of the Formula

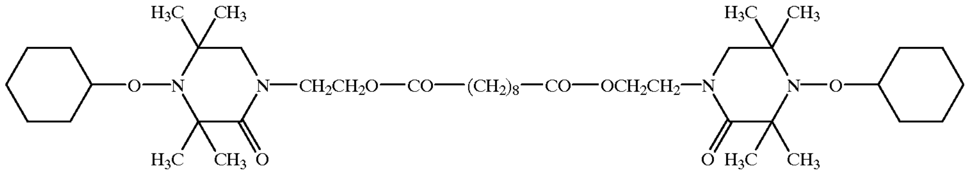

A mixture of 35 g (62 mmoles) of the compound from Example 11 in 250 ml of cyclohexane, is added with 0.25 g of $MoO_3$. The mixture is then heated to reflux and 63.6 g of a solution 70% of tert-butyl hydroperoxide (% w/w) in water (0.49 moles of tert-butyl hydroperoxide) is added slowly.

The mixture is then heated at reflux for 30 hours, being the water and tert-butyl alcohol formed during the reaction distilled off by azeotropation.

The mixture is then cooled to room temperature and filtered.

The solution is then washed with 100 ml of 10% aqueous solution of sodium sulfite (% w/v) and twice with water.

The solution is then dried over anhydrous sodium sulfate, filtered and evaporated under vacuum (50° C./1.3 mbar).

An oil yellowish product is obtained.

N.M.R. analysis (300 Mhz, $CDCl_3$, δ ppm): 4.18 (m, 1H); 3.47 (m, 2H); 2.23 (t, 2H); 2.04 (m, 2H); 1.88 (m, 2H); 1.57 (m, 2H); 1.42÷0.38 (m, 24H).

EXAMPLE 14

Preparation of the Compound of the Formula

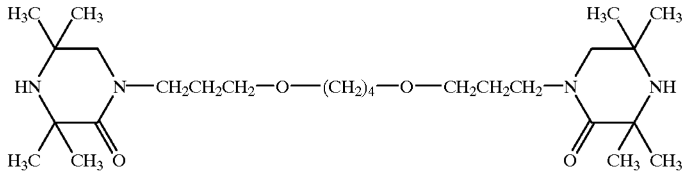

A) Prepration of 1,12-bis(2-nitro-2-methyl propyl)-4,9-dioxadodecane-1,12-diamine.

Following the procedure described in Example 1A) 100 g (0,475 moles) of 4,9-dioxadodecane-1,12-diamine are reacted with 92.6 g (0.998 moles) of 2-nitro propane (title 96%) and 32.6 g (1.1 moles) of paraformaldehyde in 340 ml of isopropanol and in the presence of 1.5 ml of 20% aqueous solution of NaOH (% w/v).

The mixture is then used for the next reaction without any isolation of the product.

B) Preparation of 1,12-bis(2-amino-2-methyl propyl)-4,9-dioxadocecane-1,12-diamine. Following the procedure described in Example 1B), the previous mixture is reacted with hydrogen in the presence of 30 g of Ni Raney at a pressure of 50 bars.

After elimination of the solvent a white oil is obtained.

N.M.R. analysis ($^1H$) conforms with the expected structure.

C) Following the procedure described in Example 1C), 80 g (0.23 moles) of 1,12-bis(2-amino-2-methyl propyl)-4,9-dioxadodecane-1,12-diamine are reacted with 82.4 g (0.69 moles) of chloroform and with 319.6 g (5.51 moles) of acetone in the presence of a solution of 110.4 g (2.76 moles) of sodium hydroxide in 110.4 ml of water.

At the end of the reaction, the mixture is filtered and the residue is washed with acetone.

The filtrate and acetone of washing are collected and evaporated under vacuum (70° C./24 mbar). The residue is taken up with 500 ml of dichloromethane and washed twice with water, once with 48 ml of HCl 1 N and twice with 50 ml of 10% aqueous solution of $K_2CO_3$ (% w/v).

The organic phase is dried over anhydrous sodium sulfate, filtered and evaporated under vacuum (70° C./24 mbar).

A yellow oil product is obtained.

N.M.R. analysis (300 Mhz, $CDCl_3$, δ ppm): 3.46 (m, 6H); 3.2 (m, 2H); 1.83 (m, 2H); 1.62 (m, 2H); 1.38 (s, 6H); 1.19 (s, 6H).

| Elemental analysis: | |
|---|---|
| Calculated: | C = 64.69%; H = 10.44%; N = 11.61% |
| Found: | C = 63.78%; H = 10.28%; N = 11.54% |

EXAMPLE 15

Preparation of the Compound of the Formula

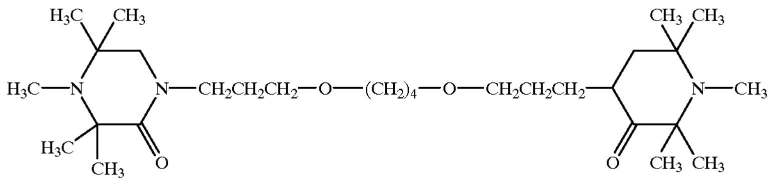

To a solution of 22 g (46 mmoles) of the compound from Example 14 in 50 ml of tert-amyl alcohol, 3.6 g (119 mmoles) of paraformaldehyde are added. The mixture is heated to 80° C. and 5.4 g (119 mmoles) of formic acid dissolved in 10 ml of tert-amyl alcohol are added slowly. The mixture is then stirred 3 hours at 80° C. 100 ml of toluene are then added, being the temperature cooled down to room temperature. A solution of 5.2 g (130 mmoles) of sodium hydroxide in 50 ml of water is then added slowly. After stirring for ½ hour, the organic phase is separated, washed twice with water dried over anhydrous sodium sulfate, filtered and evaporated under vacuum (80° C./1.3 mbar).

A yellow oil product is obtained.

N.M.R. analysis (300 Mhz, $CDCl_3$, δ ppm): 3.39 (m, 6H); 3.05 (s, 2H); 2.20 (s, 3H); 1.78 (m, 2H); 1.58 (m, 2H).

| Elemental analysis: | |
|---|---|
| Calculated: | C = 65.84%; H = 10.66%; N = 10.97% |
| Found: | C = 65.05%; H = 10.54%; N = 11.02% |

EXAMPLE 16

A mixture of 165.1 g (0.418 mol) of p-aminoethylbenzoate, 100 g (0.0500 mol) of 1-(2-hydroxy-ethyl)-3,3,5,5-tetramethyl-piperazin-2-one in 200 ml of xylene is heated to reflux; water is distilled off by azeotropation. The mixture is then cooled down to 90° C. and 0.15 g (0.008 mol) of lithiumamide are added. The mixture is then heated to reflux; xylene and ethanol formed during the reaction being partially distilled off. After 20 hours of reaction, the mixture is cooled to 20–25° C. and 500 ml of methylenchloride are added. The organic solution is then washed three times with 100 ml of water, dried on anhydrous sodium sulfate, filtered and evaporated under vacuum (70° C./24mbar). A pale yellow powder is obtained of m.p. 140° C.

1H- and 13C-NMR confirm the expected structure:

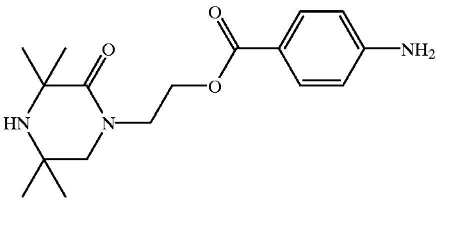

EXAMPLE 17

Following the procedure in example 16, 25 g (0.036 mol) of cyclohexane-1,2,3,4,5,6-hexabutylcarboxylate is reacted with 62 g (0.292 mol) of 1-(2-hydroxy-ethyl)-3,3,5,5-tetramethyl-piperazin-2-one. The product of the formula

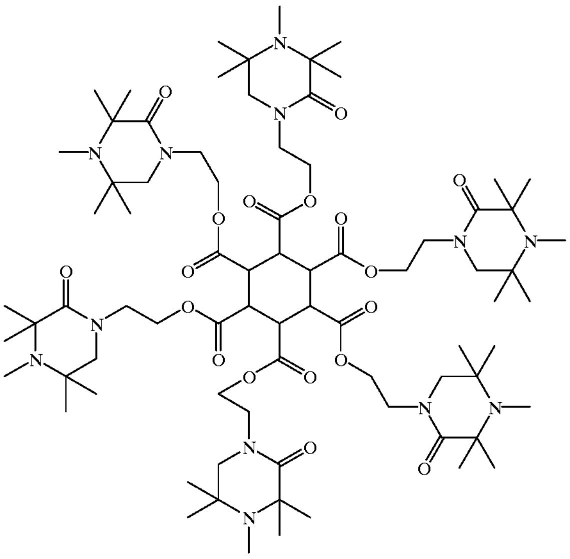

is obtained as brown resin.

$^1H$ NMR: 4.40–3.82 (m, 12H); 3.62–3.45 (m, 12H); 3.17 (s, 12H); 2.23 (s, 18H); 1.29 (s, 36H); 1.07 (s, 36H) confirms the expected structure.

EXAMPLE 21

Preparation of the Compound of the Formula

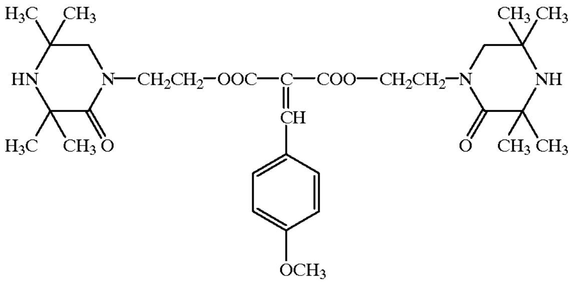

A mixture of 20 g (80 mmoles) of 2-(4-methoxy-benzylidene)-malonic acid diethyl ester, 37 g (185 mmoles) of 1-(2-hydroxy-ethyl)-3,3,5,5-tetramethyl-piperazin-2-one in 150 ml of xylene is heated to reflux being the possible water distilled off by azeotropation.

The mixture is then cooled down to 90° C. and 0.2 g (0.8 mmoles) of dibutyl tin (IV) oxide is added. The mixture is then heated to reflux being partial xylene and ethanol formed during the reaction distilled off.

The mixture is then cooled to 60° C. and 80 ml of fresh xylene is added.

The organic solution is then washed three times with 50 ml of water, dried on anhydrous sodium sulfate, filtered and evaporated in vacuo (80° C./1 mbar).

A waxy solid whose NMR ($^1H$, 300 Mhz) analysis conforms with the indicated structure, is obtained. $^1H$ NMR: 7.67 (s, 1H); 7.38 (d, 2H); 6.87(d, 2H); 4.50–4.28 (m, 4H); 3.79 (s, 3H); 3.67 (t, 2H); 3.57 (t, 2H); 3.27 (s, 2H); 3.04 (s, 2H); 1.31 (s, 6H); 1.25 (s, 6H); 1.16 (s, 6H); 0.98 (s, 6H).

EXAMPLE 22

Preparation of the Compound of the Formula

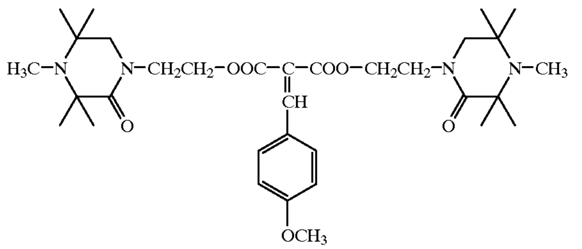

Following the procedure of Example 21, 20 g (80 mmoles) of 2-(4-methoxy-benzylidene)-malonic acid diethyl ester are reacted with 39.6 g (185 mmoles) of 1-(2-hydroxy ethyl)-3,3,4,5,5,-pentamethyl-piperazin-2-one in 150 ml of xylene.

After washing with water and evaporation of the solvent in vacuo (80° C./1 mbar), a viscous pale oil whose NMR ($^1H$, 300 Mhz) conforms with the indicated structure.

$^1H$ NMR: 7.67 (s,1H); 7.38 (d,2H); 6.87 (d, 2H); 4.40–4.24 (m, 4H); 3.76 (s, 3H); 3.63 (t, 2H); 3.52 (t, 2H); 3.11 (s, 2H); 2.92 (s, 2H); 2.18 (s, 3H); 2.13 (s, 2H); 1.27 (s, 6H); 1.21 (s, 6H); 1.03 (s, 6H); 0.88 (s, 6H).

EXAMPLE 25a)

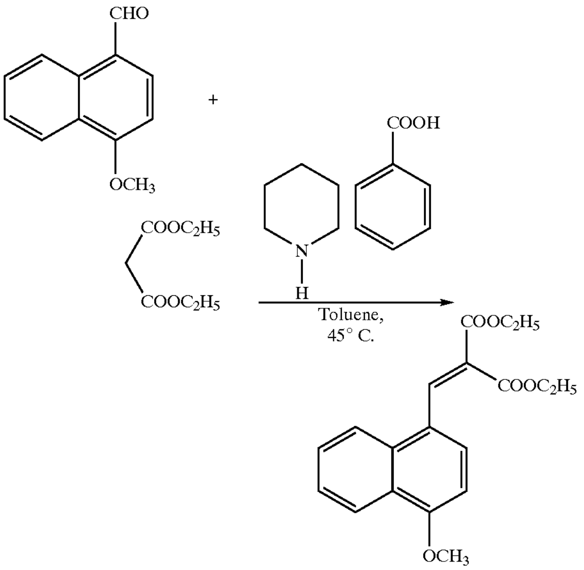

| Reactant | mmol | MW | g | ml |
|---|---|---|---|---|
| 4-methoxy-1-naphthaldehyde | 64 | 186.21 | 12 | — |
| diethylmalonate | 96 | 160.17 | 15.6 | 3.7 |
| piperidine | 20 | 85.15 | 1.96 | 2.28 |
| benzoic acid | 3.6 | 122.12 | 0.48 | — |

The reactants are mixed in a 500 ml round-bottomed flask with toluene as solvent (50 ml) and heated in an oil-bath at 45° C. for 24 hours.

After a partial removal of the reaction solvent by distillation under reduced pressure, the product is obtained as a yellow solid (m.p.=72–75° C.) from a mixture of hexane and diethyl ether (1:1).

EXAMPLE 25b)

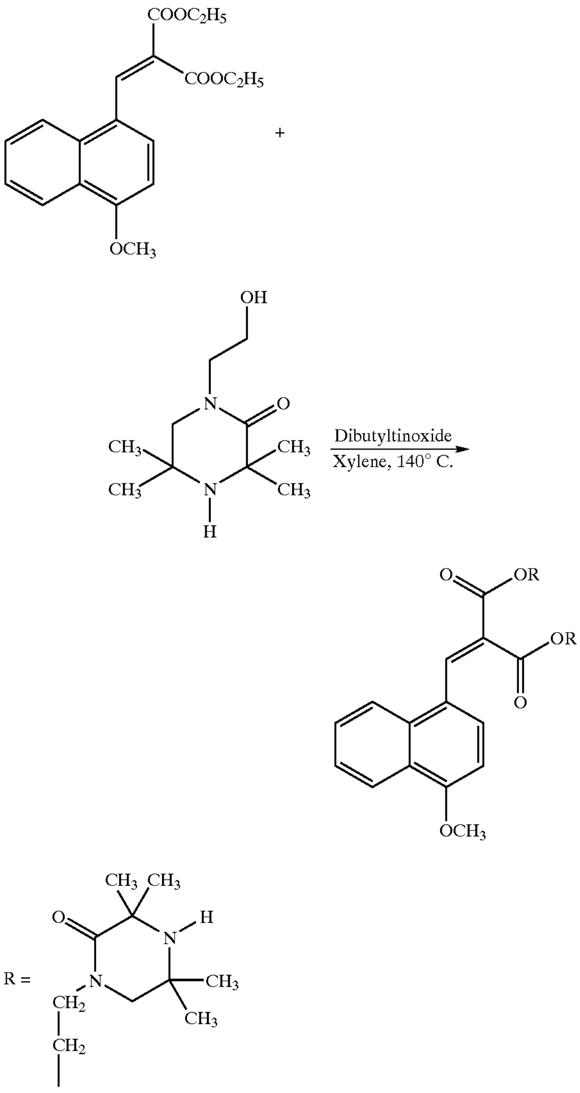

| Reactant | mmol | MW | g |
|---|---|---|---|
| product of example 25a | 20 | 328.36 | 7.56 |
| alcohol of example 1 | 50 | 200.28 | 10 |
| dibutyltinoxide | 0.5 | 248.92 | 0.12 |

In a 250 ml round-bottomed flask, the product of example 25a and the alcohol of example 1 are introduced; the solvent (xylene, 20 ml) is added and the reaction mixture is heated at reflux temperature (140° C.) for 4 hours.

The temperature is brought to 100° C. to add the catalyst, and then the mixture is re-heated at 140° C. for 20 hours.

The solvent is distilled off under reduced pressure and the crude product is chromatographed on a silica gel column with a hexane—THF mixture (50%) as eluant to give the product of the formula

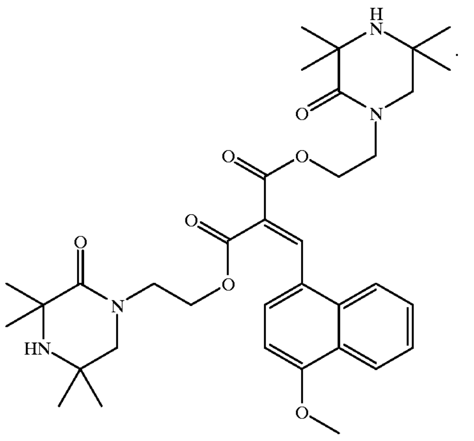

$^1H$ NMR: 8.42 (s, 1H); 8.27 (d, 1H); 7.95 (d, 1H); 7.63–7.42 (m, 2H); 6.75 (d, 1H); 4.41 (t, 2H); 4.24 (t, 2H); 3.96 (s, 3H); 3.70 (t, 2H); 3.34 (t, 2H); 3.28 (s, 2H); 2.58 (s, 2H); 1.41 (s, 6H); 1.20 (s, 6H); 1.11 (s, 6H); 0.70 (s, 6H).

EXAMPLE 30 a) Preparation of the product

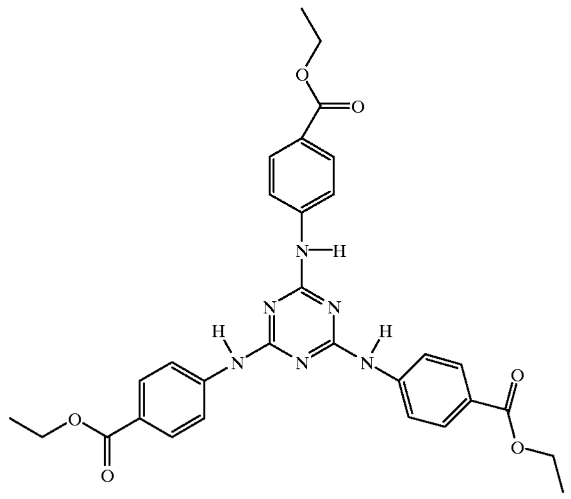

To a solution of 31.8 g (0.1723 mol) of cyanuric chloride in 100 ml of xylene and 300 ml of diethyleneglycoldimethylether (diglyme), 185 g (1.120 mol) of p-aminoethylbenzoate are slowly added. The mixture is left to react for 90 minutes at room temperature, then for 16 hours at 135° C. and additionally for 3 hours at 145° C. The solution is then cooled to room temperature and evaporated under vacuum (70° C./24mbar). The residue is taken up with 400 ml of dichloromethane and 250 ml of water. $KHCO_3$ is then slowly added to the solution under stirring until pH 8 is reached. The mixture reaction is allowed to react for 1 h, filtered and the solid washed with methylenchloride and water. The product is dried under vacuum at 100° C. A white powder of m.p. 234–237° C. is obtained; proton and carbon NMR confirm the above structure.

b) A mixture of 35 g (0.061 mol) of the product from example 30a, 110.5 g (0.0553 mol) of 1-(2-hydroxyethyl)-3,3,5,5-tetramethyl-piperazin-2-one in 250 ml of xylene is heated to reflux, water being distilled off by azeotropation. The mixture is then cooled to 90° C., and 3.5 g (0.014 mol) of dibutyl tin (IV) oxide are added. The mixture is then heated to reflux, xylene and ethanol formed during the reaction being partially distilled off. After 20 hours of reaction, the mixture is cooled to room temperature and 500 ml of methylenechloride are added. The organic solution is then washed three times with 100 ml of water, dried on anhydrous sodium sulfate, filtered and evaporeted under vacuum (70° C./24mbar).

A white powder of m.p. 115–120° C. is obtained. Proton and carbon NMR confirm the expected structure:

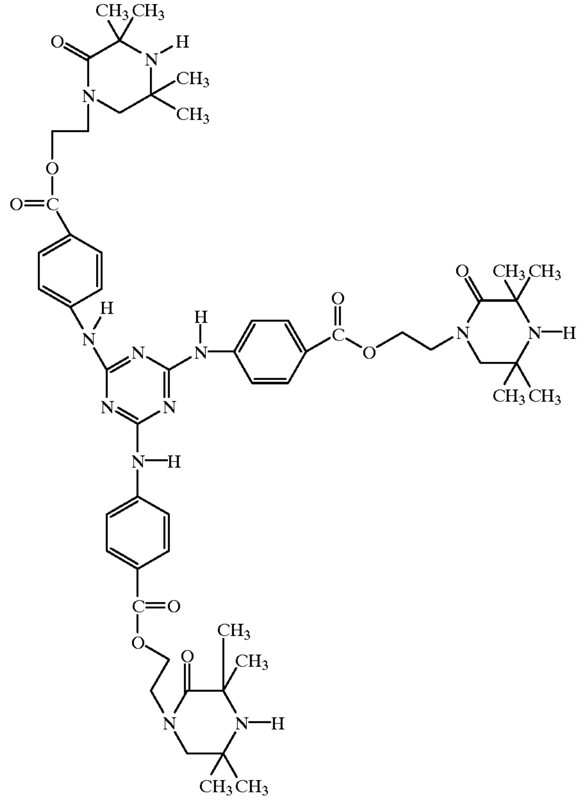

EXAMPLE 31

Following the procedure reported in the following example 33c under the same experimental conditions and using the appropriate reagents, the compound of the formula shown below is obtained as a pale yellow powder of m.p. 79–83° C.; proton and carbon NMR confirm the structure:

Compound of Example 31

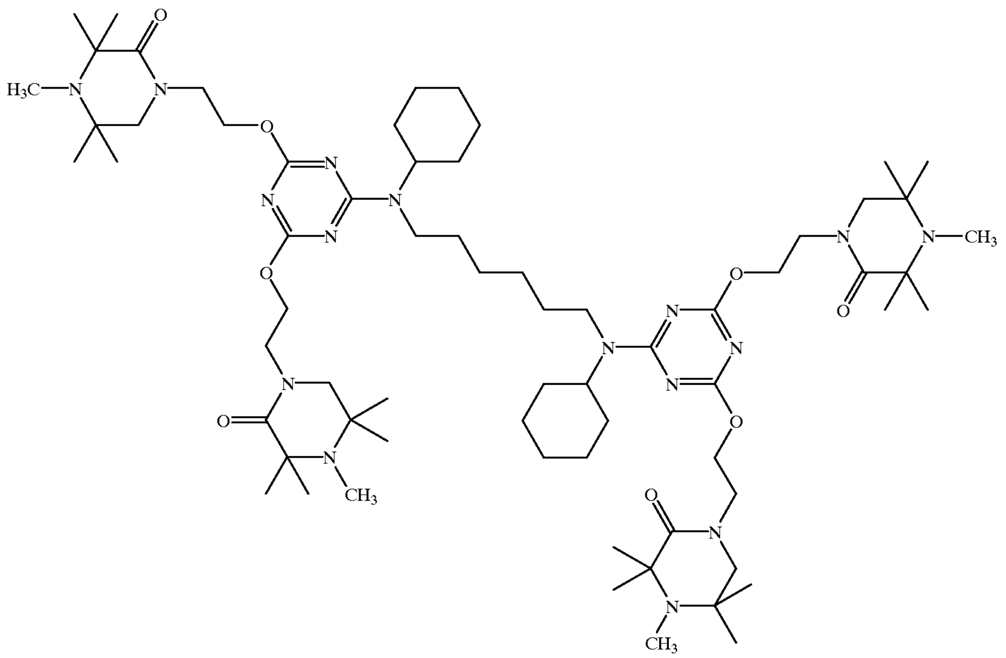

EXAMPLE 32

To a solution of 10 g (0.0542 mol) of cyanuric chloride in 150 ml of xylene, 50 g (0.179 mol) of the product from example 6 are added, and after ½ hour a solution of 50 g (0.054 mol) of sodium carbonate in 15 ml of water is added. The mixture is allowed to react for one hour, then further 7.5 g of sodium carbonate are added and the temperature is raised to 65° C. After 2 hours at 65° C., the mixture is heated to reflux with azeotropic remove of water during 4 hours; then further 10 g of sodium carbonate in 15 ml of water are added. The mixture is allowed to react at reflux for additional 4 hours.The solvent is evaporated off under vacuum. The residue is taken up with 250 ml of dichloromethane and washed with 80 ml of water. The organic solution is then dried under sodium sulfate and evaporated under vacuum (70° C./24mbar). Proton and carbon NMR ($^1H$ NMR: 5.37–4.74 (broad s, 3H); 3.58–3.46 (m, 18H); 3.36–3.34 (m, 6H) 3.26 (s, 6H), 1.74 (q, 6H); 1.30 (s, 18H); 1.12 (s, 18H)) confirm the expected structure:

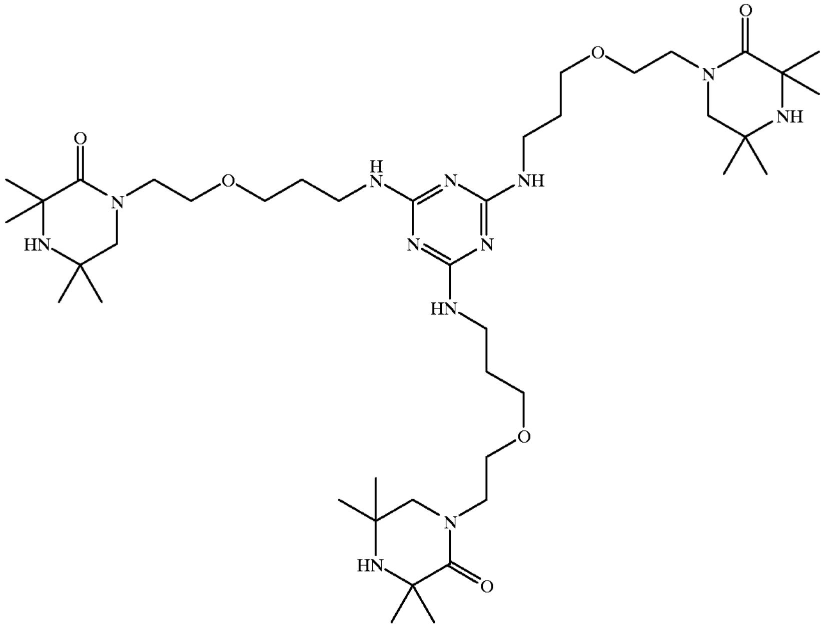

EXAMPLE 33 a) Synthesis of 1-(2-sodiumalkoxy-ethyl)-3,3,5,5-tetramethyl-piperazin-2-one

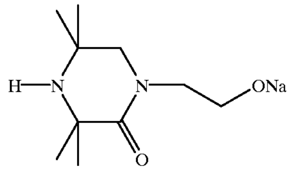

150 g (0.75 mol) of 1-(2-hydroxy-ethyl)-3,3,5,5-tetramethyl-piperazin-2-one are dissolved in 1500 ml of toluene. The solution is heated to reflux while water is distilled off by azeotropation. The mixture is then cooled to 10° C., and under stirring 23.6 g (0.787 mol) of NaH (80% w/w) are slowly added. The temperature is allowed to rise to reflux for 8 hours. The solution is used in example 33b.

b) Preparation of the compound of formula:

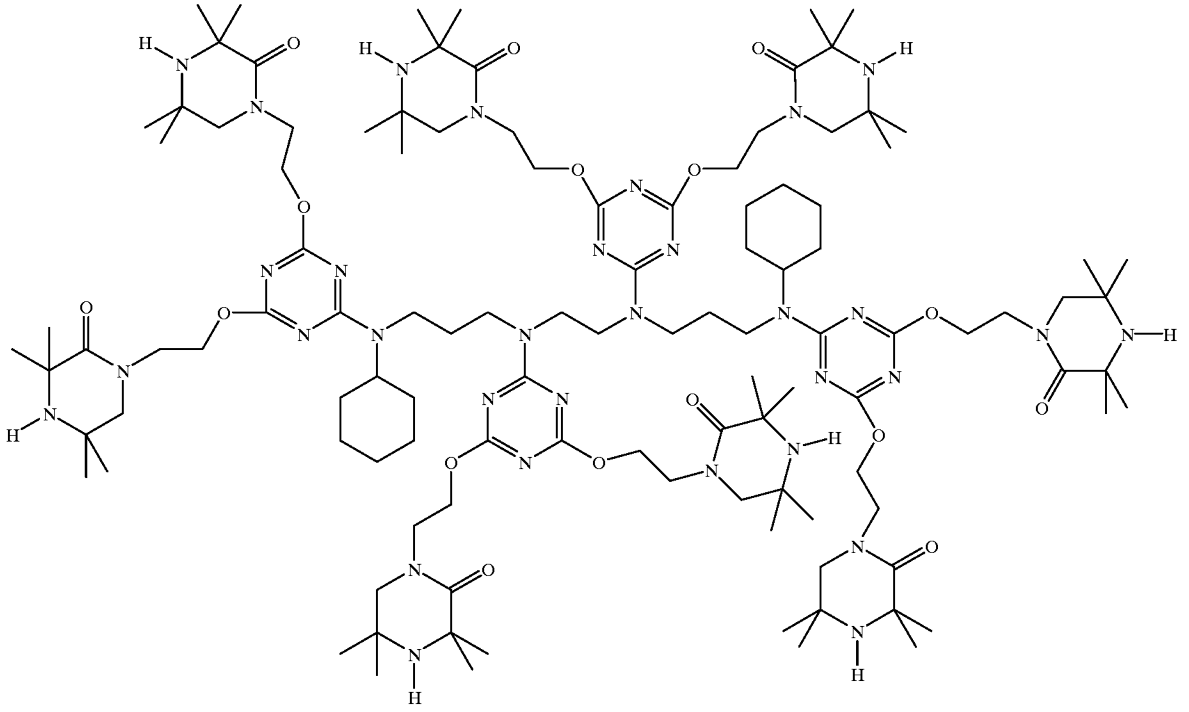

30 g (0.032 mol) of the compound of formula

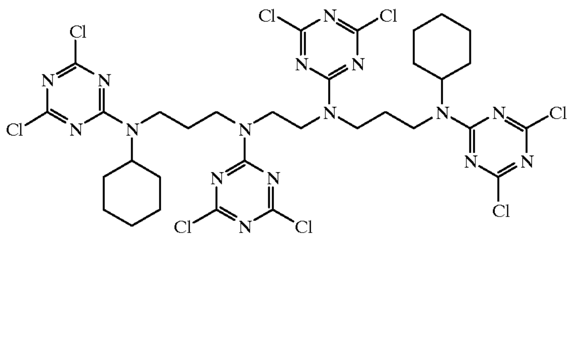

is suspended in toluene. 66.2 g (0.299 mol) of the reagent from example 34a are slowly added. The mixture is allowed to react for 2 hours. The solution is then cooled to room temperature and evaporated under vacuum (70° C./24mbar). The residue is taken up with 400 ml of dichloromethane and washed three times with 50 ml of water. The organic solution is then dried under sodium sulfate and evaporated under vacuum (70° C./24mbar).

A pale yellow powder is obtained. Proton NMR confirms the above structure.

c) To a solution of 25 g (0.0111 mol) of the compound from example 33b in 150 ml of tert-amyl alcohol, 16 g (0.512 mol) of paraformaldehyde are added. The mixture is heated to 80° C. and 24.4 g (0.540 mol) of formic acid in 10 ml of tert-amyl alcohol are slowly added. The mixture is then stirred for 3 hours at 80° C. 300 ml of toluene are then added and the mixture is cooled to room temperature. A solution of 23 g (0.575 mol) of sodium hydroxide in 100 ml of water is then slowly added. After stirring for 1 hour, the organic phase is separated, washed twice with water, dried over anhydrous sodium sulfate, filtered and evaporated under vacuum (80° C./1.3 mbar). A pale yellow powder, m.p. 56–62° C., is obtained. Proton NMR confirms the expected structure:

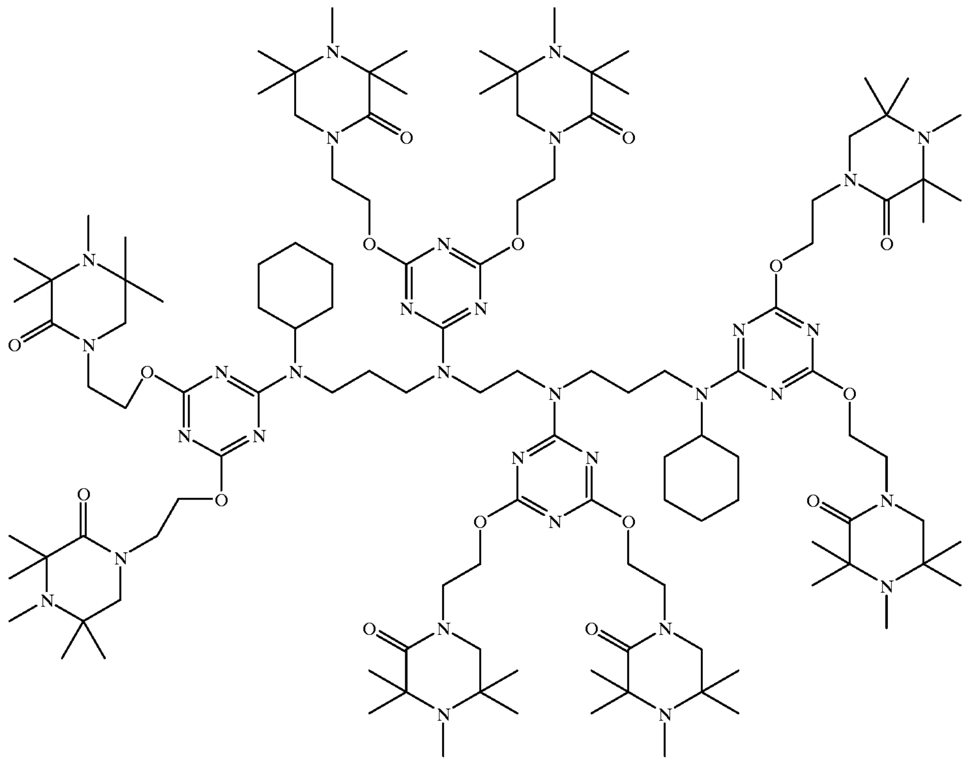

EXAMPLE 34

Following the procedure reported in the example 33b under the same experimental conditions and using the appropriate reagents, the compound of the formula

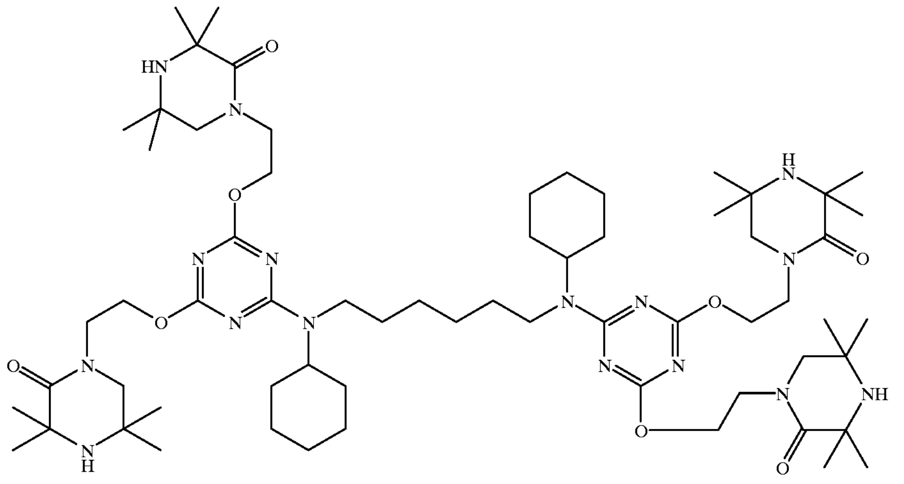

is prepared as a pale yellow powder of m.p. 77–82° C. Proton and carbon NMR confirm the structure.

EXAMPLE 35

Following the procedure reported in the example 33b under the same experimental conditions and using the appropriate reagents, the compound of the formula given below is obtained as a pale yellow powder of m.p. 56–62° C. Proton NMR confirms the structure:

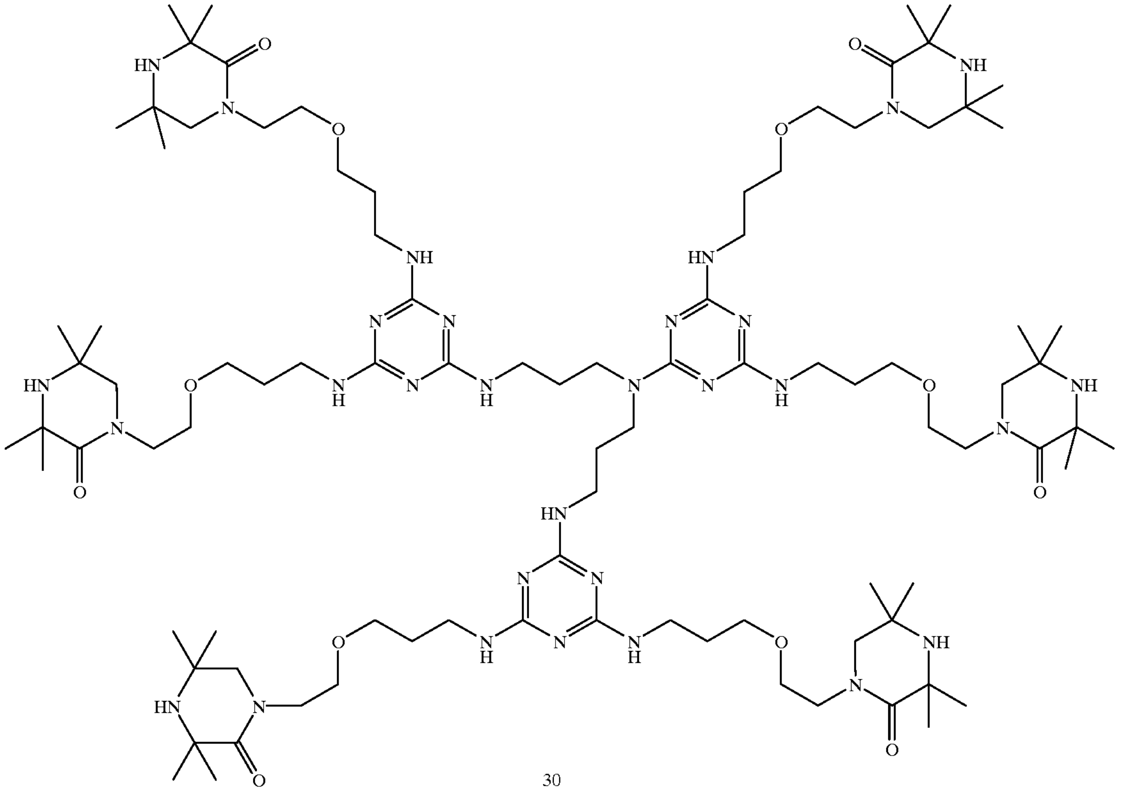
EXAMPLE 36
Following the procedure reported in the example 33c under the same experimental conditions and using the appropriate reagents, the compound of the formula given below is obtained. Proton NMR confirms the expected structure:
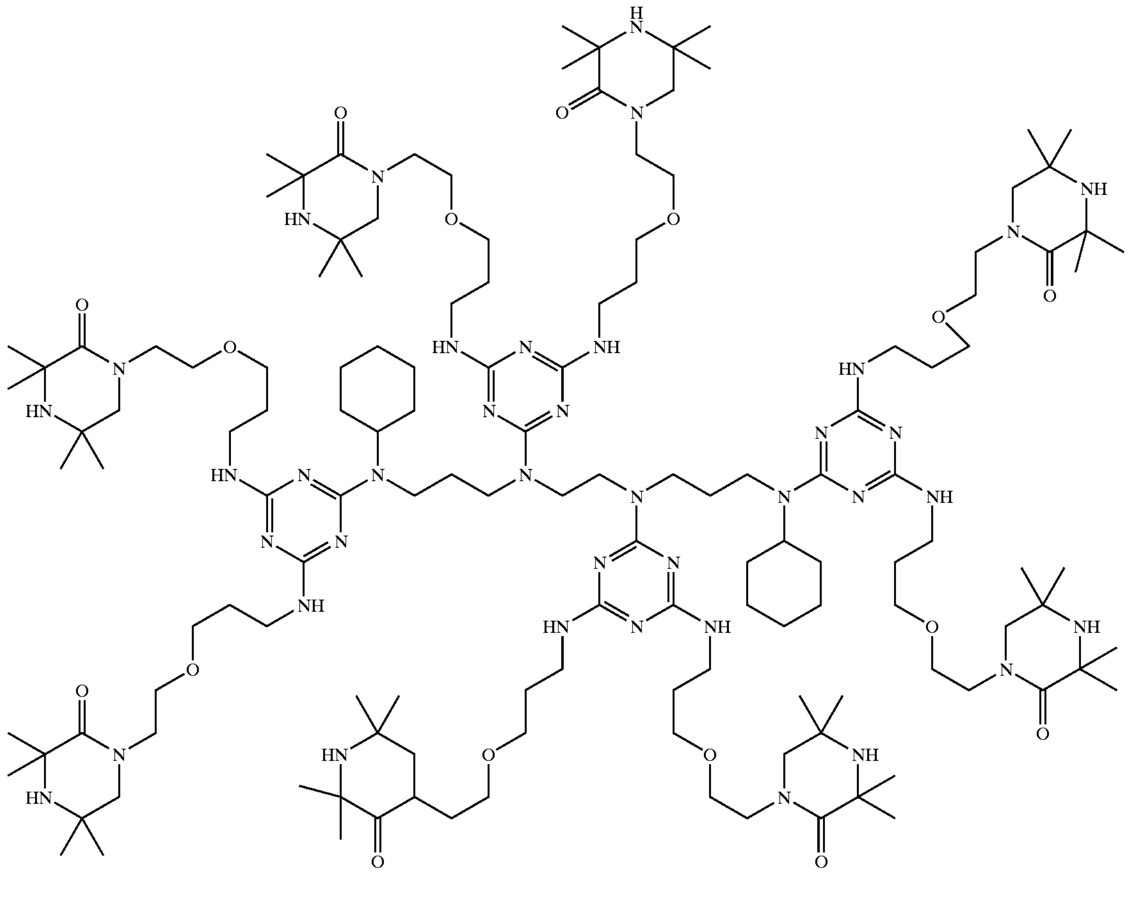

Elemental analysis: calculated: C=60.5; H=9.1; N=20.8 found: C=60.2; H=9.3; N=20.8.

EXAMPLES 37–38

Following the procedure reported in the example 21 under the same experimental conditions and using the appropriate reagents, the compounds of the formulae (Ex.37)

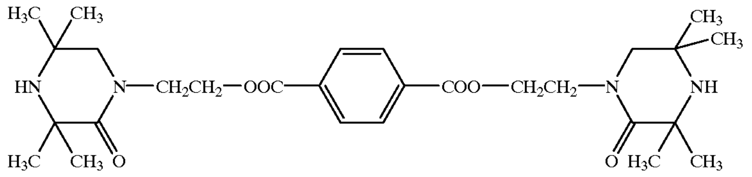

and (Example 38)

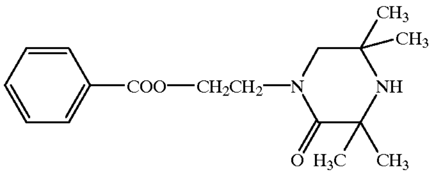

are obtained. Physical data:

EXAMPLE 37

White solid, m.p. 123° C.

EXAMPLE 38

Oil; 1H NMR (300 MHz, CDCl3)/ppm: 1.11 (s, 6H); 1.29 (s, 6H); 3.27 (s, 2H); 3.73 (t, 2H); 4.44 (t, 2H); 7.20–7.40 (m, 3H); 7.96 (m, 1H).

EXAMPLE 39–41

Following the procedure reported in the example 22 under the same experimental conditions and using the appropriate reagents, the compounds of the following formulae are obtained:

(Example 39)

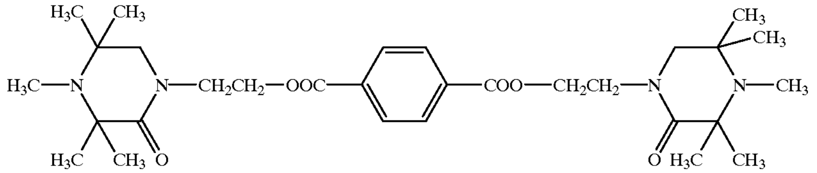

(Example 40)

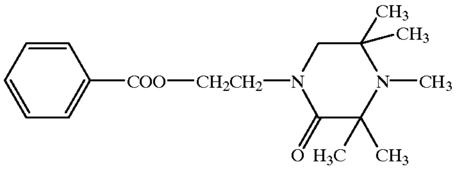

(Example 41)

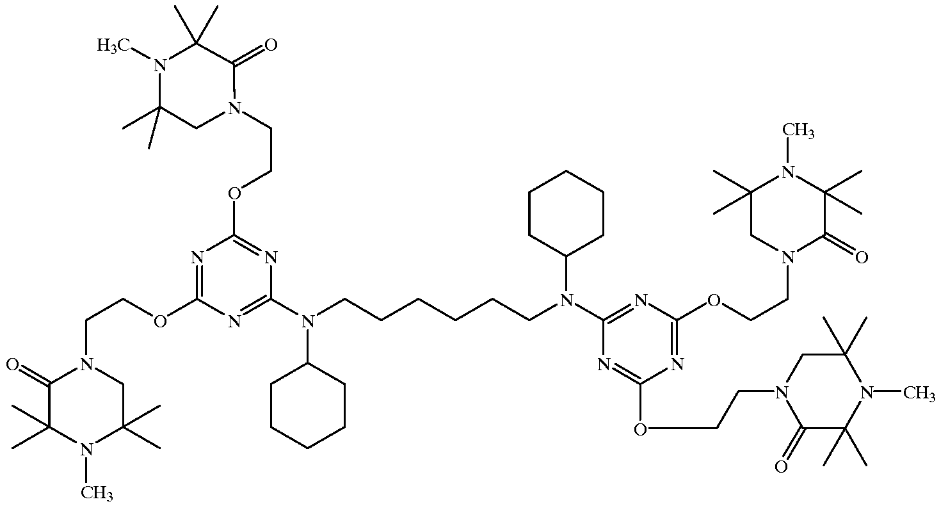

Physical data:

EXAMPLE 39

White solid, m.p. 123° C.

EXAMPLE 40

White solid, m.p. 79.3° C.

EXAMPLE 41

EXAMPLES 42–44

To a solution of 60 g (0.113 mol) of the product from example 37 in 250 ml of dichloromethane cooled to 0° C. and 22.9 g (0.226 mol) of triethyamine, a solution of 21.5 g (0.237 mol) of acryloylchloride in 50 ml of dichloromethane are slowly added. After the addition the mixture is allowed to react for additionaly 1 hour at 0° C. and then the mixture is heated to room temperature and left to react for additionaly 4 hours. The mixture is then filtered and washed three times with water; the organic layer is separated, dried on sodium sulphate and then evaporated under vacuum.

The compound of the formula

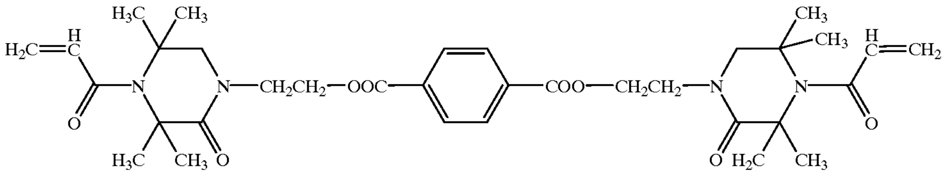

(example 42) is obtained as a white solid, m.p. 167° C.

Following the above procedure under the same experimental conditions and using the appropriate reagents, the compounds of the following formulae are obtained:

(Example 43)

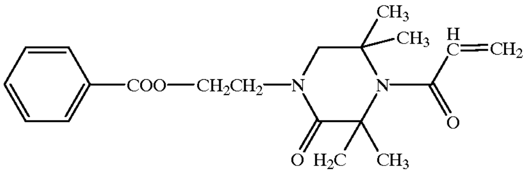

(Example 44)

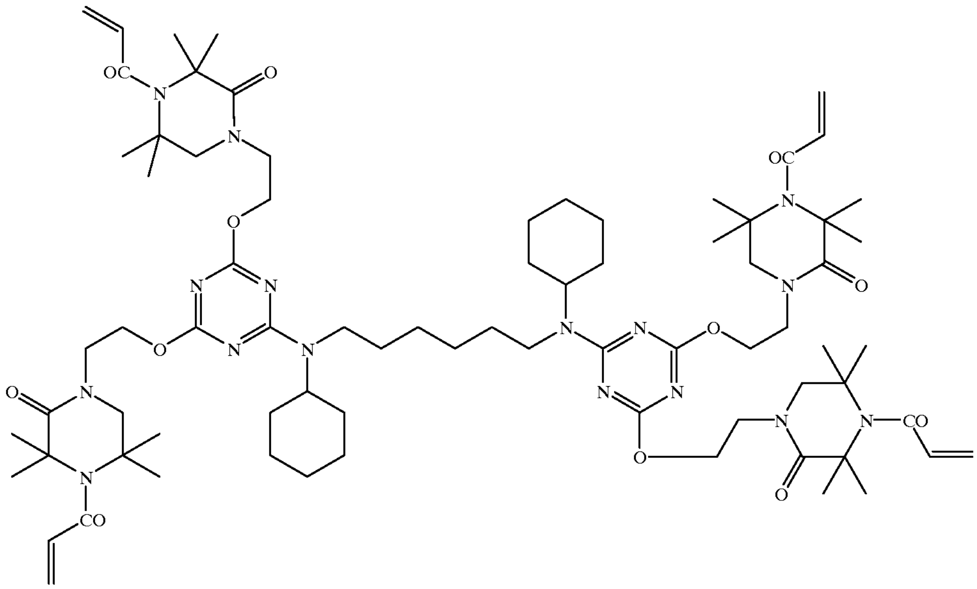

Physical Data

EXAMPLE 42

White solid, m.p. 167° C.

EXAMPLE 43

Waxy solid; 1H NMR (300 MHz, CDCl3)/ppm: 1.37 (s, 6H); 1.61 (s, 6H); 3.29 (s, 2H); 3.82 (t, 2H); 4.42 (t, 2H); 5.41–5.53 (m, 1H); 6.24–6.31 (m, 1H); 6.38–6.72 (m,1H); 7.30–7.61 (m, 3H); 7.83 (m, 2H).

EXAMPLE 44

EXAMPLE 45

Preparation of the Compound of Formula

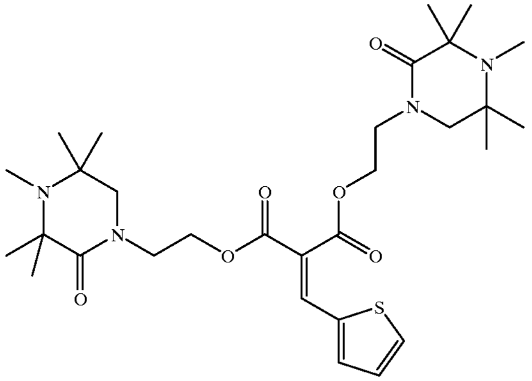

Following the procedure of example 21, 30 g (0.133 mol) of 2-thiophen-2-ylmethylene-malonic acid dimethyl ester are reacted with 58.4 g (0.292 mol) of 1-(2-hydroxyethyl)-3,3,5,5-tetramethyl-piperazin-2-one.

The product is then treated following the preparation in example 22 in order to carry out the methylation step.

The title compound is obtained as a brown resin.

$^1$H NMR: 7.83 (s, 1H); 7.58–6.91 (m, 3H); 4.46 (t, 2H); 4.35 (t, 2H); 3.64 (t, 4H); 3.12 (s, 2H); 3.07 (s, 2H); 2.21 (s, 3H); 2.16 (s, 3H); 1.28 (s, 6H); 1.24 (s, 6H); 1.04 (s, 6H); 0.94 (s, 6H);.

EXAMPLE 46

Preparation of the Compound of Formula

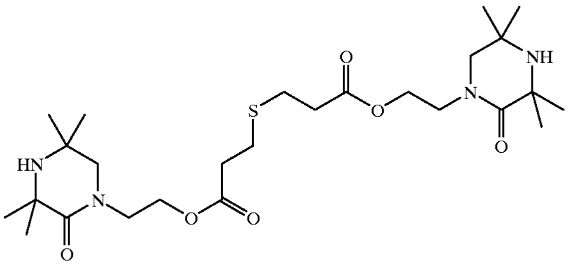

Following the procedure of example 21, 26.6 g (0.1136 mol) of 3-(2-ethoxycarbonyl-ethylsulfanyl)-propionic acid ethyl ester are reacted with 50 g (0.25 mol) of 1-(2-Hydroxyethyl)-3,3,5,5-tetramethyl-piperazin-2-one.

The title compound is obtained as a yellow liquid.

$^1$H NMR: 4.18 (t, 4H); 3.54 (t, 4H); 3.19 (s, 4H); 2.48 (t, 4H); 1.26 (s, 12H); 1.10(s, 12H).

The following compounds are examples for polymeric compounds of the invention obtainable from compounds of formula I (n being from the range 5 to 25):

EXAMPLE 50

A solution of 36.6 g (0.143 mol) of the product from example 7 in 150 ml of toluene is heated to reflux, water being distilled off by azeotropation. The mixture is then cooled to 80° C. and 0.64 g (0.006 mol) of potassium tert-butylate are added. The mixture is refluxed for 7 hours and then evaporated under vacuum (150° C./24 mbar). The compound of the below formula is obtained as a brown resin; $M_w$=5489; $M_n$=4450; $M_{w/n}$=1.23 (GPC).

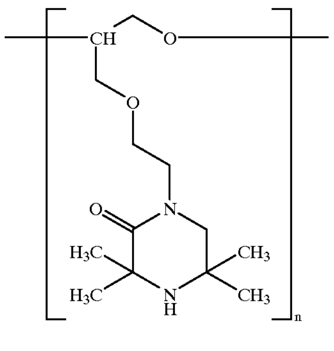

EXAMPLE 51

Following the procedure reported in the example 50 under the same experimental conditions and using the reagent from example 8, the compound of the formula

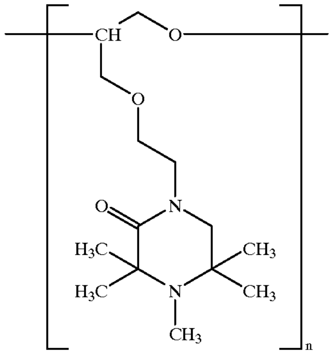

is obtained;
$M_w$=4987
$M_n$=3917
$M_{w/n}$=1.27 (GPC).

EXAMPLE 52

A mixture of 10.5 g (0.072 mol) of dimethylsuccinate, 17.5 g (0.072 mol) of 1,4-bis-(2-hydroxyethyl)-3,3,5,5-tetramethyl-piperazin-2-one (example 6) in 250 ml of xylene is heated to reflux, water being distilled off by azeotropation. The mixture is then cooled down to 90° C. and 0.15 g (0.008 mol) of lithiumamide are added. The mixture is then heated to reflux, xylene and methanol formed during the reaction being partially distilled off. After 20 hours of reaction the mixture is cooled and the organic solution is then washed three times with 50 ml of water, dried on anhydrous sodium sulfate, filtered and evaporeted under vacuum (150° C./24 mbar). The compound of the formula

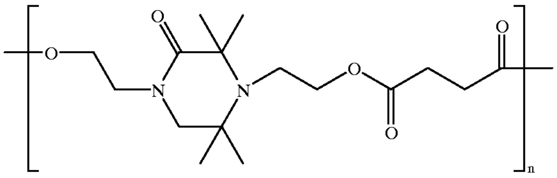

is obtained as a yellow resin; GPC analysis: $M_w$=6229; $M_n$=3915; $M_{w/n}$=1.59.

Application Examples

EXAMPLE 60

Light-stabilizing Action in Polypropylene Plaques 1 g each of the compounds indicated in Table 1, 1 g of tris(2,4-di-t-butylphenyl)phosphite, 0.5 g of pentaerythritol tetrakis [3-(3,5-di-t-butyl-4-hydroxy phenyl)propionate], 1 g of calcium stearate and 1 g of Filofin Blue G are mixed in a turbo mixer with 1000 g of polypropylene powder of melt index=4 g/10 minutes (measured at 230° C. an 2.16 kg).

The mixtures obtained are extruded at a temperature of 200–230° C. to give polymer granules which are then converted into plaques of 2 mm thickness by injection moulding at 200–220° C. The plaques obtained are exposed in a model 65 WR Weather-O-Meter (ASTM D2565-85) with a black panel temperature of 63° C. until surface embrittlement (chalking) starts. A plaque of polypropylene prepared under the same conditions as indicated above but without the addition of the compounds of the invention is exposed for comparison.

In Table 1, the exposure time needed to reach this start of embrittlement is given in hours. The longer the time the better is the stabilizing effect.

TABLE 1

| Stabilizer | Chalking time (hours) |
|---|---|
| without stabilizer | 570 |
| compound of Example 21 | 5700 |
| compound of Example 22 | >1000 |

EXAMPLE 62

Light-Stabilizing Action in Polypropylene Tapes 1 g of each of the compounds listed in Table 2, 1 g of tris[2,4-di-tert-butylphenyl]phosphite, 0.5 g of pentaerythritol tetrakis[3-(3,5-di-tert-butyl-4-hydroxy-phenyl) propionate] and 1 g of calcium stearate are mixed in a turbomixer with 1000 g of polypropylene powder having a melt index of 2.1 (measured at 230° C. and 2.16 kg).

The mixtures are extruded at 200–220° C. to give polymer granules which are subsequently converted to stretched tapes of 50 μm thickness and 2.5 mm width, using a semi-industrial type of apparatus (®Leonard-Sunirago (VA)-Italy) and waking under the following conditions:

| | |
|---|---|
| Extruder temperature: | 210–230° C. |
| Head temperature: | 240–260° C. |
| Stretch ratio: | 1:6 |

The tapes thus prepared are mounted on a white card and exposed in a Weather-O-Meter 65 WR (ASTM D 2565-85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

By way of comparison, tapes prepared under the same conditions as indicated above, but without the addition of the stabilizers of the present invention, are exposed. The results are shown in Table 2.

TABLE 2

| Stabilizer | $T_{50}$ (hours) |
|---|---|
| without stabilizer | 500 |
| compound of Example 11 | 2060 |
| compound of Example 12 | 1700 |
| compound of Example 14 | 2260 |
| compound of Example 15 | 2190 |
| compound of Example 31 | 2170 |
| compound of Example 32 | 1860 |
| compound of Example 52 | 2660 |

EXAMPLE 63

Light-stabilizing Action in Polypropylene Plaques 1 g each of the compounds indicated in Table 3, 1 g of tris(2,4-di-t-butylphenyl)phosphite, 0.5 g of pentaerythritol tetrakis[3-(3,5-di-t-butyl-4-hydroxy-phenyl)propionate], 1 g of calcium stearate and 1 g of Filofin Blue G are mixed in a turbo mixer with 1000 g of polypropylene powder of melt index=4 g/10 minutes (measured at 230° C. and 2.16 kg).

The mixtures obtained are extruded at a temperature of 200–230° C. to give polymer granules which are then converted into plaques of 2 mm thickness by injection moulding at 200–220° C. The plaques obtained are exposed in a model 65 WR Weather-O-Meter (ASTM D 2565-85) with a black panel temperature of 63° C. until surface embrittlement (chalking) starts. A plaque of polypropylene prepared under the same conditions as indicated above but without the addition of the compounds of the invention is exposed for comparison.

In Table 3, the exposure time needed to reach this start of embrittlement is given in hours. The longer the time, the better is the stabilizing effect.

TABLE 3

| Stabilizer | Chalking time (hours) |
|---|---|
| without stabilizer | 570 |
| compound of Example 11 | 4000 |
| compound of Example 12 | 3160 |
| compound of Example 14 | 2830 |
| compound of Example 15 | 2830 |

Components used in the following examples 65–67
Coupler Y1
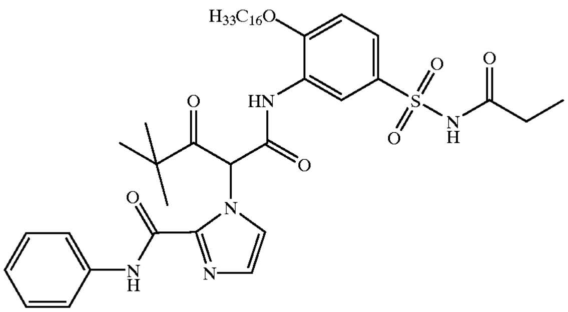
Coupler Y2
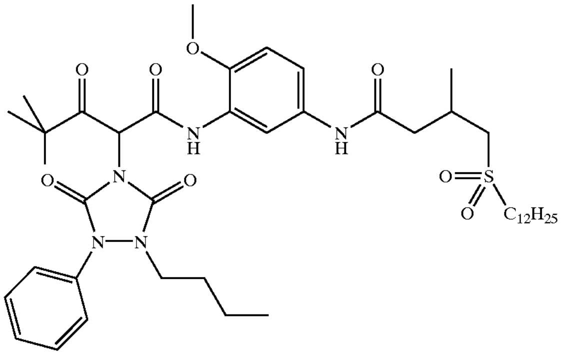
Coupler Y3
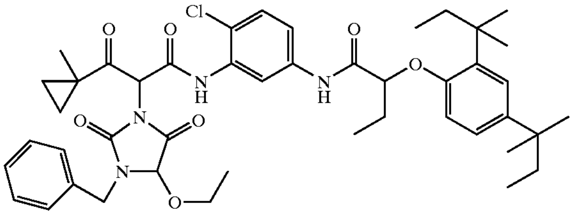
Coupler Y4
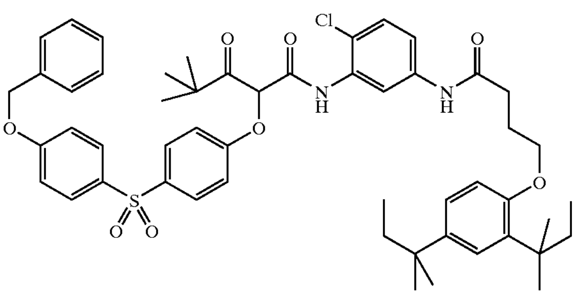
-continued
coadd1
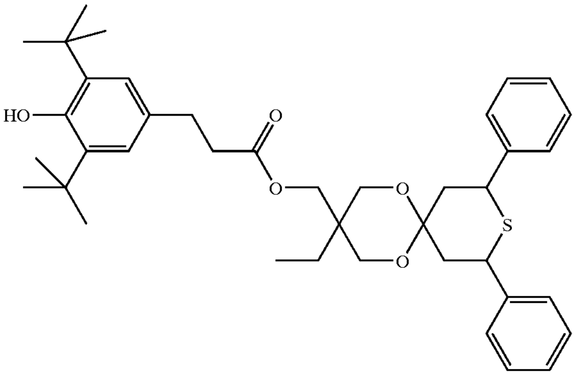
coadd2
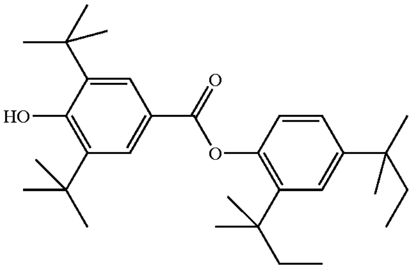
solv1
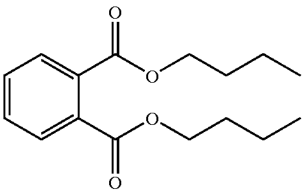
ha1
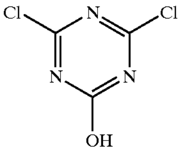
su1
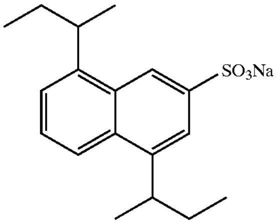
EXAMPLE 64
Chromogenic photographic layers are prepared by hand-coating a gelatine emulsion containing silver bromide, yellow coupler and an additive of the invention on a polyethylene-coated paper.

The composition of the layer is as given in the following table:

| Component | Amount in the layer |
|---|---|
| Gelatine | 5150 $mg/m^2$ |
| AgBr | 520 $mg/m^2$ |
| Yellow coupler (cf table 4) | 1.07 $mmol/m^2$ |
| Coupler solvent solv1 | 0.33 g/g coupler |
| Additive (cf table 4) | 0.30 g/g coupler |
| Hardener ha1 | 300 $mg/m^2$ |
| Surfactant su1 | 340 $mg/m^2$ |

The layers are dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the yellow dye is measured in the blue channel.

TABLE 4

| Additive | Coupler | 100 × $D_{max}$ |
|---|---|---|
| none | Coupler Y1 | 206 |
| 32 | Coupler Y1 | 270 |
| 10 | Coupler Y1 | 238 |
| 11 | Coupler Y1 | 238 |
| 14 | Coupler Y1 | 262 |
| 15 | Coupler Y1 | 255 |
| 21 | Coupler Y1 | 236 |
| none | Coupler Y2 | 176 |
| 32 | Coupler Y2 | 199 |
| none | Coupler Y4 | 212 |
| 32 | Coupler Y4 | 222 |
| 34 | Coupler Y4 | 218 |
| 31 | Coupler Y4 | 219 |

The previous results show that the additive of the present invention improves the maximal dye yield.

EXAMPLE 65

Chromogenic photographic layers are prepared by hand-coating a gelatine emulsion containing silver bromide, yellow coupler and an additive on a polyethylene-coated paper.

The composition of the layer is as given in following table, amounts are in $mg/m^2$:

| Component | Amount in the layer |
|---|---|
| Gelatine | 5150 |
| AgBr | 520 |
| Yellow coupler (cf table 5) | 1.07 $mmol/m^2$ |
| Coupler solvent solv1 | 0.33 g/g coupler |
| Additive (cf table 5) | 0.30 g/g coupler |
| Hardener ha1 | 300 |
| Surfactant su1 | 340 |

The layers are dried for 7 days in a ventilated cabinet.

The layers are dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the yellow dye is measured in the blue channel. The samples are then exposed in an Atlas weatherometer so as to receive 60 $kJ/cm^2$ light energy. The temperature is 43° C. and the relative humidity 50%. The density loss starting from a blue-density of 1 is determined.

TABLE 5

| Additive | Coupler | $-\Delta D(60\ kJ/cm^2$, from OD = 1) in % |
|---|---|---|
| none | Coupler Y1 | 55 |
| 32 | Coupler Y1 | 32 |
| 34 | Coupler Y1 | 39 |
| 10 | Coupler Y1 | 31 |
| 31 | Coupler Y1 | 28 |
| 35 | Coupler Y1 | 29 |
| 33c | Coupler Y1 | 35 |
| 13 | Coupler Y1 | 36 |
| none | Coupler Y2 | 47 |
| 34 | Coupler Y2 | 29 |
| 31 | Coupler Y2 | 19 |
| 35 | Coupler Y2 | 24 |
| 33c | Coupler Y2 | 20 |
| 16 | Coupler Y2 | 30 |
| none | Coupler Y3 | 32 |
| 34 | Coupler Y3 | 22 |
| 16 | Coupler Y3 | 24 |
| none | Coupler Y4 | 41 |
| 32 | Coupler Y4 | 31 |
| 34 | Coupler Y4 | 22 |
| 31 | Coupler Y4 | 27 |
| 33c | Coupler Y4 | 30 |

The previous results show that additives of the present invention improve the light stability of yellow photographic layers.

EXAMPLE 66

Chromogenic photographic layers are prepared by hand-coating a gelatine emulsion containing silver bromide, yellow coupler, an additive of the invention in combination with a co-stabiliser on a polyethylene-coated paper.

The composition of the layer is given in following table, amounts are in $mg/m^2$.

| Component | Amount in the layer |
|---|---|
| Gelatine | 5150 |
| AgBr | 520 |
| Yellow Coupler Y1 | 835 |
| Coupler solvent solv1 | 278 |
| Additive of the invention | see TABLE 6 |
| Co-stabiliser | see TABLE 6 |
| Hardener ha1 | 300 |
| Surfactant su1 | 340 |

The layers are dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the yellow dye is measured in the blue channel. The samples are then exposed in an Atlas weatherometer so as to receive 60 $kJ/cm^2$ light energy. The temperature is 43° C. and the relative humidity 50%. The density loss starting from a blue-density of 1 is determined.

TABLE 6

| Additive of the invention | mg/m² | Co-additive | mg/m² | -ΔD(60 kJ/cm², from OD = 1) |
|---|---|---|---|---|
| none | | | | 55 |
| — | | coadd1 | 250 | 43 |
| 31 | 250 | — | — | 38 |
| 31 | 125 | coadd1 | 125 | 37 |
| 31 | 83 | coadd1 | 167 | 37 |
| — | — | coadd2 | 250 | 49 |
| 31 | 125 | coadd2 | 125 | 36 |
| 31 | 83 | coadd2 | 167 | 38 |

The previous results show that additives of the present invention improve the efficiency of classical stabilisers used in yellow photographic layers.

EXAMPLE 67

Chromogenic photographic layers are prepared by hand-coating a gelatine emulsion containing silver bromide, yellow coupler, an additive of the invention in combination with a co-stabiliser on a polyethylene-coated paper.

The compostion of the layer is given in following table, amounts are in $mg/m^2$:

| Component | Amount in the layer |
|---|---|
| Gelatine | 5150 |
| AgBr | 520 |
| Yellow Coupler Y2 | 854 |
| Coupler solvent solv1 | 285 |
| Additive of the invention | see Table 7 |
| Co-stabiliser | see Table 7 |
| Hardener ha1 | 300 |
| Surfactant su1 | 340 |

The layers are dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the yellow dye is measured in the blue channel. The samples are then exposed in an Atlas weatherometer so as to receive 60 $kJ/cm^2$ light energy. The temperature is 43° C. and the relative humidity 50%. The density loss starting from a blue-density of 1 is determined.

TABLE 7

| Additive of the invention | mg/m² | Co-additive | mg/m² | -ΔD(60 kJ/cm², from OD = 1) |
|---|---|---|---|---|
| none | | | | 43 |
| — | | coadd1 | 256 | 27 |
| 31 | 256 | — | — | 24 |
| 31 | 128 | coadd1 | 128 | 22 |

The previous results show that additives of the present invention improve the efficiency of classical stabilisers used in yellow photographic layers.

EXAMPLE 68

Stabilization of a Gray Pigmented Polycarbonate/ABS Blend

To a commercial PC/ABS blend (Cycoloy® MC8002 natural) is added pigment and additives as indicated below followed by extrusion compounding on an 18 mm twin screw extruder operated at 245° C. die temperature. The pigment is Gray 9779 (Uniform Color Co.), used in an amount of 1% by weight of the polymer blend.

Izod bars (2.5×0.5×0.125 inches) are molded on a BOY 50 ton injection molding machine operated at 515–530° F. All samples are stabilized by addition of 1% by weight of 2-(2'-hydroxy-3',5'-bis(1,1-dimethylbenzyl)phenyl)-benztriazole (C) and the amount of compound of the formula I as indicated in the following table (amounts given by weight of the polymer blend). Further samples without additives are tested for the purpose of comparison.

Color values are measured per ASTM D1925 on a Chromasensor ACS spectrophotometer.

Accelerated weathering was conducted using an Atlas Ci65A xenon arc weather-O-meter. Dry xenon setup is 63° C. black panel temp, irradiance 0.35 watt/square meter. Interior auto xenon is 89° C. black panel temp, irradiance 0.55 watt/square meter. Results are compiled in table 8.

TABLE 8

Cycoloy MC8002 PC/ABS (Gray 9779 Pigmented). Delta E Color. Dry XAW exposure.

| | Irradiance Hours = | | | | | | |
|---|---|---|---|---|---|---|---|
| Wgt. % Additive | 94.8 | 249.7 | 500.5 | 750.0 | 999.7 | 1249.0 | 1498.7 |
| none | 1.5 | 3.3 | 6.9 | 9.0 | 9.8 | 11.0 | 10.7 |
| 1% C | 0.7 | 1.7 | 4.2 | 6.7 | 7.7 | 9.0 | 9.1 |
| 1% C + 0.5% cpd. 11 | 0.2 | 0.6 | 2.2 | 4.7 | 5.5 | 7.7 | 8.2 |
| 1% C + 0.5% cpd. 21 | 0.6 | 0.5 | 2.0 | 5.5 | 6.2 | 8.4 | 8.7 |

What is claimed is:

1. A compound of formula (I)

(I)

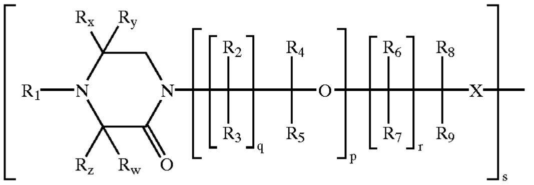

wherein p is zero or 1;

q and r, independently of each other, are an integer from 1 to 6; and s is a number ranging from 1 to 8;

X is —O— or, when p is 1, X is also a group

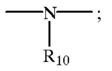

$R_w$, $R_x$, $R_y$ and $R_z$ are, independently of each other, $C_1$–$C_{18}$alkyl, $C_5$–$C_{12}$cycloalkyl or $C_1$–$C_5$hydroxyalkyl;

$R_1$ is hydrogen; $C_1$–$C_{18}$alkyl; oxyl; OH; $CH_2CN$; $C_1$–$C_{18}$alkoxy; $C_5$–$C_{12}$cycloalkoxy; $C_3$–$C_8$alkenyl; $C_3C_8$alkynyl; $C_7$–$C_{12}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–$C_{15}$phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1$–$C_{18}$alkanoyloxy; glycidyl; or a group —$CH_2CH(OH)$—G, in which G is hydrogen, methyl or phenyl;

$R_2$ and $R_6$, independently of each other, are hydrogen, $C_1$–$C_8$alkyl, $C_5$–$C_{12}$cycloalkyl or $C_1$–$C_4$hydroxyalkyl;

$R_3$, $R_4$, $R_5$, $R_7$, $R_8$, $R_9$, independently of each other, are hydrogen, $C_1$–$C_8$alkyl or $C_5$–$C_{12}$cycloalkyl;

when s is 1,

W is $C_1$–$C_{18}$alkyl; $C_2$–$C_{18}$alkyl which is substituted by $NH_2$, $NHR_{10}$, $N(R_{10})_2$, nitro, hydroxy and/or $OR'_{13}$; or W is $C_5$–$C_{12}$cycloalkyl; $C_5$–$C_{12}$cycloalkyl which is substituted by OH, $C_1$–$C_4$alkyl or $C_1$–$C_4$alkoxy; $C_3$–$C_6$alkenyl; $C_3$–$C_{12}$epoxyalkyl; $C_7$–$C_{15}$phenylalkyl which is unsubstituted or substituted on the phenyl ring by a radical selected from $C_1$–$C_4$alkyl and $C_1$–$C_4$alkoxy; or W is one of the groups of the formulae (IIa)–(IIe)

(IIa)

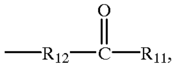

(IIb)

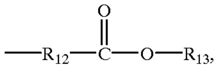

(IIc)

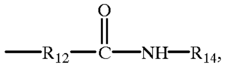

(IId)

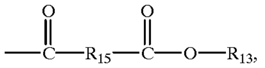

(IIe)

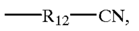

or, when $R_1$ is a group —$CH_2CH(OH)$—G, W may also be hydrogen;

$R_{10}$ is hydrogen, $C_1$–$C_8$alkyl, $C_5$–$C_{12}$cycloalkyl, $C_7$–$C_{15}$phenylalkyl which is unsubstituted or substituted on the phenyl ring by a radical selected from $C_1$–$C_4$alkyl and $C_1$–$C_4$alkoxy;

$R_{11}$ is hydrogen; $C_1$–$C_{17}$alkyl; $C_1$–$C_{12}$alkyl substituted by a radical selected from the group consisting of OH, $C_1$–$C_{12}$alkoxy, benzophenonyl and benzophenonyloxy, wherein one or both phenyl rings of the benzophenone moiety are unsubstituted or substituted by a radical selected from OH, halogen, $C_1$–$C_4$alkyl and $C_1$–$C_{18}$alkoxy; or $R_{11}$ is $C_5$–$C_{12}$cycloalkyl which is unsubstituted or substituted by $C_1$–$C_4$alkyl; $C_2$–$C_{17}$alkenyl; phenyl; phenyl substituted by $NH_2$, $NHR_{10}$, $N(R_{10})_2$, or $C_1$–$C_4$alkyl or $C_1$–$C_4$alkoxy; $C_7$–$C_{15}$phenylalkyl; $C_8$–$C_{15}$phenylalkenyl; or $C_7$–$C_{15}$phenylalkyl which is substituted on the phenyl ring by $C_1$–$C_4$alkyl and/or $C_1$–$C_4$alkoxy;

$R_{12}$ is a direct bond or $C_1$–$C_{12}$alkylene; phenylene; cyclohexylene;

$R_{13}$ is $C_1$–$C_{18}$alkyl; $C_2$–$C_{18}$alkyl which is substituted by a radical selected from $NH_2$, $NHR_{10}$, $N(R_{10})_2$, nitro, hydroxy, $OR_{13}$; $C_3$–$C_{18}$alkenyl; $C_5$–$C_{12}$cycloalkyl; $C_5$–$C_{12}$cycloalkyl which is substituted by $C_1$–$C_4$alkyl or interrupted by —O— or both substituted by $C_1$–$C_4$alkyl and interrupted by —O—; and when W is a group (IId) or W is a group (IIb) while $R_{12}$ is not a direct bond, $R_{13}$ can be also hydrogen, or one equivalent of a cation of main groups I or II of the periodic system;

$R'_{13}$ is $C_1$–$C_{18}$alkyl; $C_2$–$C_{18}$alkyl which is substituted by a radical selected from $NH_2$, $NHR_{10}$, $N(R_{10})_2$, nitro, hydroxy, $OR_{13}$; $C_3$–$C_{18}$alkenyl; $C_5$–$C_{12}$cycloalkyl; $C_5$–$C_{12}$cycloalkyl which is substituted by $C_1$–$C_4$alkyl or interrupted by —O— or both substituted by $C_1$–$C_4$alkyl and interrupted by —O—;

$R_{14}$ is $C_1$–$C_{18}$alkyl; $C_2$–$C_{18}$alkyl which is substituted by a radical selected from $NH_2$, $NHR_{10}$, $N(R_{10})_2$, hydroxy, $OR_{13}$; $C_5$–$C_{12}$cycloalkyl which is unsubstituted or substituted by $C_1$–$C_4$alkyl or interrupted by —O— or both substituted by $C_1$–$C_4$alkyl and interrupted by —O—;

or $R_{14}$ is $C_7$–$C_{15}$phenylalkyl which is unsubstituted or substituted on the phenyl ring by a radical selected from $C_1$–$C_4$alkyl and $C_1$–$C_4$alkoxy;

$R_{15}$ is a direct bond; $C_1$–$C_{20}$alkylene; $C_2$–$C_{10}$alkenylene; $C_2$–$C_8$alkenylene substituted by a radical selected from $C_6$–$C_{12}$aryl or $C_6$–$C_{12}$aryl which is substituted by $C_1$–$C_8$alkyl, $C_1$–$C_8$alkoxy, di($C_1$–$C_4$-alkyl)amino, nitro, thienyl, phenoxyphenyl, phenylthiophenyl, benzo[b]thiophen-2-yl, benzofuran-2-yl, 9H-fluorenyl, biphenylyl, 10H-phenothiazinyl; or $R_{15}$ is $C_2$–$C_4$oxaalkylene; $C_5$–$C_7$cycloalkylene; $C_5$–$C_7$cycloalkenylene or phenylene;

when s is 2

W is $C_2$–$C_{12}$alkylene; $C_4$–$C_{12}$alkylene substituted by OH or interrupted by a divalent spacer selected from oxygen, sulfur and —$NR_{10}$—, or both substituted by OH and interrupted by a divalent spacer selected from oxygen, sulfur and —$NR_{10}$—; or W is $C_4$–$C_{12}$alkenylene; $C_6$–$C_{12}$alkenylene substituted by OH or interrupted by O or both substituted by OH and interrupted by O; $C_5$–$C_7$cycloalkylene; $C_5$–$C_7$cycloalkylene-di($C_1$–$C_4$alkylene); $C_1$–$C_4$alkylene-di($C_5$–$C_7$cyclo-alkylene); phenylene di($C_1$–$C_4$alkylene); or one of the groups of the formulae (IIIa)–(IIIe)

(IIIa)

—CO—$R_{18}$—CO;

(IIIb)

—COO—$R_{19}$—OOC—;

(IIIc)

—CONH—$R_{20}$—NHCO—;

(IIId)

—$(CH_2)_t$CO—;

(IIIe)

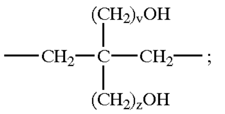

$R_{18}$ is a direct bond; $C_1$–$C_{12}$alkylene; $C_2$–$C_{12}$alkylene interrupted by a divalent spacer selected from oxygen, sulfur, —$NR_{10}$—; $C_5$–$C_7$cycloalkylene; $C_5$–$C_7$cycloalkenylene; phenylene; $C_2$–$C_8$alkenylene; $C_2$–$C_8$alkenylene substituted by $C_4$–$C_{12}$aryl or $C_4$-$C_{12}$aryl which is substituted by $C_1$–$C_8$alkyl, $C_1$–$C_8$alkoxy, di($C_1$–$C_4$-alkyl)amino, nitro; or $C_2C_8$alkenylene substituted by thienyl, phenoxyphenyl, phenylthiophenyl, benzo[b]thiophen-2-yl, benzofuran-2-yl, 9H-fluorenyl, biphenylyl, 10H-phenothiazinyl, thiofuranyl;

$R_{19}$ is $C_2$–$C_{12}$alkylene; $C_4$–$C_{12}$alkylene interrupted by oxygen; $C_5$–$C_7$cycloalkylene; $C_5$–$C_7$cycloalkylene di($C_1$–$C_4$alkylene); or $C_1$–$C_4$alkylidene di($C_5$–$C_7$cycloalkylene);

$R_{20}$ is $C_2$–$C_{12}$alkylene; $C_5$–$C_7$cycloalkylene; phenylene;

t is zero or an integer from 1 to 7;

v and z, independently of each other, are an integer from 1 to 4;

when s is 3

W is aliphatic $C_4$–$C_{18}$triacyl; cycloaliphatic $C_6$–$C_{18}$triacyl or aromatic $C_9$–$C_{18}$triacyl; or a group of the formula (IVa)

(IVa)

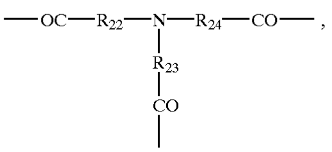

where $R_{22}$, $R_{23}$, $R_{24}$, independently of each other, are $C_1$–$C_7$alkylene;

when s is 4

W is aliphatic $C_5$–$C_{18}$tetraacyl; cycloaliphatic $C_8$–$C_{18}$tetraacyl or aromatic $C_{10}$–$C_{18}$tetraacyl when s is 5, W is aliphatic $C_7$–$C_{18}$pentaacyl; cycloaliphatic $C_{10}$–$C_{18}$pentaacyl or aromatic $C_{11}$–$C_{18}$pentaacyl;

when s is 6, W is aliphatic $C_8$–$C_{18}$hexaacyl; cycloaliphatic or aromatic $C_{12}$–$C_{18}$hexaacyl when s is 7, W is aliphatic, cycloaliphatic or aromatic $C_{12}$–$C_{18}$heptaacyl;

when s is 8, W is aliphatic, cycloaliphatic or aromatic $C_{12}$–$C_{18}$octaacyl with the proviso that when s is 1 and p is zero, that W is not $C_2$–$C_{18}$ alkyl which is substituted by hydroxy.

2. A compound according to claim 1 formula (I) wherein $R_w$, $R_x$, $R_y$ and $R_z$ are, independently of each other, $C_1$–$C_8$alkyl, cyclohexyl or $C_1$–$C_5$hydroxyalkyl;

$R_1$ is hydrogen; $C_1$–$C_8$alkyl; oxyl; OH; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkoxy; $C_1$–$C_8$alkanoyl; $C_3$–$C_5$alkenoyl; glycidyl; or a group —$CH_2$CH(OH)—G, in which G is hydrogen, methyl or phenyl;

$R_2$ and $R_6$, independently of each other, are hydrogen, $C_1$–$C_8$alkyl, cyclohexyl or $C_1$–$C_4$hydroxyalkyl;

$R_3$, $R_4$, $R_5$, $R_7$, $R_8$, $R_9$, independently of each other, are hydrogen, $C_1$–$C_8$alkyl or cyclohexyl;

when s is 1,

W is $C_4$–$C_{18}$alkyl; $C_2$–$C_{18}$alkyl which is substituted by a radical selected from $NH_2$, $NHR_{10}$, $N(R_{10})_2$, hydroxy, $OR'_{13}$; or W is $C_5$–$C_{12}$cycloalkyl; cyclohexyl which is substituted by OH, $C_1$–$C_4$alkyl or $C_1$–$C_4$alkoxy; $C_3$–$C_6$alkenyl; $C_3$–$C_{12}$epoxyalkyl; $C_7$–$C_{15}$phenylalkyl which is unsubstituted or substituted on the phenyl ring by a radical selected from $C_1$–$C_4$alkyl and $C_1$–$C_4$alkoxy; or W is one of the groups of the formulae (IIa)–(IIe)

(IIa)

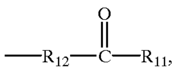

-continued (IIb)

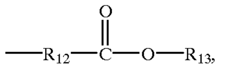

(IIc)

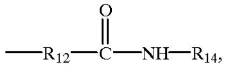

(IId)

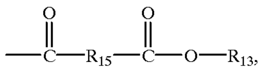

(IIe)

$—R_{12}—CN,$ or, when $R_1$ is a group $—CH_2CH(OH)—G$, W may also be hydrogen;

$R_{10}$ is hydrogen, $C_1$–$C_8$alkyl, $C_5$–$C_{12}$cycloalkyl, $C_7$–$C_{15}$phenylalkyl;

$R_{11}$ is hydrogen; $C_1$–$C_{17}$alkyl; $C_1$–$C_{12}$alkyl substituted by a radical selected from the group consisting of OH, $C_1$–$C_{12}$alkoxy, benzophenonyl, benzophenonyloxy, wherein one or both phenyl rings of the benzophenone moiety are unsubstituted or substituted by OH, halogen, $C_1$–$C_4$alkyl, $C_1$–$C_{18}$alkoxy; or $R_{11}$ is $C_5$–$C_{12}$cycloalkyl which is unsubstituted or substituted by $C_1$–$C_4$; $C_2$–$C_{17}$alkenyl; phenyl; phenyl substituted by $NH_2$, $NHR_{10}$, $N(R_{10})_2$, or $C_1$–$C_4$alkyl or $C_1$–$C_4$alkoxy; $C_7$–$C_{15}$phenylalkyl; or $C_7$–$C_{15}$phenylalkyl which is substituted on the phenyl ring by $C_1$–$C_4$alkyl and/or $C_1$–$C_4$alkoxy;

$R_{12}$ is a direct bond or $C_1$–$C_{12}$alkylene; phenylene; cyclohexylene;

$R_{13}$ is $C_1$–$C_{18}$alkyl; $C_2$–$C_{18}$alkyl which is substituted by a radical selected from $NH_2$, $NHR_{10}$, $N(R_{10})_2$, hydroxy and $OR_{13}$; $C_3$–$C_{18}$alkenyl; $C_5$–$C_{12}$cycloalkyl; cyclohexyl or oxacyclohexyl, each of which may be substituted by $C_1$–$C_4$alkyl; and when W is a group (IId) and when W is a group (IIb) while $R_{12}$ is not a direct bond, $R_{13}$ can be also hydrogen, or one equivalent of a sodium or potassium cation;

$R'_{13}$ is $C_1$–$C_{18}$alkyl; $C_2$–$C_{18}$alkyl which is substituted by a radical selected from $NH_2$, $NHR_{10}$, $N(R_{10})_2$, hydroxy and $OR_{13}$; $C_3$–$C_{18}$alkenyl; $C_5$–$C_{12}$cycloalkyl; oxacyclohexyl; cyclohexyl which is substituted by $C_1$–$C_4$alkyl;

$R_{14}$ is $C_1$–$C_{18}$alkyl; $C_2$–$C_{18}$alkyl which is substituted by a radical selected from $NH_2$, $NHR_{10}$, $N(R_{10})_2$, hydroxy and $OR_{13}$; $C_5$–$C_{12}$cycloalkyl or oxacyclohexyl each of which is unsubstituted or substituted by $C_1$–$C_4$alkyl; or $C_7$–$C_{15}$phenylalkyl which is unsubstituted or substituted on the phenyl ring by a radical selected from $C_1$–$C_4$alkyl and $C_1$–$C_4$alkoxy;

$R_{15}$ is a direct bond; $C_1$–$C_{20}$alkylene; $C_2$–$C_{10}$alkenylene; $C_2$–$C_8$alkenylene substituted by a radical selected from $C_6$–$C_{12}$aryl and $C_6$–$C_{12}$aryl which is substituted by $C_1$–$C_8$alkyl, $C_1$–$C_8$alkoxy, di($C_1$–$C_4$-alkyl)amino, nitro, thienyl, phenoxyphenyl, phenylthiophenyl, benzo[b]thiophen-2-yl, benzofuran-2-yl, 9H-fluorenyl, biphenylyl, 10H-phenothiazinyl; or $R_{15}$ is $C_2$–$C_4$oxaalkylene; $C_5$–$C_7$cycloalkylene; $C_5$–$C_7$cycloalkenylene; phenylene;

when s is 2

W is $C_2$–$C_{12}$alkylene; $C_4$–$C_{12}$alkylene substituted by OH and/or interrupted by oxygen or sulfur;

$C_4$–$C_{12}$alkenylene; $C_6$–$C_{12}$alkenylene substituted by OH and/or interrupted by O; $C_5$–$C_7$cycloalkylene; $C_5$–$C_7$cycloalkylene-di($C_1$–$C_4$alkylene); $C_1$–$C_4$alkylene-di($C_5$–$C_7$cyclo-alkylene); phenylene di($C_1$–$C_4$alkylene); or one of the groups of the formulae (IIIa)–(IIIe)

(IIIa)

$—CO—R_{18}—CO;$ (IIIb)

$—COO—R_{19}—OOC—;$ (IIIc)

$—CONH—R_{20}—NHCO—;$ (IIId)

$—(CH_2)_tCO—;$ (IIIe)

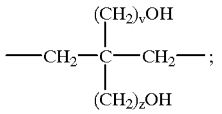

$R_{18}$ is a direct bond; $C_1$–$C_{12}$alkylene; $C_2$–$C_{12}$alkylene interrupted by oxygen, sulfur and/or $—NR_{10}—$; $C_5$–$C_7$cycloalkylene; $C_5$–$C_7$cycloalkenylene; or phenylene; $C_2$–$C_8$alkenylene; $C_2$–$C_8$alkenylene substituted by $C_4$–$C_{12}$aryl or $C_4$–$C_{12}$aryl which is substituted by $C_1$–$C_8$alkyl, $C_1$–$C_8$alkoxy, di($C_1$–$C_4$-alkyl)amino; or $C_2$–$C_8$alkenylene substituted by thienyl, phenoxyphenyl, phenyithiophenyl, benzo[b]thiophen-2-yl, benzofuran-2-yl, 9H-fluorenyl, biphenylyl, 10H-phenothiazinyl, thiofuranyl;

$R_{19}$ is $C_2$–$C_{12}$alkylene; $C_4$–$C_{12}$alkylene interrupted by 1, 2 or 3 oxygen atoms; $C_5$–$C_7$cycloalkylene; $C_5$–$C_7$cycloalkylene di($C_1$–$C_4$alkylene); or $C_1$–$C_4$alkylidene di($C_5$–$C_7$cycloalkylene);

$R_{20}$ is $C_2$–$C_{12}$alkylene; cyclohexylene; phenylene;

t is zero or an integer from 1 to 7;

v and z, independently of each other, are an integer from 1 to 4;

when s is 3

W is aliphatic $C_4$–$C_{18}$triacyl; cycloaliphatic $C_6$–$C_{18}$triacyl or aromatic $C_9$–$C_{18}$triacyl; or a group of the formulae (IVa)

(IVa)

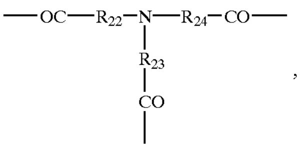

where $R_{22}$, $R_{23}$, $R_{24}$, independently of each other, are $C_1$–$C_7$alkylene;

when s is 4

W is aliphatic $C_5$–$C_{18}$tetraacyl; cycloaliphatic $C_8$–$C_{18}$tetraacyl or aromatic $C_{10}$–$C_{18}$tetraacyl when s is 5, W is aliphatic $C_7$–$C_{18}$pentaacyl; cycloaliphatic $C_{10}$–$C_{18}$pentaacyl or aromatic $C_{11}$–$C_{18}$pentaacyl;

when s is 6, W is aliphatic $C_8$–$C_{18}$hexaacyl; cycloaliphatic or aromatic $C_{12}$–$C_{18}$hexaacyl or when s is 7, W is aliphatic, cycloaliphatic or aromatic $C_{12}$–$C_{18}$heptaacyl;

when s is 8, W is aliphatic, cycloaliphatic or aromatic $C_{12}$–$C_{18}$octaacyl

3. A compound according to claim 1 of formula (I)

where p is zero or 1;

q and r, independently of each other, are an integer from 1 to 6;

s is 1, 2, 3, 4 or 6;

$R_w$, $R_x$, $R_y$ and $R_z$ each are methyl or ethyl;

$R_1$ is hydrogen; $C_1$–$C_8$alkyl; oxyl; OH; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkoxy; $C_1$–$C_8$alkanoyl; $C_3$–$C_5$alkenoyl; glycidyl; or a group —$CH_2CH(OH)$—G, in which G is hydrogen, methyl or phenyl;

$R_2$ and $R_6$, independently of each other, are hydrogen, $C_1$–$C_8$alkyl, cyclohexyl or $C_1$–$C_4$hydroxyalkyl;

$R_3$, $R_4$, $R_5$, $R_7$, $R_8$, $R_9$, independently of each other, are hydrogen or methyl;

X is —O— or, when p is 1, X is also a group

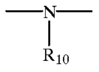

where $R_{10}$ is hydrogen, $C_1$–$C_8$alkyl, $C_5$–$C_{12}$cycloalkyl, $C_7$–$C_{15}$phenylalkyl which is unsubstituted or mono-, di- or tn-substituted or the phenyl by $C_1$–$C_4$alkyl;

when s is 1

W is $C_1$–$C_{18}$alkyl; $C_2$–$C_8$alkyl which is substituted by $NH_2$, $NHR_{10}$, $N(R_{10})_2$; $C_5$–$C_{12}$cycloalkyl; $C_3$–$C_6$alkenyl; glycidyl; $C_7$–$C_{15}$phenylalkyl which is unsubstituted or mono-, di- or tri-substituted on the phenyl ring by radicals selected from $C_1$–$C_4$alkyl and $C_1$–$C_4$alkoxy; or W is also a group of the above formula (IIb) or (IId) or a group of the formula (II'a) or (II'c):

(II'a)

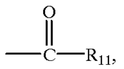

(II'c)

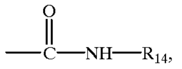

or, when $R_1$ is a group —$CH_2CH(OH)$—G, W may also be hydrogen;

$R_{11}$ is hydrogen; $C_1$–$C_{17}$alkyl; $C_5$–$C_{12}$cycloalkyl which is unsubstituted or mono-, di- or tri-substituted by $C_1$–$C_4$alkyl; $C_2$–$C_{17}$alkenyl; phenyl which is unsubstituted or substituted by $NH_2$, $NHR_{10}$, $N(R_{10})_2$ or $C_1$–$C_4$alkyl; $C_7$–$C_{15}$phenylalkyl which is unsubstituted or mono-, di- or tri-substituted on the phenyl ring by radicals selected from $C_1$–$C_4$alkyl, $C_1$–$C_4$alkoxy;

$R_{12}$ is a direct bond; $C_1$–$C_{12}$alkylene;

$R_{13}$ is $C_1$–$C_{18}$alkyl; $C_3$–$C_{18}$alkenyl; $C_5$–$C_{12}$cycloalkyl which is unsubstituted or mono-, di- or tri-substituted by $C_1$–$C_4$alkyl; and when W is a group (IId), $R_{13}$ can be also hydrogen, sodium or potassium;

$R_{14}$ is $C_1$–$C_{18}$alkyl; $C_5$–$C_{12}$cycloalkyl which is unsubstituted or mono-, di- or tri-substituted by $C_1$–$C_4$alkyl; or $C_7$–$C_{15}$phenylalkyl which is unsubstituted or mono-, di- or tri-substituted on the phenyl ring by radicals selected from $C_1$–$C_4$alkyl and $C_1$–$C_4$alkoxy;

$R_{15}$ is a direct bond; $C_1$–$C_{20}$alkylene; a group

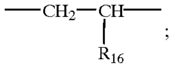

a group

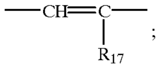

$C_2$–$C_4$oxaalkylene; $C_5$–$C_7$cycloalkylene; $C_5$–$C_7$cycloalkenylene or phenylene;

$R_{16}$ is $C_3$–$C_8$alkenyl; and $R_{17}$ is hydrogen or $C_1$–$C_8$alkyl;

when s is 2

W is $C_2$–$C_{12}$alkylene; $C_4$–$C_{12}$alkylene interrupted by 1, 2 or 3 oxygen atoms; $C_4$–$C_{12}$alkenylene; $C_5$–$C_7$cycloalkylene; $C_5$–$C_7$cycloalkylene di($C_1$–$C_4$alkylene); $C_1$–$C_4$alkylene di($C_5$–$C_7$cycloalkylene); $C_2$–$C_4$alkylidene di($C_5$–$C_7$cycloalkylene); phenylene di($C_1$–$C_4$alkylene); or one of the groups of the formulae (IIIa)–(IIIe)

$$—CO—R_{18}—CO; \qquad \text{(IIIa)}$$

$$—COO—R_{19}—OOC—; \qquad \text{(IIIb)}$$

$$—CONH—R_{20}—NHCO—; \qquad \text{(IIIc)}$$

$$—(CH_2)_tCO— \qquad \text{(IIId)}$$

(IIIe)

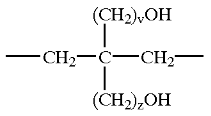

in which $R_{18}$ is a direct bond; $C_1$–$C_{12}$alkylene; $C_2$–$C_{12}$alkylene interrupted by O or S; $C_2$–$C_8$alkenylene; $C_5$–$C_7$cycloalkylene; $C_5$–$C_7$cycloalkenylene; or phenylene; or $C_2$–$C_8$alkenylene substituted by phenyl, naphthyl, thiofuranyl, or phenyl or naphthyl each of which is substituted by $C_1$–$C_4$alkyl or $C_1$–$C_4$alkoxy;

$R_{19}$ is $C_2$–$C_{12}$alkylene; $C_4$–$C_{12}$alkylene interrupted by 1, 2 or 3 oxygen atoms; $C_5$–$C_7$cycloalkylene; $C_5$–$C_7$cycloalkylene di($C_1$–$C_4$alkylene); or $C_1$–$C_4$alkylidene di($C_5$–$C_7$cycloalkylene);

$R_{20}$ is $C_2$–$C_{12}$alkylene; $C_5$–$C_7$cycloalkylene; or phenylene;

t is zero or an integer from 1 to 7;

v and z, independently of each other, are an integer from 1 to 4;

when s is 3

W is aliphatic $C_4$–$C_{18}$triacyl; aromatic $C_9$–$C_{18}$triacyl or a group of the formula (IVa);

when s is 4

W is aliphatic $C_6$–$C_{18}$tetraacyl; aromatic $C_{10}$–$C_{18}$tetraacyl or a group of the formula (V);

(V)

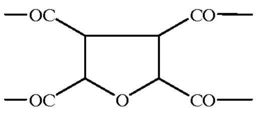

when s is 6, W is a 1,2,3,4,5,6-cyclohexane hexacarboxy residue.

4. A compound of formula (I')

(I')

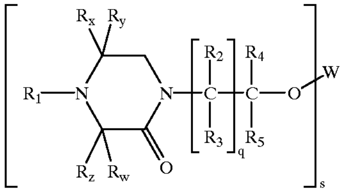

wherein r is 1 or 2; and s is a number 1, 2 or 6;

$R_w$, $R_x$, $R_y$ and $R_z$ are, independently of each other, methyl or ethyl;

$R_1$ is hydrogen; $C_1$–$C_4$alkyl; $C_3$–$C_{12}$alkoxy; cyclohexyloxy; acetyl; $C_3$–$C_5$alkenoyl; or $R_1$ is glycidyl or a group —$CH_2CH(OH)$—G, in which G is hydrogen or methyl;

$R_6$, $R_7$, $R_8$, $R_9$ independently of each other are hydrogen or methyl;

when s is 1,

W is $C_6$–$C_{18}$alkyl; cyclohexyl; $C_2$–$C_8$alkyl which is substituted by $NH_2$, $NHR_{10}$, $N(R_{10})_2$; or W is glycidyl; or W is a group of the formula (IIa)

(IIa)

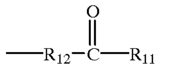

or, when $R_1$ is a group —$CH_2CH(OH)$—G, W may also be hydrogen;

$R_{10}$ is hydrogen, $C_1$–$C_8$alkyl, cyclohexyl;

$R_{11}$ is $C_1$–$C_{17}$alkyl; cyclohexyl; phenyl; phenyl substituted by $NH_2$, $NHR_{10}$, $N(R_{10})_2$;

$R_{12}$ is a direct bond;

when s is 2,

W is $C_2$–$C_{12}$alkylene; $C_4$–$C_{12}$alkylene interrupted by sulfur; or a group of the formula (IIIa)

$$CO—R_{18}—CO \quad \text{(IIIa);}$$

$R_{18}$ is $C_1$–$C_{12}$alkylene; $C_4$–$C_{12}$alkylene interrupted by O or S or $NR_{10}$; phenylene; cyclohexylene;

$C_2$–$C_8$alkenylene; $C_2$–$C_8$alkenylene substituted by a group

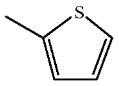

or by phenyl or naphthyl, or by phenyl or naphthyl, each of which is substituted by methyl or methoxy;

when s is 6,

W is cyclohexane hexaacyl

5. A compound of formula (I'')

(I'')

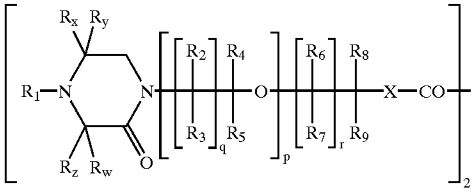

wherein $R_w$, $R_x$, $R_y$ and $R_z$ are, independently of each other, $C_1$–$C_{18}$alkyl, $C_5$–$C_{12}$cycloalkyl or $C_1$–$C_5$hydroxyalkyl;

$R_1$ is hydrogen; $C_1$–$C_{18}$alkyl; oxyl; OH; $CH_2CN$; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–$C_{15}$phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1$–$C_{18}$alkanoyloxy; glycidyl; or a group —$CH_2CH(OH)$—G, in which G is hydrogen, methyl or phenyl;

$R_2$, $R_3$, $R_4$, $R_5$, $R_6$, $R_7$, $R_8$, $R_9$, independently of each other, are hydrogen, $C_1$–$C_8$alkyl or $C_5$–$C_{12}$cycloalkyl;

p is zero or 1;

q and r, independently of each other, are integers from 1 to 6;

X is —O— or, when p is 1, X is also a group

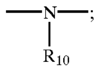

$R_{10}$ is hydrogen, $C_1$–$C_8$alkyl, $C_5$–$C_{12}$cycloalkyl, $C_7$–$C_{15}$phenylalkyl which is unsubstituted or substituted on the phenyl ring by a radical selected from $C_1$–$C_4$alkyl and $C_1$–$C_4$alkoxy;

$R_{25}$ is phenyl which is unsubstituted or mono-, di- or tri-substituted by $C_1$–$C_8$alkyl, $C_1$–$C_8$alkoxy, di($C_1$–$C_4$-alkyl)amino, nitro; or is phenyl which is mono- or di-substituted by a group of the formula (II'')

(II'')

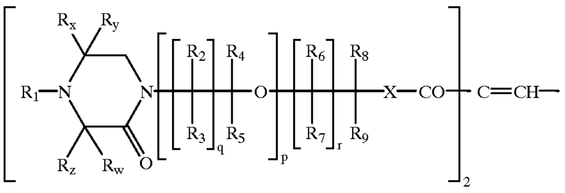

in which $R_w$, $R_x$, $R_y$, $R_z$, $R_1$, $R_2$, $R_3$, $R_4$, $R_5$, $R_6$, $R_7$, $R_8$, $R_9$, X, p, q, r are as defined above; or $R_{25}$ is naphtyl which is unsubstituted or mono-substituted by $C_1$–$C_4$alkyl, $C_1$–$C_4$alkoxy, di($C_1$–$C_4$-alkyl)amino or nitro; or $R_{25}$ is thienyl, phenoxyphenyl, phenylthiophenyl, benzothiophenyl, benzofuranyl, 9H-fluorenyl, biphenylyl, 10H-phenothiazinyl.

6. A compound 1-(2-hydroxyethyl)-3,3,5,5-tetramethyl-piperazin-2-one,
1-(2-hydroxyethyl)-3,3,4,5,5-pentamethyl-piperazin-2-one,
1-(2-hydroxypropyl)-3,3,5,5-tetramethyl-piperazin-2-one, 1-(2-hydroxypropyl)-3,3,4,5,5-pentamethyl-piperazin-2-one or a compound of the formula
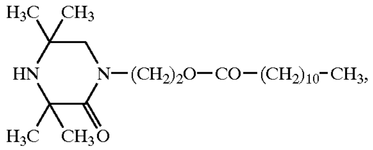
-continued
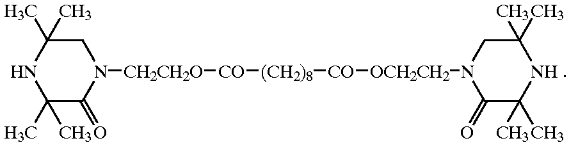
* * * * *